(12) United States Patent
Wang

(10) Patent No.: US 11,112,412 B1
(45) Date of Patent: Sep. 7, 2021

(54) SARS-COV-2 SURROGATE VIRUS NEUTRALIZATION ASSAY TEST KIT

(71) Applicant: National University of Singapore, Singapore (SG)

(72) Inventor: Linfa Wang, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 16/939,405

(22) Filed: Jul. 27, 2020

(30) Foreign Application Priority Data

Mar. 25, 2020 (SG) ............................ 10202002784P
May 14, 2020 (SG) ............................ 10202004468Q

(51) Int. Cl.
*G01N 33/68* (2006.01)
*C07K 14/165* (2006.01)
*A61J 1/00* (2006.01)
*C07K 16/10* (2006.01)

(52) U.S. Cl.
CPC ............ *G01N 33/6854* (2013.01); *A61J 1/00* (2013.01); *C07K 14/165* (2013.01); *C12Y 304/17023* (2013.01); *C07K 16/10* (2013.01); *C12N 2770/20021* (2013.01); *C12N 2770/20022* (2013.01); *G01N 2333/165* (2013.01); *G01N 2800/12* (2013.01)

(58) Field of Classification Search
CPC .................. C07K 14/165; C07K 16/10; C12Y 304/17023; C12N 2770/20022; C12N 2770/20021
See application file for complete search history.

(56) References Cited

U.S. PATENT DOCUMENTS

| 8,241,864 B2 * | 8/2012 | Loibner | G01N 33/573 435/23 |
| 2007/0190065 A1 * | 8/2007 | Altmeyer | C07K 14/005 424/159.1 |
| 2016/0238601 A1 * | 8/2016 | Baric | C07K 14/005 |

FOREIGN PATENT DOCUMENTS

| CN | 101522208 A | * | 9/2009 |
| CN | 101522208 A | | 9/2009 |
| CN | 111273016 A | * | 6/2020 |
| CN | 111273016 A | | 6/2020 |
| WO | 2005/032487 A2 | | 4/2005 |
| WO | 2005/120565 A2 | | 12/2005 |
| WO | 2009/128963 A2 | | 10/2009 |

OTHER PUBLICATIONS

Mittal, A., et al., 2020, COVID-19 pandemic: Insights into structure, function, and hACE2 receptor recognition by SARS-CoV-2, PLoS Pathog 16(8):1-19 (e1008762, https://doi.org/10.1371/journal.ppat.1008762.*

Kirtipal, N., et al., 2020, From SARS to SARS-CoV-2, insights on structure, pathogenicity and immunity aspects of pandemic human coronaviruses, Infect. Genet. Evolut. 85:1-15 (https://doi.org/10.1016/j.meegid.2020.104502).*
Hou, Y., et al., 2010, Angiotensin-converting enzyme 2 (ACE2) proteins of different bat species confer variable susceptibility to SARS-CoV entry, Arch. Virol. 155:1563-1569.*
Melin, A. D., et al., 2020, Comparative ACE2 variation and primate COVID-19 risk, Comm. Biol. 3:641, pp. 1-9, | https://doi.org/10.1038/S42003-020-01370-w.*
Lin, H.-X., et al., 2008, Identification of residues in the receptor-binding domain (RBD) of the spike protein of huma coronavirus NL63 that are critical for the RBD-ACE2 receptor interaction, J. Gen. Virol. 89:1015-1024.*
He, Y., et al., 2006, A single amino acid substitution (R441A) in the receptor-binding domain of SARS coronavirus spike protein disrupts the antigenic structure and binding activity, Biochem. Biophys. Res. Comm. 344:106-113.*
Tan, C. W., et al., 2020, A SARS-CoV-2 surrogate virus neutralization test based on antibody-mediated blockage of ACE2-spike protein-protein interaction, Nat. Biotech. pp. 1-17 (https://doi.org/10.1038/s41587-020-0631-z) (published Jul. 23, 2020).*
Darwish, I. A., 2006, Immunoassay methods and their applications in pharmaceutical analysis: basic methodology and recent advances, Intl. J. Biomed. Sci. 2(3):217-235.*
Wu, F., et al., Mar. 2020a, A new coronavirus associated with human respiratory disease in China, Nature 579:265-284 (published electronically Feb. 3, 2020).*
Wu, F., et al., Mar. 2020b, A new coronavirus associated with human respiratory disease in China, GenBank Submission MN908947 (VRL Mar. 18, 2020) pp. 1-12.*
He, Y., et al., 2004, Receptor-binding domain of SARS-CoV spike protein induces highly potent neutralizing antibodies: implication for developing subunit vaccine, Biochem. Biophys. Res. Comm. 324:773-781.*
Ho, T.-Y., et al., 2006, Design and biological activities of novel inhibitory peptides for SARS-CoV spike protein and angiotensin-converting enzyme 2 interaction, Antivir. Res. 69:70-76.*
L. Du, et al., Recombinant adeno-associated virus expressing the receptor-binding domain of severe acute respiratory syndrome coronavirus S protein elicits neutralizing antibodies: Implication for developing SARS vaccines, Virology (Sep. 15, 2006) vol. 353, No. 1, p. 6-16.
Chen Xiangyu, et al., Human monoclonal antibodies block the binding of SARS-CoV-2 spike protein to angiotensin converting enzyme 2 receptor, Cellular & Molecular Immunology, Chinese Society of Immunology (Apr. 20, 2020) CH, vol. 17, No. 6, p. 647-649.

(Continued)

*Primary Examiner* — Jeffrey S Parkin
(74) *Attorney, Agent, or Firm* — Duane Morris LLP; Thomas J. Kowalski; Deborah L. Lu

(57) ABSTRACT

A kit, composition and method for detection of antibodies to severe acute respiratory syndrome related coronavirus (SARSr-CoV), and for diagnosis of SARSr-CoV infection.

30 Claims, 17 Drawing Sheets
Specification includes a Sequence Listing.

(56) References Cited

OTHER PUBLICATIONS

James R. Byrnes, et al., A SARS-CoV-2 serological assay to determine the presence of blocking antibodies that compete for human ACE2 binding, medRxiv: the preprint server for health sciences, May 29, 2020. Retrieved from the Internet: URL:https://www.medrxiv.org/content/10.110 1/2020.05.27.20114652v1.full.pdf.

Edward P. Gniffke, et al., Plasma from recovered COVID19 subjects inhibits spike protein binding to ACE2 in a microsphere-based inhibition assay, medRxiv, Jun. 11, 2020.

Roujian Lu, et al., Genomic characterisation and epidemiology of 2019 novel coronavirus: implications for virus origins and receptor binding, The Lancet (Feb. 22, 2020) vol. 395, No. 10224, p. 565-574.

Office Action dated Mar. 1, 2021 in co-pending Chinese Application No. CN202010720353.4.

EP Search Report and Written Opinion dated Feb. 4, 2021, in co-pending EP Application No. 20193156.5.

\* cited by examiner

| Sample | VNT | sVNT | | | |
|---|---|---|---|---|---|
| | | 90% | 70% | 50% | 30% |
| COVID-19 Patient-1 | <10 | <10 | 10 | 20 | 40 |
| COVID-19 Patient-2 | 40 | 20 | 40 | 80 | 320 |
| COVID-19 Patient-3 | 20 | <10 | 20 | 40 | 80 |
| COVID-19 Patient-4 | 10 | <10 | <10 | 10 | 20 |
| COVID-19 Patient-5 | 20 | 10 | 20 | 40 | 80 |
| COVID-19 Patient-6 | <10 | <10 | <10 | 10 | 20 |
| COVID-19 Patient-7 | 40 | <10 | 20 | 40 | 80 |
| COVID-19 Patient-8 | 10 | <10 | 20 | 40 | 80 |
| COVID-19 Patient-9 | 20 | 10 | 20 | 40 | 80 |
| COVID-19 Patient-10 | 10 | 10 | 40 | 80 | 160 |
| COVID-19 Patient-11 | 20 | 20 | 80 | 160 | 640 |
| COVID-19 Patient-12 | 80 | 20 | 80 | 160 | 640 |
| COVID-19 Patient-13 | 160 | 160 | 320 | 640 | 1280 |
| Negative Control-1 | <10 | <10 | <10 | <10 | <10 |
| Negative Control-2 | <10 | <10 | <10 | <10 | <10 |

SEQUENCE LISTING

```
<160> NUMBER OF SEQ ID NOS: 34

<210> SEQ ID NO 1
<211> LENGTH: 1255
<212> TYPE: PRT
<213> ORGANISM: SARS-CoV

<400> SEQUENCE: 1

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Asp Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190
```

```
Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
210                 215                 220

Gly Ile Asn Ile Thr Asn Phe Arg Ala Ile Leu Thr Ala Phe Ser Pro
225                 230                 235                 240

Ala Gln Asp Thr Trp Gly Thr Ser Ala Ala Tyr Phe Val Gly Tyr
            245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
            290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
            405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
            450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
            565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605
```

```
Ala Ile His Ala Asp Gln Leu Thr Pro Ala Trp Arg Ile Tyr Ser Thr
610             615                 620

Gly Asn Asn Val Phe Gln Thr Gln Ala Gly Cys Leu Ile Gly Ala Glu
625             630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
                660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
                740                 745                 750

Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
                820                 825                 830

Cys Ala Gln Lys Phe Asn Gly Leu Thr Val Leu Pro Pro Leu Leu Thr
            835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
                900                 905                 910

Ile Ser Gln Ile Gln Glu Ser Leu Thr Thr Thr Ser Thr Ala Leu Gly
            915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
                980                 985                 990

Gln Leu Ile Arg Ala Ala Glu Ile  Arg Ala Ser Ala Asn  Leu Ala Ala
            995                 1000                 1005

Thr Lys  Met Ser Glu Cys Val  Leu Gly Gln Ser Lys  Arg Val Asp
    1010                 1015                 1020

Phe Cys  Gly Lys Gly Tyr His  Leu Met Ser Phe Pro  Gln Ala Ala
```

```
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Leu Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230

Ser Cys  Cys Lys Phe Asp Glu  Asp Asp Ser Glu Pro  Val Leu Lys
    1235                1240                1245

Gly Val  Lys Leu His Tyr Thr
    1250                1255

<210> SEQ ID NO 2
<211> LENGTH: 76
<212> TYPE: PRT
<213> ORGANISM: SARS-CoV

<400> SEQUENCE: 2

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Thr Val Tyr Val Tyr Ser Arg Val Lys Asn
    50                  55                  60

Leu Asn Ser Ser Glu Gly Val Pro Asp Leu Leu Val
65                  70                  75

<210> SEQ ID NO 3
<211> LENGTH: 221
<212> TYPE: PRT
<213> ORGANISM: SARS-CoV

<400> SEQUENCE: 3

Met Ala Asp Asn Gly Thr Ile Thr Val Glu Glu Leu Lys Gln Leu Leu
```

```
                1               5                   10                  15
            Glu Gln Trp Asn Leu Val Ile Gly Phe Leu Phe Leu Ala Trp Ile Met
                            20                  25                  30

Leu Leu Gln Phe Ala Tyr Ser Asn Arg Asn Arg Phe Leu Tyr Ile Ile
                            35                  40                  45

Lys Leu Val Phe Leu Trp Leu Leu Trp Pro Val Thr Leu Ala Cys Phe
                            50                  55                  60

Val Leu Ala Ala Val Tyr Arg Ile Asn Trp Val Thr Gly Gly Ile Ala
             65                 70                  75                  80

Ile Ala Met Ala Cys Ile Val Gly Leu Met Trp Leu Ser Tyr Phe Val
                            85                  90                  95

Ala Ser Phe Arg Leu Phe Ala Arg Thr Arg Ser Met Trp Ser Phe Asn
                            100                 105                 110

Pro Glu Thr Asn Ile Leu Leu Asn Val Pro Leu Arg Gly Thr Ile Val
                            115                 120                 125

Thr Arg Pro Leu Met Glu Ser Glu Leu Val Ile Gly Ala Val Ile Ile
                            130                 135                 140

Arg Gly His Leu Arg Met Ala Gly His Ser Leu Gly Arg Cys Asp Ile
            145                 150                 155                 160

Lys Asp Leu Pro Lys Glu Ile Thr Val Ala Thr Ser Arg Thr Leu Ser
                            165                 170                 175

Tyr Tyr Lys Leu Gly Ala Ser Gln Arg Val Gly Thr Asp Ser Gly Phe
                            180                 185                 190

Ala Ala Tyr Asn Arg Tyr Arg Ile Gly Asn Tyr Lys Leu Asn Thr Asp
                            195                 200                 205

His Ala Gly Ser Asn Asp Asn Ile Ala Leu Leu Val Gln
                            210                 215                 220

<210> SEQ ID NO 4
            <211> LENGTH: 422
            <212> TYPE: PRT
            <213> ORGANISM: SARS-CoV

<400> SEQUENCE: 4

Met Ser Asp Asn Gly Pro Gln Ser Asn Gln Arg Ser Ala Pro Arg Ile
             1               5                   10                  15

Thr Phe Gly Gly Pro Thr Asp Ser Thr Asp Asn Asn Gln Asn Gly Gly
                            20                  25                  30

Arg Asn Gly Ala Arg Pro Lys Gln Arg Arg Pro Gln Gly Leu Pro Asn
                            35                  40                  45

Asn Thr Ala Ser Trp Phe Thr Ala Leu Thr Gln His Gly Lys Glu Glu
                            50                  55                  60

Leu Arg Phe Pro Arg Gly Gln Gly Val Pro Ile Asn Thr Asn Ser Gly
             65                 70                  75                  80

Pro Asp Asp Gln Ile Gly Tyr Tyr Arg Arg Ala Thr Arg Arg Val Arg
                            85                  90                  95

Gly Gly Asp Gly Lys Met Lys Glu Leu Ser Pro Arg Trp Tyr Phe Tyr
                            100                 105                 110

Tyr Leu Gly Thr Gly Pro Glu Ala Ser Leu Pro Tyr Gly Ala Asn Lys
                            115                 120                 125

Glu Gly Ile Val Trp Val Ala Thr Glu Gly Ala Leu Asn Thr Pro Lys
                            130                 135                 140

Asp His Ile Gly Thr Arg Asn Pro Asn Asn Ala Ala Thr Val Leu
            145                 150                 155                 160
```

-continued

```
Gln Leu Pro Gln Gly Thr Thr Leu Pro Lys Gly Phe Tyr Ala Glu Gly
                165                 170                 175

Ser Arg Gly Gly Ser Gln Ala Ser Ser Arg Ser Ser Ser Arg Ser Arg
            180                 185                 190

Gly Asn Ser Arg Asn Ser Thr Pro Gly Ser Ser Arg Gly Asn Ser Pro
        195                 200                 205

Ala Arg Met Ala Ser Gly Gly Glu Thr Ala Leu Ala Leu Leu Leu Leu
    210                 215                 220

Leu Asp Arg Leu Asn Gln Leu Glu Ser Lys Val Ser Gly Lys Gly Gln
225                 230                 235                 240

Gln Gln Gln Gly Gln Thr Val Thr Lys Lys Ser Ala Ala Glu Ala Ser
                245                 250                 255

Lys Lys Pro Arg Gln Lys Arg Thr Ala Thr Lys Gln Tyr Asn Val Thr
            260                 265                 270

Gln Ala Phe Gly Arg Arg Gly Pro Glu Gln Thr Gln Gly Asn Phe Gly
        275                 280                 285

Asp Gln Asp Leu Ile Arg Gln Gly Thr Asp Tyr Lys His Trp Pro Gln
    290                 295                 300

Ile Ala Gln Phe Ala Pro Ser Ala Ser Ala Phe Phe Gly Met Ser Arg
305                 310                 315                 320

Ile Gly Met Glu Val Thr Pro Ser Gly Thr Trp Leu Thr Tyr His Gly
                325                 330                 335

Ala Ile Lys Leu Asp Asp Lys Asp Pro Gln Phe Lys Asp Asn Val Ile
            340                 345                 350

Leu Leu Asn Lys His Ile Asp Ala Tyr Lys Thr Phe Pro Pro Thr Glu
        355                 360                 365

Pro Lys Lys Asp Lys Lys Lys Thr Asp Glu Ala Gln Pro Leu Pro
    370                 375                 380

Gln Arg Gln Lys Lys Gln Pro Thr Val Thr Leu Leu Pro Ala Ala Asp
385                 390                 395                 400

Met Asp Asp Phe Ser Arg Gln Leu Gln Asn Ser Met Ser Gly Ala Ser
                405                 410                 415

Ala Asp Ser Thr Gln Ala
            420

<210> SEQ ID NO 5
<211> LENGTH: 1282
<212> TYPE: PRT
<213> ORGANISM: SARS-CoV-2

<400> SEQUENCE: 5

Met Phe Leu Leu Thr Thr Lys Arg Thr Met Phe Val Phe Leu Val Leu
1               5                   10                  15

Leu Pro Leu Val Ser Ser Gln Cys Val Asn Leu Thr Thr Arg Thr Gln
            20                  25                  30

Leu Pro Pro Ala Tyr Thr Asn Ser Phe Thr Arg Gly Val Tyr Tyr Pro
        35                  40                  45

Asp Lys Val Phe Arg Ser Ser Val Leu His Ser Thr Gln Asp Leu Phe
    50                  55                  60

Leu Pro Phe Phe Ser Asn Val Thr Trp Phe His Ala Ile His Val Ser
65                  70                  75                  80

Gly Thr Asn Gly Thr Lys Arg Phe Asp Asn Pro Val Leu Pro Phe Asn
                85                  90                  95

Asp Gly Val Tyr Phe Ala Ser Thr Glu Lys Ser Asn Ile Ile Arg Gly
            100                 105                 110
```

```
Trp Ile Phe Gly Thr Thr Leu Asp Ser Lys Thr Gln Ser Leu Leu Ile
            115                 120                 125

Val Asn Asn Ala Thr Asn Val Ile Lys Val Cys Glu Phe Gln Phe
    130                 135                 140

Cys Asn Asp Pro Phe Leu Gly Val Tyr Tyr His Lys Asn Asn Lys Ser
145                 150                 155                 160

Trp Met Glu Ser Glu Phe Arg Val Tyr Ser Ser Ala Asn Asn Cys Thr
                165                 170                 175

Phe Glu Tyr Val Ser Gln Pro Phe Leu Met Asp Leu Glu Gly Lys Gln
                180                 185                 190

Gly Asn Phe Lys Asn Leu Arg Glu Phe Val Phe Lys Asn Ile Asp Gly
            195                 200                 205

Tyr Phe Lys Ile Tyr Ser Lys His Thr Pro Ile Asn Leu Val Arg Asp
    210                 215                 220

Leu Pro Gln Gly Phe Ser Ala Leu Glu Pro Leu Val Asp Leu Pro Ile
225                 230                 235                 240

Gly Ile Asn Ile Thr Arg Phe Gln Thr Leu Leu Ala Leu His Arg Ser
                245                 250                 255

Tyr Leu Thr Pro Gly Asp Ser Ser Ser Gly Trp Thr Ala Gly Ala Ala
                260                 265                 270

Ala Tyr Tyr Val Gly Tyr Leu Gln Pro Arg Thr Phe Leu Leu Lys Tyr
    275                 280                 285

Asn Glu Asn Gly Thr Ile Thr Asp Ala Val Asp Cys Ala Leu Asp Pro
290                 295                 300

Leu Ser Glu Thr Lys Cys Thr Leu Lys Ser Phe Thr Val Glu Lys Gly
305                 310                 315                 320

Ile Tyr Gln Thr Ser Asn Phe Arg Val Gln Pro Thr Glu Ser Ile Val
                325                 330                 335

Arg Phe Pro Asn Ile Thr Asn Leu Cys Pro Phe Gly Glu Val Phe Asn
                340                 345                 350

Ala Thr Arg Phe Ala Ser Val Tyr Ala Trp Asn Arg Lys Arg Ile Ser
            355                 360                 365

Asn Cys Val Ala Asp Tyr Ser Val Leu Tyr Asn Ser Ala Ser Phe Ser
    370                 375                 380

Thr Phe Lys Cys Tyr Gly Val Ser Pro Thr Lys Leu Asn Asp Leu Cys
385                 390                 395                 400

Phe Thr Asn Val Tyr Ala Asp Ser Phe Val Ile Arg Gly Asp Glu Val
                405                 410                 415

Arg Gln Ile Ala Pro Gly Gln Thr Gly Lys Ile Ala Asp Tyr Asn Tyr
                420                 425                 430

Lys Leu Pro Asp Asp Phe Thr Gly Cys Val Ile Ala Trp Asn Ser Asn
            435                 440                 445

Asn Leu Asp Ser Lys Val Gly Gly Asn Tyr Asn Tyr Leu Tyr Arg Leu
    450                 455                 460

Phe Arg Lys Ser Asn Leu Lys Pro Phe Glu Arg Asp Ile Ser Thr Glu
465                 470                 475                 480

Ile Tyr Gln Ala Gly Ser Thr Pro Cys Asn Gly Val Glu Gly Phe Asn
                485                 490                 495

Cys Tyr Phe Pro Leu Gln Ser Tyr Gly Phe Gln Pro Thr Asn Gly Val
                500                 505                 510

Gly Tyr Gln Pro Tyr Arg Val Val Val Leu Ser Phe Glu Leu Leu His
            515                 520                 525
```

```
Ala Pro Ala Thr Val Cys Gly Pro Lys Lys Ser Thr Asn Leu Val Lys
        530                 535                 540

Asn Lys Cys Val Asn Phe Asn Phe Asn Gly Leu Thr Gly Thr Gly Val
545                 550                 555                 560

Leu Thr Glu Ser Asn Lys Lys Phe Leu Pro Phe Gln Gln Phe Gly Arg
                565                 570                 575

Asp Ile Ala Asp Thr Thr Asp Ala Val Arg Asp Pro Gln Thr Leu Glu
            580                 585                 590

Ile Leu Asp Ile Thr Pro Cys Ser Phe Gly Gly Val Ser Val Ile Thr
        595                 600                 605

Pro Gly Thr Asn Thr Ser Asn Gln Val Ala Val Leu Tyr Gln Asp Val
    610                 615                 620

Asn Cys Thr Glu Val Pro Val Ala Ile His Ala Asp Gln Leu Thr Pro
625                 630                 635                 640

Thr Trp Arg Val Tyr Ser Thr Gly Ser Asn Val Phe Gln Thr Arg Ala
                645                 650                 655

Gly Cys Leu Ile Gly Ala Glu His Val Asn Asn Ser Tyr Glu Cys Asp
            660                 665                 670

Ile Pro Ile Gly Ala Gly Ile Cys Ala Ser Tyr Gln Thr Gln Thr Asn
        675                 680                 685

Ser Pro Arg Arg Ala Arg Ser Val Ala Ser Gln Ser Ile Ile Ala Tyr
    690                 695                 700

Thr Met Ser Leu Gly Ala Glu Asn Ser Val Ala Tyr Ser Asn Asn Ser
705                 710                 715                 720

Ile Ala Ile Pro Thr Asn Phe Thr Ile Ser Val Thr Thr Glu Ile Leu
                725                 730                 735

Pro Val Ser Met Thr Lys Thr Ser Val Asp Cys Thr Met Tyr Ile Cys
            740                 745                 750

Gly Asp Ser Thr Glu Cys Ser Asn Leu Leu Leu Gln Tyr Gly Ser Phe
        755                 760                 765

Cys Thr Gln Leu Asn Arg Ala Leu Thr Gly Ile Ala Val Glu Gln Asp
    770                 775                 780

Lys Asn Thr Gln Glu Val Phe Ala Gln Val Lys Gln Ile Tyr Lys Thr
785                 790                 795                 800

Pro Pro Ile Lys Asp Phe Gly Gly Phe Asn Phe Ser Gln Ile Leu Pro
                805                 810                 815

Asp Pro Ser Lys Pro Ser Lys Arg Ser Phe Ile Glu Asp Leu Leu Phe
            820                 825                 830

Asn Lys Val Thr Leu Ala Asp Ala Gly Phe Ile Lys Gln Tyr Gly Asp
        835                 840                 845

Cys Leu Gly Asp Ile Ala Ala Arg Asp Leu Ile Cys Ala Gln Lys Phe
    850                 855                 860

Asn Gly Leu Thr Val Leu Pro Pro Leu Leu Thr Asp Glu Met Ile Ala
865                 870                 875                 880

Gln Tyr Thr Ser Ala Leu Leu Ala Gly Thr Ile Thr Ser Gly Trp Thr
                885                 890                 895

Phe Gly Ala Gly Ala Ala Leu Gln Ile Pro Phe Ala Met Gln Met Ala
            900                 905                 910

Tyr Arg Phe Asn Gly Ile Gly Val Thr Gln Asn Val Leu Tyr Glu Asn
        915                 920                 925

Gln Lys Leu Ile Ala Asn Gln Phe Asn Ser Ala Ile Gly Lys Ile Gln
    930                 935                 940

Asp Ser Leu Ser Ser Thr Ala Ser Ala Leu Gly Lys Leu Gln Asp Val
```

```
945                 950                 955                 960

Val Asn Gln Asn Ala Gln Ala Leu Asn Thr Leu Val Lys Gln Leu Ser
                965                 970                 975

Ser Asn Phe Gly Ala Ile Ser Ser Val Leu Asn Asp Ile Leu Ser Arg
            980                 985                 990

Leu Asp Lys Val Glu Ala Glu Val  Gln Ile Asp Arg Leu  Ile Thr Gly
        995                 1000                1005

Arg Leu  Gln Ser Leu Gln Thr  Tyr Val Thr Gln Gln  Leu Ile Arg
    1010                 1015                 1020

Ala Ala  Glu Ile Arg Ala Ser  Ala Asn Leu Ala Ala  Thr Lys Met
    1025                 1030                 1035

Ser Glu  Cys Val Leu Gly Gln  Ser Lys Arg Val Asp  Phe Cys Gly
    1040                 1045                 1050

Lys Gly  Tyr His Leu Met Ser  Phe Pro Gln Ser Ala  Pro His Gly
    1055                 1060                 1065

Val Val  Phe Leu His Val Thr  Tyr Val Pro Ala Gln  Glu Lys Asn
    1070                 1075                 1080

Phe Thr  Thr Ala Pro Ala Ile  Cys His Asp Gly Lys  Ala His Phe
    1085                 1090                 1095

Pro Arg  Glu Gly Val Phe Val  Ser Asn Gly Thr His  Trp Phe Val
    1100                 1105                 1110

Thr Gln  Arg Asn Phe Tyr Glu  Pro Gln Ile Ile Thr  Thr Asp Asn
    1115                 1120                 1125

Thr Phe  Val Ser Gly Asn Cys  Asp Val Val Ile Gly  Ile Val Asn
    1130                 1135                 1140

Asn Thr  Val Tyr Asp Pro Leu  Gln Pro Glu Leu Asp  Ser Phe Lys
    1145                 1150                 1155

Glu Glu  Leu Asp Lys Tyr Phe  Lys Asn His Thr Ser  Pro Asp Val
    1160                 1165                 1170

Asp Leu  Gly Asp Ile Ser Gly  Ile Asn Ala Ser Val  Val Asn Ile
    1175                 1180                 1185

Gln Lys  Glu Ile Asp Arg Leu  Asn Glu Val Ala Lys  Asn Leu Asn
    1190                 1195                 1200

Glu Ser  Leu Ile Asp Leu Gln  Glu Leu Gly Lys Tyr  Glu Gln Tyr
    1205                 1210                 1215

Ile Lys  Trp Pro Trp Tyr Ile  Trp Leu Gly Phe Ile  Ala Gly Leu
    1220                 1225                 1230

Ile Ala  Ile Val Met Val Thr  Ile Met Leu Cys Cys  Met Thr Ser
    1235                 1240                 1245

Cys Cys  Ser Cys Leu Lys Gly  Cys Cys Ser Cys Gly  Ser Cys Cys
    1250                 1255                 1260

Lys Phe  Asp Glu Asp Asp Ser  Glu Pro Val Leu Lys  Gly Val Lys
    1265                 1270                 1275

Leu His  Tyr Thr
    1280

<210> SEQ ID NO 6
<211> LENGTH: 75
<212> TYPE: PRT
<213> ORGANISM: SARS-CoV-2

<400> SEQUENCE: 6

Met Tyr Ser Phe Val Ser Glu Glu Thr Gly Thr Leu Ile Val Asn Ser
1               5                   10                  15
```

-continued

```
Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75

<210> SEQ ID NO 7
<211> LENGTH: 222
<212> TYPE: PRT
<213> ORGANISM: SARS-CoV-2

<400> SEQUENCE: 7

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80

Ala Ile Ala Met Ala Cys Leu Val Gly Leu Met Trp Leu Ser Tyr Phe
                85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
    130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
        195                 200                 205

Asp His Ser Ser Ser Ser Asp Asn Ile Ala Leu Leu Val Gln
    210                 215                 220

<210> SEQ ID NO 8
<211> LENGTH: 419
<212> TYPE: PRT
<213> ORGANISM: SARS-CoV-2

<400> SEQUENCE: 8

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
            20                  25                  30

Ser Gly Ala Arg Ser Lys Gln Arg Arg Pro Gln Gly Leu Pro Asn Asn
        35                  40                  45
```

-continued

```
Thr Ala Ser Trp Phe Thr Ala Leu Thr Gln His Gly Lys Glu Asp Leu
 50                  55                  60
Lys Phe Pro Arg Gly Gln Gly Val Pro Ile Asn Thr Asn Ser Ser Pro
 65                  70                  75                  80
Asp Asp Gln Ile Gly Tyr Tyr Arg Arg Ala Thr Arg Arg Ile Arg Gly
                 85                  90                  95
Gly Asp Gly Lys Met Lys Asp Leu Ser Pro Arg Trp Tyr Phe Tyr Tyr
            100                 105                 110
Leu Gly Thr Gly Pro Glu Ala Gly Leu Pro Tyr Gly Ala Asn Lys Asp
            115                 120                 125
Gly Ile Ile Trp Val Ala Thr Glu Gly Ala Leu Asn Thr Pro Lys Asp
130                 135                 140
His Ile Gly Thr Arg Asn Pro Ala Asn Asn Ala Ala Ile Val Leu Gln
145                 150                 155                 160
Leu Pro Gln Gly Thr Thr Leu Pro Lys Gly Phe Tyr Ala Glu Gly Ser
                165                 170                 175
Arg Gly Gly Ser Gln Ala Ser Ser Arg Ser Ser Ser Arg Ser Arg Asn
            180                 185                 190
Ser Ser Arg Asn Ser Thr Pro Gly Ser Ser Arg Gly Thr Ser Pro Ala
            195                 200                 205
Arg Met Ala Gly Asn Gly Gly Asp Ala Ala Leu Ala Leu Leu Leu Leu
210                 215                 220
Asp Arg Leu Asn Gln Leu Glu Ser Lys Met Ser Gly Lys Gly Gln Gln
225                 230                 235                 240
Gln Gln Gly Gln Thr Val Thr Lys Lys Ser Ala Ala Glu Ala Ser Lys
                245                 250                 255
Lys Pro Arg Gln Lys Arg Thr Ala Thr Lys Ala Tyr Asn Val Thr Gln
            260                 265                 270
Ala Phe Gly Arg Arg Gly Pro Glu Gln Thr Gln Gly Asn Phe Gly Asp
            275                 280                 285
Gln Glu Leu Ile Arg Gln Gly Thr Asp Tyr Lys His Trp Pro Gln Ile
            290                 295                 300
Ala Gln Phe Ala Pro Ser Ala Ser Ala Phe Phe Gly Met Ser Arg Ile
305                 310                 315                 320
Gly Met Glu Val Thr Pro Ser Gly Thr Trp Leu Thr Tyr Thr Gly Ala
                325                 330                 335
Ile Lys Leu Asp Asp Lys Asp Pro Asn Phe Lys Asp Gln Val Ile Leu
            340                 345                 350
Leu Asn Lys His Ile Asp Ala Tyr Lys Thr Phe Pro Pro Thr Glu Pro
            355                 360                 365
Lys Lys Asp Lys Lys Lys Ala Asp Glu Thr Gln Ala Leu Pro Gln
            370                 375                 380
Arg Gln Lys Lys Gln Gln Thr Val Thr Leu Leu Pro Ala Ala Asp Leu
385                 390                 395                 400
Asp Asp Phe Ser Lys Gln Leu Gln Gln Ser Met Ser Ser Ala Asp Ser
                405                 410                 415
Thr Gln Ala
```

<210> SEQ ID NO 9
<211> LENGTH: 654
<212> TYPE: PRT
<213> ORGANISM: SARS-CoV

<400> SEQUENCE: 9

-continued

```
Ser Asp Leu Asp Arg Cys Thr Thr Phe Asp Val Gln Ala Pro Asn
  1               5                  10                  15

Tyr Thr Gln His Thr Ser Ser Met Arg Gly Val Tyr Tyr Pro Asp Glu
             20                  25                  30

Ile Phe Arg Ser Asp Thr Leu Tyr Leu Thr Gln Asp Leu Phe Leu Pro
             35                  40                  45

Phe Tyr Ser Asn Val Thr Gly Phe His Thr Ile Asn His Thr Phe Asp
 50                  55                  60

Asn Pro Val Ile Pro Phe Lys Asp Gly Ile Tyr Phe Ala Ala Thr Glu
 65                  70                  75                  80

Lys Ser Asn Val Val Arg Gly Trp Val Phe Gly Ser Thr Met Asn Asn
                 85                  90                  95

Lys Ser Gln Ser Val Ile Ile Ile Asn Asn Ser Thr Asn Val Val Ile
                100                 105                 110

Arg Ala Cys Asn Phe Glu Leu Cys Asp Asn Pro Phe Phe Ala Val Ser
             115                 120                 125

Lys Pro Met Gly Thr Gln Thr His Thr Met Ile Phe Asp Asn Ala Phe
             130                 135                 140

Asn Cys Thr Phe Glu Tyr Ile Ser Asp Ala Phe Ser Leu Asp Val Ser
145                 150                 155                 160

Glu Lys Ser Gly Asn Phe Lys His Leu Arg Glu Phe Val Phe Lys Asn
                165                 170                 175

Lys Asp Gly Phe Leu Tyr Val Tyr Lys Gly Tyr Gln Pro Ile Asp Val
             180                 185                 190

Val Arg Asp Leu Pro Ser Gly Phe Asn Thr Leu Lys Pro Ile Phe Lys
             195                 200                 205

Leu Pro Leu Gly Ile Asn Ile Thr Asn Phe Arg Ala Ile Leu Thr Ala
             210                 215                 220

Phe Ser Pro Ala Gln Asp Thr Trp Gly Thr Ser Ala Ala Ala Tyr Phe
225                 230                 235                 240

Val Gly Tyr Leu Lys Pro Thr Thr Phe Met Leu Lys Tyr Asp Glu Asn
                245                 250                 255

Gly Thr Ile Thr Asp Ala Val Asp Cys Ser Gln Asn Pro Leu Ala Glu
             260                 265                 270

Leu Lys Cys Ser Val Lys Ser Phe Glu Ile Asp Lys Gly Ile Tyr Gln
             275                 280                 285

Thr Ser Asn Phe Arg Val Val Pro Ser Gly Asp Val Val Arg Phe Pro
290                 295                 300

Asn Ile Thr Asn Leu Cys Pro Phe Gly Glu Val Phe Asn Ala Thr Lys
305                 310                 315                 320

Phe Pro Ser Val Tyr Ala Trp Glu Arg Lys Lys Ile Ser Asn Cys Val
                325                 330                 335

Ala Asp Tyr Ser Val Leu Tyr Asn Ser Thr Phe Phe Ser Thr Phe Lys
             340                 345                 350

Cys Tyr Gly Val Ser Ala Thr Lys Leu Asn Asp Leu Cys Phe Ser Asn
             355                 360                 365

Val Tyr Ala Asp Ser Phe Val Val Lys Gly Asp Asp Val Arg Gln Ile
             370                 375                 380

Ala Pro Gly Gln Thr Gly Val Ile Ala Asp Tyr Asn Tyr Lys Leu Pro
385                 390                 395                 400

Asp Asp Phe Met Gly Cys Val Leu Ala Trp Asn Thr Arg Asn Ile Asp
                405                 410                 415

Ala Thr Ser Thr Gly Asn Tyr Asn Tyr Lys Tyr Arg Tyr Leu Arg His
```

```
                    420             425             430
Gly Lys Leu Arg Pro Phe Glu Arg Asp Ile Ser Asn Val Pro Phe Ser
            435                 440                 445
Pro Asp Gly Lys Pro Cys Thr Pro Pro Ala Leu Asn Cys Tyr Trp Pro
    450                 455                 460
Leu Asn Asp Tyr Gly Phe Tyr Thr Thr Thr Gly Ile Gly Tyr Gln Pro
465                 470                 475                 480
Tyr Arg Val Val Val Leu Ser Phe Glu Leu Leu Asn Ala Pro Ala Thr
                485                 490                 495
Val Cys Gly Pro Lys Leu Ser Thr Asp Leu Ile Lys Asn Gln Cys Val
            500                 505                 510
Asn Phe Asn Phe Asn Gly Leu Thr Gly Thr Gly Val Leu Thr Pro Ser
        515                 520                 525
Ser Lys Arg Phe Gln Pro Phe Gln Gln Phe Gly Arg Asp Val Ser Asp
    530                 535                 540
Phe Thr Asp Ser Val Arg Asp Pro Lys Thr Ser Glu Ile Leu Asp Ile
545                 550                 555                 560
Ser Pro Cys Ser Phe Gly Gly Val Ser Val Ile Thr Pro Gly Thr Asn
                565                 570                 575
Ala Ser Ser Glu Val Ala Val Leu Tyr Gln Asp Val Asn Cys Thr Asp
            580                 585                 590
Val Ser Thr Ala Ile His Ala Asp Gln Leu Thr Pro Ala Trp Arg Ile
        595                 600                 605
Tyr Ser Thr Gly Asn Asn Val Phe Gln Thr Gln Ala Gly Cys Leu Ile
    610                 615                 620
Gly Ala Glu His Val Asp Thr Ser Tyr Glu Cys Asp Ile Pro Ile Gly
625                 630                 635                 640
Ala Gly Ile Cys Ala Ser Tyr His Thr Val Ser Leu Leu Arg
                645                 650

<210> SEQ ID NO 10
<211> LENGTH: 222
<212> TYPE: PRT
<213> ORGANISM: SARS-CoV

<400> SEQUENCE: 10

Arg Val Val Pro Ser Gly Asp Val Val Arg Phe Pro Asn Ile Thr Asn
1               5                   10                  15
Leu Cys Pro Phe Gly Glu Val Phe Asn Ala Thr Lys Phe Pro Ser Val
            20                  25                  30
Tyr Ala Trp Glu Arg Lys Lys Ile Ser Asn Cys Val Ala Asp Tyr Ser
        35                  40                  45
Val Leu Tyr Asn Ser Thr Phe Phe Ser Thr Phe Lys Cys Tyr Gly Val
    50                  55                  60
Ser Ala Thr Lys Leu Asn Asp Leu Cys Phe Ser Asn Val Tyr Ala Asp
65                  70                  75                  80
Ser Phe Val Val Lys Gly Asp Asp Val Arg Gln Ile Ala Pro Gly Gln
                85                  90                  95
Thr Gly Val Ile Ala Asp Tyr Asn Tyr Lys Leu Pro Asp Asp Phe Met
            100                 105                 110
Gly Cys Val Leu Ala Trp Asn Thr Arg Asn Ile Asp Ala Thr Ser Thr
        115                 120                 125
Gly Asn Tyr Asn Tyr Lys Tyr Arg Tyr Leu Arg His Gly Lys Leu Arg
    130                 135                 140
```

```
Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
            165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
210                 215                 220
```

<210> SEQ ID NO 11
<211> LENGTH: 71
<212> TYPE: PRT
<213> ORGANISM: SARS-CoV

<400> SEQUENCE: 11

```
Asn Thr Arg Asn Ile Asp Ala Thr Ser Thr Gly Asn Tyr Asn Tyr Lys
1               5                   10                  15

Tyr Arg Tyr Leu Arg His Gly Lys Leu Arg Pro Phe Glu Arg Asp Ile
            20                  25                  30

Ser Asn Val Pro Phe Ser Pro Asp Gly Lys Pro Cys Thr Pro Pro Ala
        35                  40                  45

Leu Asn Cys Tyr Trp Pro Leu Asn Asp Tyr Gly Phe Tyr Thr Thr Thr
    50                  55                  60

Gly Ile Gly Tyr Gln Pro Tyr
65                  70
```

<210> SEQ ID NO 12
<211> LENGTH: 673
<212> TYPE: PRT
<213> ORGANISM: SARS-CoV-2

<400> SEQUENCE: 12

```
Ser Gln Cys Val Asn Leu Thr Thr Arg Thr Gln Leu Pro Pro Ala Tyr
1               5                   10                  15

Thr Asn Ser Phe Thr Arg Gly Val Tyr Tyr Pro Asp Lys Val Phe Arg
            20                  25                  30

Ser Ser Val Leu His Ser Thr Gln Asp Leu Phe Leu Pro Phe Phe Ser
        35                  40                  45

Asn Val Thr Trp Phe His Ala Ile His Val Ser Gly Thr Asn Gly Thr
    50                  55                  60

Lys Arg Phe Asp Asn Pro Val Leu Pro Phe Asn Asp Gly Val Tyr Phe
65                  70                  75                  80

Ala Ser Thr Glu Lys Ser Asn Ile Ile Arg Gly Trp Ile Phe Gly Thr
            85                  90                  95

Thr Leu Asp Ser Lys Thr Gln Ser Leu Leu Ile Val Asn Asn Ala Thr
        100                 105                 110

Asn Val Val Ile Lys Val Cys Glu Phe Gln Phe Cys Asn Asp Pro Phe
    115                 120                 125

Leu Gly Val Tyr His Lys Asn Asn Lys Ser Trp Met Glu Ser Glu
130                 135                 140

Phe Arg Val Tyr Ser Ser Ala Asn Asn Cys Thr Phe Glu Tyr Val Ser
145                 150                 155                 160

Gln Pro Phe Leu Met Asp Leu Glu Gly Lys Gln Gly Asn Phe Lys Asn
            165                 170                 175
```

-continued

```
Leu Arg Glu Phe Val Phe Lys Asn Ile Asp Gly Tyr Phe Lys Ile Tyr
            180                 185                 190
Ser Lys His Thr Pro Ile Asn Leu Val Arg Asp Leu Pro Gln Gly Phe
        195                 200                 205
Ser Ala Leu Glu Pro Leu Val Asp Leu Pro Ile Gly Ile Asn Ile Thr
    210                 215                 220
Arg Phe Gln Thr Leu Leu Ala Leu His Arg Ser Tyr Leu Thr Pro Gly
225                 230                 235                 240
Asp Ser Ser Ser Gly Trp Thr Ala Gly Ala Ala Ala Tyr Tyr Val Gly
                245                 250                 255
Tyr Leu Gln Pro Arg Thr Phe Leu Leu Lys Tyr Asn Glu Asn Gly Thr
            260                 265                 270
Ile Thr Asp Ala Val Asp Cys Ala Leu Asp Pro Leu Ser Glu Thr Lys
        275                 280                 285
Cys Thr Leu Lys Ser Phe Thr Val Glu Lys Gly Ile Tyr Gln Thr Ser
    290                 295                 300
Asn Phe Arg Val Gln Pro Thr Glu Ser Ile Val Arg Phe Pro Asn Ile
305                 310                 315                 320
Thr Asn Leu Cys Pro Phe Gly Glu Val Phe Asn Ala Thr Arg Phe Ala
                325                 330                 335
Ser Val Tyr Ala Trp Asn Arg Lys Arg Ile Ser Asn Cys Val Ala Asp
            340                 345                 350
Tyr Ser Val Leu Tyr Asn Ser Ala Ser Phe Ser Thr Phe Lys Cys Tyr
        355                 360                 365
Gly Val Ser Pro Thr Lys Leu Asn Asp Leu Cys Phe Thr Asn Val Tyr
    370                 375                 380
Ala Asp Ser Phe Val Ile Arg Gly Asp Glu Val Arg Gln Ile Ala Pro
385                 390                 395                 400
Gly Gln Thr Gly Lys Ile Ala Asp Tyr Asn Tyr Lys Leu Pro Asp Asp
                405                 410                 415
Phe Thr Gly Cys Val Ile Ala Trp Asn Ser Asn Asn Leu Asp Ser Lys
            420                 425                 430
Val Gly Gly Asn Tyr Asn Tyr Leu Tyr Arg Leu Phe Arg Lys Ser Asn
        435                 440                 445
Leu Lys Pro Phe Glu Arg Asp Ile Ser Thr Glu Ile Tyr Gln Ala Gly
    450                 455                 460
Ser Thr Pro Cys Asn Gly Val Glu Gly Phe Asn Cys Tyr Phe Pro Leu
465                 470                 475                 480
Gln Ser Tyr Gly Phe Gln Pro Thr Asn Gly Val Gly Tyr Gln Pro Tyr
                485                 490                 495
Arg Val Val Val Leu Ser Phe Glu Leu Leu His Ala Pro Ala Thr Val
            500                 505                 510
Cys Gly Pro Lys Lys Ser Thr Asn Leu Val Lys Asn Lys Cys Val Asn
        515                 520                 525
Phe Asn Phe Asn Gly Leu Thr Gly Thr Gly Val Leu Thr Glu Ser Asn
    530                 535                 540
Lys Lys Phe Leu Pro Phe Gln Gln Phe Gly Arg Asp Ile Ala Asp Thr
545                 550                 555                 560
Thr Asp Ala Val Arg Asp Pro Gln Thr Leu Glu Ile Leu Asp Ile Thr
                565                 570                 575
Pro Cys Ser Phe Gly Gly Val Ser Val Ile Thr Pro Gly Thr Asn Thr
            580                 585                 590
Ser Asn Gln Val Ala Val Leu Tyr Gln Asp Val Asn Cys Thr Glu Val
```

```
            595                 600                 605
Pro Val Ala Ile His Ala Asp Gln Leu Thr Pro Thr Trp Arg Val Tyr
610                 615                 620

Ser Thr Gly Ser Asn Val Phe Gln Thr Arg Ala Gly Cys Leu Ile Gly
625                 630                 635                 640

Ala Glu His Val Asn Asn Ser Tyr Glu Cys Asp Ile Pro Ile Gly Ala
                645                 650                 655

Gly Ile Cys Ala Ser Tyr Gln Thr Gln Thr Asn Ser Pro Arg Arg Ala
                660                 665                 670

Arg

<210> SEQ ID NO 13
<211> LENGTH: 223
<212> TYPE: PRT
<213> ORGANISM: SARS-CoV-2

<400> SEQUENCE: 13

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
                20                  25                  30

Tyr Ala Trp Asn Arg Lys Arg Ile Ser Asn Cys Val Ala Asp Tyr Ser
            35                  40                  45

Val Leu Tyr Asn Ser Ala Ser Phe Ser Thr Phe Lys Cys Tyr Gly Val
        50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
                100                 105                 110

Gly Cys Val Ile Ala Trp Asn Ser Asn Asn Leu Asp Ser Lys Val Gly
            115                 120                 125

Gly Asn Tyr Asn Tyr Leu Tyr Arg Leu Phe Arg Lys Ser Asn Leu Lys
        130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
                180                 185                 190

Val Val Leu Ser Phe Glu Leu Leu His Ala Pro Ala Thr Val Cys Gly
            195                 200                 205

Pro Lys Lys Ser Thr Asn Leu Val Lys Asn Lys Cys Val Asn Phe
        210                 215                 220

<210> SEQ ID NO 14
<211> LENGTH: 72
<212> TYPE: PRT
<213> ORGANISM: SARS-CoV-2

<400> SEQUENCE: 14

Asn Ser Asn Asn Leu Asp Ser Lys Val Gly Gly Asn Tyr Asn Tyr Leu
1               5                   10                  15

Tyr Arg Leu Phe Arg Lys Ser Asn Leu Lys Pro Phe Glu Arg Asp Ile
                20                  25                  30
```

```
Ser Thr Glu Ile Tyr Gln Ala Gly Ser Thr Pro Cys Asn Gly Val Glu
        35                  40                  45

Gly Phe Asn Cys Tyr Phe Pro Leu Gln Ser Tyr Gly Phe Gln Pro Thr
 50                  55                  60

Asn Gly Val Gly Tyr Gln Pro Tyr
 65                  70

<210> SEQ ID NO 15
<211> LENGTH: 805
<212> TYPE: PRT
<213> ORGANISM: Homo sapiens

<400> SEQUENCE: 15

Met Ser Ser Ser Ser Trp Leu Leu Leu Ser Leu Val Ala Val Thr Ala
 1               5                  10                  15

Ala Gln Ser Thr Ile Glu Glu Gln Ala Lys Thr Phe Leu Asp Lys Phe
             20                  25                  30

Asn His Glu Ala Glu Asp Leu Phe Tyr Gln Ser Ser Leu Ala Ser Trp
         35                  40                  45

Asn Tyr Asn Thr Asn Ile Thr Glu Glu Asn Val Gln Asn Met Asn Asn
 50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
```

```
                  325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
                355                 360                 365
Phe Leu Thr Ala His His Glu Met Gly His Ile Gln Tyr Asp Met Ala
370                 375                 380
Tyr Ala Ala Gln Pro Phe Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Gly
                435                 440                 445
Thr Leu Pro Phe Thr Tyr Met Leu Glu Lys Trp Arg Trp Met Val Phe
                450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
                500                 505                 510
Ile Arg Tyr Tyr Thr Arg Thr Leu Tyr Gln Phe Gln Phe Gln Glu Ala
                515                 520                 525
Leu Cys Gln Ala Ala Lys His Glu Gly Pro Leu His Lys Cys Asp Ile
                530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
                580                 585                 590
Thr Trp Leu Lys Asp Gln Asn Lys Asn Ser Phe Val Gly Trp Ser Thr
                595                 600                 605
Asp Trp Ser Pro Tyr Ala Asp Gln Ser Ile Lys Val Arg Ile Ser Leu
                610                 615                 620
Lys Ser Ala Leu Gly Asp Lys Ala Tyr Glu Trp Asn Asp Asn Glu Met
625                 630                 635                 640
Tyr Leu Phe Arg Ser Ser Val Ala Tyr Ala Met Arg Gln Tyr Phe Leu
                645                 650                 655
Lys Val Lys Asn Gln Met Ile Leu Phe Gly Glu Glu Asp Val Arg Val
                660                 665                 670
Ala Asn Leu Lys Pro Arg Ile Ser Phe Asn Phe Phe Val Thr Ala Pro
                675                 680                 685
Lys Asn Val Ser Asp Ile Ile Pro Arg Thr Glu Val Glu Lys Ala Ile
                690                 695                 700
Arg Met Ser Arg Ser Arg Ile Asn Asp Ala Phe Arg Leu Asn Asp Asn
705                 710                 715                 720
Ser Leu Glu Phe Leu Gly Ile Gln Pro Thr Leu Gly Pro Pro Asn Gln
                725                 730                 735
Pro Pro Val Ser Ile Trp Leu Ile Val Phe Gly Val Val Met Gly Val
                740                 745                 750
```

-continued

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
770                 775                 780

Asp Ile Ser Lys Gly Glu Asn Asn Pro Gly Phe Gln Asn Thr Asp Asp
785                 790                 795                 800

Val Gln Thr Ser Phe
            805

<210> SEQ ID NO 16
<211> LENGTH: 555
<212> TYPE: PRT
<213> ORGANISM: Homo sapiens

<400> SEQUENCE: 16

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu

```
            305                 310                 315                 320
    Pro Asn Met Thr Gln Gly Phe Trp Glu Asn Ser Met Leu Thr Asp Pro
                    325                 330                 335

Gly Asn Val Gln Lys Ala Val Cys His Pro Thr Ala Trp Asp Leu Gly
                    340                 345                 350

Lys Gly Asp Phe Arg Ile Leu Met Cys Thr Lys Val Thr Met Asp Asp
                    355                 360                 365

Phe Leu Thr Ala His His Glu Met Gly His Ile Gln Tyr Asp Met Ala
                    370                 375                 380

Tyr Ala Ala Gln Pro Phe Leu Leu Arg Asn Gly Ala Asn Glu Gly Phe
    385                 390                 395                 400

His Glu Ala Val Gly Glu Ile Met Ser Leu Ser Ala Ala Thr Pro Lys
                    405                 410                 415

His Leu Lys Ser Ile Gly Leu Leu Ser Pro Asp Phe Gln Glu Asp Asn
                    420                 425                 430

Glu Thr Glu Ile Asn Phe Leu Leu Lys Gln Ala Leu Thr Ile Val Gly
                    435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
    465                 470                 475                 480

Lys Arg Glu Ile Val Gly Val Val Glu Pro Val Pro His Asp Glu Thr
                    485                 490                 495

Tyr Cys Asp Pro Ala Ser Leu Phe His Val Ser Asn Asp Tyr Ser Phe
                    500                 505                 510

Ile Arg Tyr Tyr Thr Arg Thr Leu Tyr Gln Phe Gln Phe Gln Glu Ala
                    515                 520                 525

Leu Cys Gln Ala Ala Lys His Glu Gly Pro Leu His Lys Cys Asp Ile
                    530                 535                 540

Ser Asn Ser Thr Glu Ala Gly Gln Lys Leu Leu
    545                 550                 555

<210> SEQ ID NO 17
<211> LENGTH: 723
<212> TYPE: PRT
<213> ORGANISM: Homo sapiens

<400> SEQUENCE: 17

Gln Ser Thr Ile Glu Glu Gln Ala Lys Thr Phe Leu Asp Lys Phe Asn
    1               5                   10                  15

His Glu Ala Glu Asp Leu Phe Tyr Gln Ser Ser Leu Ala Ser Trp Asn
                    20                  25                  30

Tyr Asn Thr Asn Ile Thr Glu Glu Asn Val Gln Asn Met Asn Asn Ala
                    35                  40                  45

Gly Asp Lys Trp Ser Ala Phe Leu Lys Glu Gln Ser Thr Leu Ala Gln
                50                  55                  60

Met Tyr Pro Leu Gln Glu Ile Gln Asn Leu Thr Val Lys Leu Gln Leu
    65                  70                  75                  80

Gln Ala Leu Gln Gln Asn Gly Ser Ser Val Leu Ser Glu Asp Lys Ser
                    85                  90                  95

Lys Arg Leu Asn Thr Ile Leu Asn Thr Met Ser Thr Ile Tyr Ser Thr
                    100                 105                 110

Gly Lys Val Cys Asn Pro Asp Asn Pro Gln Glu Cys Leu Leu Leu Glu
                    115                 120                 125
```

-continued

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
                195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
    275                 280                 285

Arg Ile Phe Lys Glu Ala Glu Lys Phe Phe Val Ser Val Gly Leu Pro
290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
    355                 360                 365

Ala Ala Gln Pro Phe Leu Leu Arg Asn Gly Ala Asn Glu Gly Phe His
370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
    435                 440                 445

Gly Glu Ile Pro Lys Asp Gln Trp Met Lys Lys Trp Trp Glu Met Lys
450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
    515                 520                 525

Asn Ser Thr Glu Ala Gly Gln Lys Leu Phe Asn Met Leu Arg Leu Gly
530                 535                 540

Lys Ser Glu Pro Trp Thr Leu Ala Leu Glu Asn Val Val Gly Ala Lys 545 550 555 560

Asn Met Asn Val Arg Pro Leu Leu Asn Tyr Phe Glu Pro Leu Phe Thr
565 570 575

Trp Leu Lys Asp Gln Asn Lys Asn Ser Phe Val Gly Trp Ser Thr Asp
580 585 590

Trp Ser Pro Tyr Ala Asp Gln Ser Ile Lys Val Arg Ile Ser Leu Lys
595 600 605

Ser Ala Leu Gly Asp Lys Ala Tyr Glu Trp Asn Asp Asn Glu Met Tyr
610 615 620

Leu Phe Arg Ser Ser Val Ala Tyr Ala Met Arg Gln Tyr Phe Leu Lys
625 630 635 640

Val Lys Asn Gln Met Ile Leu Phe Gly Glu Glu Asp Val Arg Val Ala
645 650 655

Asn Leu Lys Pro Arg Ile Ser Phe Asn Phe Phe Val Thr Ala Pro Lys
660 665 670

Asn Val Ser Asp Ile Ile Pro Arg Thr Glu Val Glu Lys Ala Ile Arg
675 680 685

Met Ser Arg Ser Arg Ile Asn Asp Ala Phe Arg Leu Asn Asp Asn Ser
690 695 700

Leu Glu Phe Leu Gly Ile Gln Pro Thr Leu Gly Pro Pro Asn Gln Pro
705 710 715 720

Pro Val Ser

<210> SEQ ID NO 18
<211> LENGTH: 805
<212> TYPE: PRT
<213> ORGANISM: Rhinolophus ferrumequinum

<400> SEQUENCE: 18

Met Ser Gly Ser Ser Trp Phe Leu Leu Ser Leu Val Ala Val Thr Ala
1 5 10 15

Ala Gln Ser Thr Thr Glu Asp Leu Ala Lys Lys Phe Leu Asp Asp Phe
20 25 30

Asn Ser Glu Ala Glu Asn Leu Ser His Gln Ser Ser Leu Ala Ser Trp
35 40 45

Glu Tyr Asn Thr Asn Ile Ser Asp Glu Asn Val Gln Lys Met Asp Glu
50 55 60

Ala Gly Ala Lys Trp Ser Asp Phe Tyr Glu Lys Gln Ser Lys Leu Ala
65 70 75 80

Lys Asn Phe Ser Leu Glu Glu Ile His Asn Asp Thr Val Lys Leu Gln
85 90 95

Leu Gln Ile Leu Gln Gln Ser Gly Ser Pro Val Leu Ser Glu Asp Lys
100 105 110

Ser Lys Arg Leu Asn Ser Ile Leu Asn Ala Met Ser Thr Ile Tyr Ser
115 120 125

Thr Gly Lys Val Cys Lys Pro Asn Asn Pro Gln Glu Cys Leu Leu Leu
130 135 140

Glu Pro Gly Leu Asp Asn Ile Met Gly Thr Ser Lys Asp Tyr Asn Glu
145 150 155 160

Arg Leu Trp Ala Trp Glu Gly Trp Arg Ala Glu Val Gly Lys Gln Leu
165 170 175

Arg Pro Leu Tyr Glu Glu Tyr Val Val Leu Lys Asn Glu Met Ala Arg
180 185 190

Gly Tyr His Tyr Glu Asp Tyr Gly Asp Tyr Trp Arg Arg Asp Tyr Glu

```
            195                 200                 205
Thr Glu Gly Ser Pro Asp Leu Glu Tyr Ser Arg Asp Gln Leu Ile Lys
210                 215                 220

Asp Val Glu Arg Ile Phe Ala Glu Ile Lys Pro Leu Tyr Glu Gln Leu
225                 230                 235                 240

His Ala Tyr Val Arg Thr Lys Leu Met Asp Thr Tyr Pro Phe His Ile
            245                 250                 255

Ser Pro Thr Gly Cys Leu Pro Ala His Leu Leu Gly Asp Met Trp Gly
                260                 265                 270

Arg Phe Trp Thr Asn Leu Tyr Pro Leu Thr Val Pro Phe Gly Gln Lys
            275                 280                 285

Pro Asn Ile Asp Val Thr Asp Ala Met Leu Asn Gln Asn Trp Asp Ala
290                 295                 300

Lys Arg Ile Phe Lys Glu Ala Glu Lys Phe Leu Val Ser Ile Gly Leu
305                 310                 315                 320

Pro Asn Met Thr Glu Gly Phe Trp Asn Asn Ser Met Leu Thr Asp Pro
                325                 330                 335

Gly Asp Gly Arg Lys Val Val Cys His Pro Thr Ala Trp Asp Leu Gly
                340                 345                 350

Lys Gly Asp Phe Arg Ile Lys Met Cys Thr Lys Val Thr Met Glu Asp
            355                 360                 365

Phe Leu Thr Ala His His Glu Met Gly His Ile Gln Tyr Asp Met Ala
370                 375                 380

Tyr Ala Ser Gln Pro Tyr Leu Leu Arg Asn Gly Ala Asn Glu Gly Phe
385                 390                 395                 400

His Glu Ala Val Gly Glu Val Met Ser Leu Ser Val Ala Thr Pro Glu
                405                 410                 415

His Leu Lys Thr Met Gly Leu Leu Ser Ser Asp Phe Leu Glu Asp Asn
            420                 425                 430

Glu Thr Glu Ile Asn Phe Leu Phe Lys Gln Ala Leu Asn Ile Val Gly
            435                 440                 445

Thr Leu Pro Leu Thr Tyr Met Leu Glu Lys Trp Arg Trp Met Val Phe
450                 455                 460

Lys Gly Glu Ile Pro Lys Glu Glu Trp Met Lys Lys Trp Trp Glu Met
465                 470                 475                 480

Lys Arg Lys Ile Val Gly Val Val Glu Pro Val Pro His Asp Glu Thr
                485                 490                 495

Tyr Cys Asp Pro Ala Ser Leu Phe His Val Ala Asn Asp Tyr Ser Phe
                500                 505                 510

Ile Arg Tyr Tyr Thr Arg Thr Ile Phe Glu Phe Gln Phe His Glu Ala
            515                 520                 525

Leu Cys Arg Ile Ala Lys His Asp Gly Pro Leu His Lys Cys Gly Ile
530                 535                 540

Ser Asn Ser Thr Asp Ala Gly Glu Lys Leu His Gln Met Leu Ser Val
545                 550                 555                 560

Gly Lys Ser Gln Pro Trp Thr Ser Val Leu Lys Asp Phe Val Gly Ser
                565                 570                 575

Lys Asn Met Asp Val Gly Pro Leu Leu Arg Tyr Phe Glu Pro Leu Tyr
                580                 585                 590

Thr Trp Leu Thr Glu Gln Asn Arg Lys Ser Phe Val Gly Trp Asn Thr
            595                 600                 605

Asp Trp Ser Pro Tyr Ala Asp Gln Ser Ile Lys Val Trp Ile Ser Leu
610                 615                 620
```

Lys Ser Ala Leu Gly Glu Lys Ala Tyr Glu Trp Asn Asn Glu Met
625                 630                 635                 640

Tyr Leu Phe Arg Ser Ser Val Ala Tyr Ala Met Arg Glu Tyr Phe Leu
            645                 650                 655

Lys Thr Lys Asn Gln Thr Ile Leu Phe Gly Glu Glu Asp Val Trp Val
                660                 665                 670

Ser Asn Leu Lys Pro Arg Ile Ser Phe Asn Phe Tyr Val Thr Ser Pro
            675                 680                 685

Arg Asn Leu Ser Asp Ile Ile Pro Arg Pro Glu Val Glu Gly Ala Ile
690                 695                 700

Arg Met Ser Arg Ser Arg Ile Asn Asp Ala Phe Arg Leu Asp Asp Asn
705                 710                 715                 720

Ser Leu Glu Phe Leu Gly Ile Gln Pro Thr Leu Gly Pro Pro Tyr Gln
            725                 730                 735

Pro Pro Val Thr Ile Trp Leu Ile Val Phe Gly Val Val Met Ala Val
                740                 745                 750

Val Val Val Gly Ile Val Val Leu Ile Ile Thr Gly Ile Arg Asp Arg
            755                 760                 765

Arg Lys Lys Asp Gln Ala Arg Ser Glu Glu Asn Pro Tyr Ser Ser Val
770                 775                 780

Asp Leu Ser Lys Gly Glu Asn Asn Pro Gly Phe Gln Asn Gly Asn Asp
785                 790                 795                 800

Val Gln Thr Ser Phe
            805

<210> SEQ ID NO 19
<211> LENGTH: 723
<212> TYPE: PRT
<213> ORGANISM: Rhinolophus ferrumequinum

<400> SEQUENCE: 19

Gln Ser Thr Thr Glu Asp Leu Ala Lys Lys Phe Leu Asp Asp Phe Asn
1               5                   10                  15

Ser Glu Ala Glu Asn Leu Ser His Gln Ser Ser Leu Ala Ser Trp Glu
                20                  25                  30

Tyr Asn Thr Asn Ile Ser Asp Glu Asn Val Gln Lys Met Asp Glu Ala
            35                  40                  45

Gly Ala Lys Trp Ser Asp Phe Tyr Glu Lys Gln Ser Lys Leu Ala Lys
        50                  55                  60

Asn Phe Ser Leu Glu Glu Ile His Asn Asp Thr Val Lys Leu Gln Leu
65                  70                  75                  80

Gln Ile Leu Gln Gln Ser Gly Ser Pro Val Leu Ser Glu Asp Lys Ser
                85                  90                  95

Lys Arg Leu Asn Ser Ile Leu Asn Ala Met Ser Thr Ile Tyr Ser Thr
            100                 105                 110

Gly Lys Val Cys Lys Pro Asn Asn Pro Gln Glu Cys Leu Leu Leu Glu
        115                 120                 125

Pro Gly Leu Asp Asn Ile Met Gly Thr Ser Lys Asp Tyr Asn Glu Arg
    130                 135                 140

Leu Trp Ala Trp Glu Gly Trp Arg Ala Glu Val Gly Lys Gln Leu Arg
145                 150                 155                 160

Pro Leu Tyr Glu Glu Tyr Val Val Leu Lys Asn Glu Met Ala Arg Gly
                165                 170                 175

Tyr His Tyr Glu Asp Tyr Gly Asp Tyr Trp Arg Arg Asp Tyr Glu Thr

```
                180                 185                 190
Glu Gly Ser Pro Asp Leu Glu Tyr Ser Arg Asp Gln Leu Ile Lys Asp
            195                 200                 205

Val Glu Arg Ile Phe Ala Glu Ile Lys Pro Leu Tyr Glu Gln Leu His
        210                 215                 220

Ala Tyr Val Arg Thr Lys Leu Met Asp Thr Tyr Pro Phe His Ile Ser
225                 230                 235                 240

Pro Thr Gly Cys Leu Pro Ala His Leu Leu Gly Asp Met Trp Gly Arg
                245                 250                 255

Phe Trp Thr Asn Leu Tyr Pro Leu Thr Val Pro Phe Gly Gln Lys Pro
            260                 265                 270

Asn Ile Asp Val Thr Asp Ala Met Leu Asn Gln Asn Trp Asp Ala Lys
        275                 280                 285

Arg Ile Phe Lys Glu Ala Glu Lys Phe Leu Val Ser Ile Gly Leu Pro
    290                 295                 300

Asn Met Thr Glu Gly Phe Trp Asn Asn Ser Met Leu Thr Asp Pro Gly
305                 310                 315                 320

Asp Gly Arg Lys Val Val Cys His Pro Thr Ala Trp Asp Leu Gly Lys
                325                 330                 335

Gly Asp Phe Arg Ile Lys Met Cys Thr Lys Val Thr Met Glu Asp Phe
            340                 345                 350

Leu Thr Ala His His Glu Met Gly His Ile Gln Tyr Asp Met Ala Tyr
        355                 360                 365

Ala Ser Gln Pro Tyr Leu Leu Arg Asn Gly Ala Asn Glu Gly Phe His
    370                 375                 380

Glu Ala Val Gly Glu Val Met Ser Leu Ser Val Ala Thr Pro Glu His
385                 390                 395                 400

Leu Lys Thr Met Gly Leu Leu Ser Ser Asp Phe Leu Glu Asp Asn Glu
                405                 410                 415

Thr Glu Ile Asn Phe Leu Phe Lys Gln Ala Leu Asn Ile Val Gly Thr
            420                 425                 430

Leu Pro Leu Thr Tyr Met Leu Glu Lys Trp Arg Trp Met Val Phe Lys
        435                 440                 445

Gly Glu Ile Pro Lys Glu Glu Trp Met Lys Lys Trp Trp Glu Met Lys
    450                 455                 460

Arg Lys Ile Val Gly Val Val Glu Pro Val Pro His Asp Glu Thr Tyr
465                 470                 475                 480

Cys Asp Pro Ala Ser Leu Phe His Val Ala Asn Asp Tyr Ser Phe Ile
                485                 490                 495

Arg Tyr Tyr Thr Arg Thr Ile Phe Glu Phe Gln Phe His Glu Ala Leu
            500                 505                 510

Cys Arg Ile Ala Lys His Asp Gly Pro Leu His Lys Cys Gly Ile Ser
        515                 520                 525

Asn Ser Thr Asp Ala Gly Glu Lys Leu His Gln Met Leu Ser Val Gly
    530                 535                 540

Lys Ser Gln Pro Trp Thr Ser Val Leu Lys Asp Phe Val Gly Ser Lys
545                 550                 555                 560

Asn Met Asp Val Gly Pro Leu Leu Arg Tyr Phe Glu Pro Leu Tyr Thr
                565                 570                 575

Trp Leu Thr Glu Gln Asn Arg Lys Ser Phe Val Gly Trp Asn Thr Asp
            580                 585                 590

Trp Ser Pro Tyr Ala Asp Gln Ser Ile Lys Val Trp Ile Ser Leu Lys
        595                 600                 605
```

-continued

Ser Ala Leu Gly Glu Lys Ala Tyr Glu Trp Asn Asn Asn Glu Met Tyr
              610             615                 620

Leu Phe Arg Ser Ser Val Ala Tyr Ala Met Arg Glu Tyr Phe Leu Lys
625             630                 635                 640

Thr Lys Asn Gln Thr Ile Leu Phe Gly Glu Glu Asp Val Trp Val Ser
                645                 650                 655

Asn Leu Lys Pro Arg Ile Ser Phe Asn Phe Tyr Val Thr Ser Pro Arg
            660                 665                 670

Asn Leu Ser Asp Ile Ile Pro Arg Pro Glu Val Glu Gly Ala Ile Arg
        675                 680                 685

Met Ser Arg Ser Arg Ile Asn Asp Ala Phe Arg Leu Asp Asp Asn Ser
    690                 695                 700

Leu Glu Phe Leu Gly Ile Gln Pro Thr Leu Gly Pro Pro Tyr Gln Pro
705             710                 715                 720

Pro Val Thr

<210> SEQ ID NO 20
<211> LENGTH: 805
<212> TYPE: PRT
<213> ORGANISM: Manis javanica

<400> SEQUENCE: 20

Met Ser Gly Ser Ser Trp Leu Leu Leu Ser Leu Val Ala Val Thr Ala
1               5                   10                  15

Ala Gln Ser Thr Ser Asp Glu Glu Ala Lys Thr Phe Leu Glu Lys Phe
                20                  25                  30

Asn Ser Glu Ala Glu Glu Leu Ser Tyr Gln Ser Ser Leu Ala Ser Trp
            35                  40                  45

Asn Tyr Asn Thr Asn Ile Thr Asp Glu Asn Val Gln Lys Met Asn Val
    50                  55                  60

Ala Gly Ala Lys Trp Ser Thr Phe Tyr Glu Glu Gln Ser Lys Ile Ala
65              70                  75                  80

Lys Asn Tyr Gln Leu Gln Asn Ile Gln Asn Asp Thr Ile Lys Arg Gln
                85                  90                  95

Leu Gln Ala Leu Gln Leu Ser Gly Ser Ser Ala Leu Ser Ala Asp Lys
                100                 105                 110

Asn Gln Arg Leu Asn Thr Ile Leu Asn Thr Met Ser Thr Ile Tyr Ser
            115                 120                 125

Thr Gly Lys Val Cys Asn Pro Gly Asn Pro Gln Glu Cys Ser Leu Leu
    130                 135                 140

Glu Pro Gly Leu Asp Asn Ile Met Glu Ser Ser Lys Asp Tyr Asn Glu
145             150                 155                 160

Arg Leu Trp Ala Trp Glu Gly Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Ala Glu Gly Ala Asn Gly Tyr Asn Tyr Ser Arg Asp His Leu Ile Glu
    210                 215                 220

Asp Val Glu His Ile Phe Thr Gln Ile Lys Pro Leu Tyr Glu His Leu
225             230                 235                 240

His Ala Tyr Val Arg Ala Lys Leu Met Asp Asn Tyr Pro Ser His Ile
                245                 250                 255

```
Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Arg Gln Lys
        275                 280                 285

Pro Asn Ile Asp Val Thr Asp Ala Met Val Asn Gln Thr Trp Asp Ala
    290                 295                 300

Asn Arg Ile Phe Lys Glu Ala Glu Lys Phe Val Ser Val Gly Leu
305                 310                 315                 320

Pro Lys Met Thr Gln Thr Phe Trp Glu Asn Ser Met Leu Thr Glu Pro
                325                 330                 335

Gly Asp Gly Arg Lys Val Val Cys His Pro Thr Ala Trp Asp Leu Gly
            340                 345                 350

Lys His Asp Phe Arg Ile Lys Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Met Gln Pro Tyr Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Asn Ile Gly Leu Leu Pro Pro Asp Phe Tyr Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Ser Gly Gln Ile Pro Lys Glu Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ala Asn Asp Tyr Ser Phe
            500                 505                 510

Ile Arg Tyr Tyr Thr Arg Thr Ile Tyr Gln Phe Gln Phe Gln Glu Ala
        515                 520                 525

Leu Cys Gln Thr Ala Lys His Glu Gly Pro Leu His Lys Cys Asp Ile
    530                 535                 540

Ser Asn Ser Ala Glu Ala Gly Gln Lys Leu Leu Gln Met Leu Ser Leu
545                 550                 555                 560

Gly Lys Ser Lys Pro Trp Thr Leu Ala Leu Glu Arg Val Val Gly Thr
                565                 570                 575

Lys Asn Met Asp Val Arg Pro Leu Leu Asn Tyr Phe Glu Pro Leu Leu
            580                 585                 590

Thr Trp Leu Lys Glu Gln Asn Lys Asn Ser Phe Val Gly Trp Asn Thr
        595                 600                 605

Asp Trp Ser Pro Tyr Ala Ala Gln Ser Ile Lys Val Arg Ile Ser Leu
    610                 615                 620

Lys Ser Ala Leu Gly Glu Lys Ala Tyr Glu Trp Asn Asp Ser Glu Met
625                 630                 635                 640

Tyr Leu Phe Arg Ser Ser Val Ala Tyr Ala Met Arg Glu Tyr Phe Ser
                645                 650                 655

Lys Val Lys Lys Gln Thr Ile Pro Phe Glu Asp Glu Cys Val Arg Val
            660                 665                 670
```

```
Ser Asp Leu Lys Pro Arg Val Ser Phe Ile Phe Val Thr Leu Pro
            675                 680                 685

Lys Asn Val Ser Ala Val Ile Pro Arg Ala Glu Val Glu Glu Ala Ile
690                 695                 700

Arg Ile Ser Arg Ser Arg Ile Asn Asp Ala Phe Arg Leu Asp Asp Asn
705                 710                 715                 720

Ser Leu Glu Phe Leu Gly Ile Gln Pro Thr Leu Gln Pro Pro Tyr Gln
                725                 730                 735

Pro Pro Val Thr Ile Trp Leu Ile Val Phe Gly Val Val Met Gly Val
                740                 745                 750

Val Val Val Gly Ile Val Val Leu Ile Phe Thr Gly Ile Arg Asp Arg
                755                 760                 765

Lys Lys Lys Asp Gln Ala Arg Ser Glu Gln Asn Pro Tyr Ala Ser Val
770                 775                 780

Asp Leu Ser Lys Gly Glu Asn Asn Pro Gly Phe Gln Asn Val Asp Asp
785                 790                 795                 800

Val Gln Thr Ser Phe
                805

<210> SEQ ID NO 21
<211> LENGTH: 723
<212> TYPE: PRT
<213> ORGANISM: Manis javanica

<400> SEQUENCE: 21

Gln Ser Thr Ser Asp Glu Glu Ala Lys Thr Phe Leu Glu Lys Phe Asn
1               5                   10                  15

Ser Glu Ala Glu Glu Leu Ser Tyr Gln Ser Ser Leu Ala Ser Trp Asn
                20                  25                  30

Tyr Asn Thr Asn Ile Thr Asp Glu Asn Val Gln Lys Met Asn Val Ala
                35                  40                  45

Gly Ala Lys Trp Ser Thr Phe Tyr Glu Glu Gln Ser Lys Ile Ala Lys
            50                  55                  60

Asn Tyr Gln Leu Gln Asn Ile Gln Asn Asp Thr Ile Lys Arg Gln Leu
65              70                  75                  80

Gln Ala Leu Gln Leu Ser Gly Ser Ser Ala Leu Ser Ala Asp Lys Asn
                85                  90                  95

Gln Arg Leu Asn Thr Ile Leu Asn Thr Met Ser Thr Ile Tyr Ser Thr
                100                 105                 110

Gly Lys Val Cys Asn Pro Gly Asn Pro Gln Glu Cys Ser Leu Leu Glu
                115                 120                 125

Pro Gly Leu Asp Asn Ile Met Glu Ser Ser Lys Asp Tyr Asn Glu Arg
            130                 135                 140

Leu Trp Ala Trp Glu Gly Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Ala
                180                 185                 190

Glu Gly Ala Asn Gly Tyr Asn Tyr Ser Arg Asp His Leu Ile Glu Asp
            195                 200                 205

Val Glu His Ile Phe Thr Gln Ile Lys Pro Leu Tyr Glu His Leu His
        210                 215                 220

Ala Tyr Val Arg Ala Lys Leu Met Asp Asn Tyr Pro Ser His Ile Ser
225                 230                 235                 240
```

```
Pro Thr Gly Cys Leu Pro Ala His Leu Leu Gly Asp Met Trp Gly Arg
                245                 250                 255

Phe Trp Thr Asn Leu Tyr Pro Leu Thr Val Pro Phe Arg Gln Lys Pro
            260                 265                 270

Asn Ile Asp Val Thr Asp Ala Met Val Asn Gln Thr Trp Asp Ala Asn
        275                 280                 285

Arg Ile Phe Lys Glu Ala Glu Lys Phe Phe Val Ser Val Gly Leu Pro
    290                 295                 300

Lys Met Thr Gln Thr Phe Trp Glu Asn Ser Met Leu Thr Glu Pro Gly
305                 310                 315                 320

Asp Gly Arg Lys Val Val Cys His Pro Thr Ala Trp Asp Leu Gly Lys
                325                 330                 335

His Asp Phe Arg Ile Lys Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Met Gln Pro Tyr Leu Leu Arg Asn Gly Ala Asn Glu Gly Phe His
    370                 375                 380

Glu Ala Val Gly Glu Ile Met Ser Leu Ser Ala Ala Thr Pro Lys His
385                 390                 395                 400

Leu Lys Asn Ile Gly Leu Leu Pro Pro Asp Phe Tyr Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Ser
        435                 440                 445

Gly Gln Ile Pro Lys Glu Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ala Asn Asp Tyr Ser Phe Ile
                485                 490                 495

Arg Tyr Tyr Thr Arg Thr Ile Tyr Gln Phe Gln Phe Gln Glu Ala Leu
            500                 505                 510

Cys Gln Thr Ala Lys His Glu Gly Pro Leu His Lys Cys Asp Ile Ser
        515                 520                 525

Asn Ser Ala Glu Ala Gly Gln Lys Leu Leu Gln Met Leu Ser Leu Gly
    530                 535                 540

Lys Ser Lys Pro Trp Thr Leu Ala Leu Glu Arg Val Val Gly Thr Lys
545                 550                 555                 560

Asn Met Asp Val Arg Pro Leu Leu Asn Tyr Phe Glu Pro Leu Leu Thr
                565                 570                 575

Trp Leu Lys Glu Gln Asn Lys Asn Ser Phe Val Gly Trp Asn Thr Asp
            580                 585                 590

Trp Ser Pro Tyr Ala Ala Gln Ser Ile Lys Val Arg Ile Ser Leu Lys
        595                 600                 605

Ser Ala Leu Gly Glu Lys Ala Tyr Glu Trp Asn Asp Ser Glu Met Tyr
    610                 615                 620

Leu Phe Arg Ser Ser Val Ala Tyr Ala Met Arg Glu Tyr Phe Ser Lys
625                 630                 635                 640

Val Lys Lys Gln Thr Ile Pro Phe Glu Asp Glu Cys Val Arg Val Ser
                645                 650                 655
```

```
Asp Leu Lys Pro Arg Val Ser Phe Ile Phe Val Thr Leu Pro Lys
            660                 665                 670

Asn Val Ser Ala Val Ile Pro Arg Ala Glu Val Glu Glu Ala Ile Arg
        675                 680                 685

Ile Ser Arg Ser Arg Ile Asn Asp Ala Phe Arg Leu Asp Asp Asn Ser
    690                 695                 700

Leu Glu Phe Leu Gly Ile Gln Pro Thr Leu Gln Pro Pro Tyr Gln Pro
705                 710                 715                 720

Pro Val Thr

<210> SEQ ID NO 22
<211> LENGTH: 805
<212> TYPE: PRT
<213> ORGANISM: Paguma larvata

<400> SEQUENCE: 22

Met Ser Gly Ser Phe Trp Leu Leu Ser Phe Ala Ala Leu Thr Ala
1               5                   10                  15

Ala Gln Ser Thr Thr Glu Glu Leu Ala Lys Thr Phe Leu Glu Thr Phe
            20                  25                  30

Asn Tyr Glu Ala Gln Glu Leu Ser Tyr Gln Ser Ser Val Ala Ser Trp
        35                  40                  45

Asn Tyr Asn Thr Asn Ile Thr Asp Glu Asn Ala Lys Asn Met Asn Glu
    50                  55                  60

Ala Gly Ala Lys Trp Ser Ala Tyr Tyr Glu Glu Gln Ser Lys Leu Ala
65                  70                  75                  80

Gln Thr Tyr Pro Leu Ala Glu Ile Gln Asp Ala Lys Ile Lys Arg Gln
                85                  90                  95

Leu Gln Ala Leu Gln Gln Ser Gly Ser Ser Val Leu Ser Ala Asp Lys
            100                 105                 110

Ser Gln Arg Leu Asn Thr Ile Leu Asn Ala Met Ser Thr Ile Tyr Ser
        115                 120                 125

Thr Gly Lys Ala Cys Asn Pro Asn Asn Pro Gln Glu Cys Leu Leu Leu
    130                 135                 140

Glu Pro Gly Leu Asp Asn Ile Met Glu Asn Ser Lys Asp Tyr Asn Glu
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Ala Leu Lys Asn Glu Met Ala Arg
            180                 185                 190

Ala Asn Asn Tyr Glu Asp Tyr Gly Asp Tyr Trp Arg Gly Asp Tyr Glu
        195                 200                 205

Glu Glu Trp Thr Gly Gly Tyr Asn Tyr Ser Arg Asn Gln Leu Ile Gln
    210                 215                 220

Asp Val Glu Asp Thr Phe Glu Gln Ile Lys Pro Leu Tyr Gln His Leu
225                 230                 235                 240

His Ala Tyr Val Arg Ala Lys Leu Met Asp Thr Tyr Pro Ser Arg Ile
                245                 250                 255

Ser Arg Thr Gly Cys Leu Pro Ala His Leu Leu Gly Asp Met Trp Gly
            260                 265                 270

Arg Phe Trp Thr Asn Leu Tyr Pro Leu Thr Val Pro Phe Gly Gln Lys
        275                 280                 285

Pro Asn Ile Asp Val Thr Asp Ala Met Val Asn Gln Asn Trp Asp Ala
    290                 295                 300
```

```
Arg Arg Ile Phe Lys Glu Ala Glu Lys Phe Val Ser Val Gly Leu
305                 310                 315                 320

Pro Asn Met Thr Gln Gly Phe Trp Glu Asn Ser Met Leu Thr Glu Pro
            325                 330                 335

Gly Asp Gly Arg Lys Val Val Cys His Pro Thr Ala Trp Asp Leu Gly
            340                 345                 350

Lys Gly Asp Phe Arg Ile Lys Met Cys Thr Lys Val Thr Met Asp Asp
            355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Asn
                405                 410                 415

His Leu Lys Thr Ile Gly Leu Leu Ser Pro Ala Phe Ser Glu Asp Asn
            420                 425                 430

Glu Thr Glu Ile Asn Phe Leu Leu Lys Gln Ala Leu Thr Ile Val Gly
    435                 440                 445

Thr Leu Pro Phe Thr Tyr Met Leu Glu Lys Trp Arg Trp Met Val Phe
    450                 455                 460

Lys Gly Ala Ile Pro Lys Glu Gln Trp Met Gln Lys Trp Trp Glu Met
465                 470                 475                 480

Lys Arg Asn Ile Val Gly Val Val Glu Pro Val Pro His Asp Glu Thr
                485                 490                 495

Tyr Cys Asp Pro Ala Ser Leu Phe His Val Ala Asn Asp Tyr Ser Phe
            500                 505                 510

Ile Arg Tyr Tyr Thr Arg Thr Ile Tyr Gln Phe Gln Phe Gln Glu Ala
            515                 520                 525

Leu Cys Gln Ile Ala Lys His Glu Gly Pro Leu His Lys Cys Asp Ile
    530                 535                 540

Ser Asn Ser Thr Glu Ala Gly Lys Lys Leu Leu Glu Met Leu Ser Leu
545                 550                 555                 560

Gly Arg Ser Glu Pro Trp Thr Leu Ala Leu Glu Arg Val Val Gly Ala
                565                 570                 575

Lys Asn Met Asn Val Thr Pro Leu Leu Asn Tyr Phe Glu Pro Leu Phe
            580                 585                 590

Thr Trp Leu Lys Glu Gln Asn Arg Asn Ser Phe Val Gly Trp Asp Thr
    595                 600                 605

Asp Trp Arg Pro Tyr Ser Asp Gln Ser Ile Lys Val Arg Ile Ser Leu
    610                 615                 620

Lys Ser Ala Leu Gly Glu Lys Ala Tyr Glu Trp Asn Asp Asn Glu Met
625                 630                 635                 640

Tyr Leu Phe Arg Ser Ser Ile Ala Tyr Ala Met Arg Glu Tyr Phe Ser
                645                 650                 655

Lys Val Lys Asn Gln Thr Ile Pro Phe Val Glu Asp Asn Val Trp Val
            660                 665                 670

Ser Asp Leu Lys Pro Arg Ile Ser Phe Asn Phe Phe Val Thr Phe Ser
            675                 680                 685

Asn Asn Val Ser Asp Val Ile Pro Arg Ser Glu Val Glu Asp Ala Ile
            690                 695                 700

Arg Met Ser Arg Ser Arg Ile Asn Asp Ala Phe Arg Leu Asp Asp Asn
705                 710                 715                 720

Ser Leu Glu Phe Leu Gly Ile Glu Pro Thr Leu Ser Pro Pro Tyr Arg
```

```
              725                 730                 735
Pro Pro Val Thr Ile Trp Leu Ile Val Phe Gly Val Met Gly Ala
            740                 745                 750
Ile Val Val Gly Ile Val Leu Leu Ile Val Ser Gly Ile Arg Asn Arg
            755                 760                 765
Arg Lys Asn Asp Gln Ala Gly Ser Glu Glu Asn Pro Tyr Ala Ser Val
        770                 775                 780
Asp Leu Asn Lys Gly Glu Asn Pro Gly Phe Gln His Ala Asp Asp
785                 790                 795                 800
Val Gln Thr Ser Phe
                805

<210> SEQ ID NO 23
<211> LENGTH: 723
<212> TYPE: PRT
<213> ORGANISM: Paguma larvata

<400> SEQUENCE: 23

Gln Ser Thr Thr Glu Glu Leu Ala Lys Thr Phe Leu Glu Thr Phe Asn
1               5                   10                  15
Tyr Glu Ala Gln Glu Leu Ser Tyr Gln Ser Ser Val Ala Ser Trp Asn
                20                  25                  30
Tyr Asn Thr Asn Ile Thr Asp Glu Asn Ala Lys Asn Met Asn Glu Ala
            35                  40                  45
Gly Ala Lys Trp Ser Ala Tyr Tyr Glu Glu Gln Ser Lys Leu Ala Gln
        50                  55                  60
Thr Tyr Pro Leu Ala Glu Ile Gln Asp Ala Lys Ile Lys Arg Gln Leu
65                  70                  75                  80
Gln Ala Leu Gln Gln Ser Gly Ser Ser Val Leu Ser Ala Asp Lys Ser
                85                  90                  95
Gln Arg Leu Asn Thr Ile Leu Asn Ala Met Ser Thr Ile Tyr Ser Thr
            100                 105                 110
Gly Lys Ala Cys Asn Pro Asn Asn Pro Gln Glu Cys Leu Leu Leu Glu
        115                 120                 125
Pro Gly Leu Asp Asn Ile Met Glu Asn Ser Lys Asp Tyr Asn Glu Arg
    130                 135                 140
Leu Trp Ala Trp Glu Gly Trp Arg Ala Glu Val Gly Lys Gln Leu Arg
145                 150                 155                 160
Pro Leu Tyr Glu Glu Tyr Val Ala Leu Lys Asn Glu Met Ala Arg Ala
                165                 170                 175
Asn Asn Tyr Glu Asp Tyr Gly Asp Tyr Trp Arg Gly Asp Tyr Glu Glu
            180                 185                 190
Glu Trp Thr Gly Gly Tyr Asn Tyr Ser Arg Asn Gln Leu Ile Gln Asp
        195                 200                 205
Val Glu Asp Thr Phe Glu Gln Ile Lys Pro Leu Tyr Gln His Leu His
    210                 215                 220
Ala Tyr Val Arg Ala Lys Leu Met Asp Thr Tyr Pro Ser Arg Ile Ser
225                 230                 235                 240
Arg Thr Gly Cys Leu Pro Ala His Leu Leu Gly Asp Met Trp Gly Arg
                245                 250                 255
Phe Trp Thr Asn Leu Tyr Pro Leu Thr Val Pro Phe Gly Gln Lys Pro
            260                 265                 270
Asn Ile Asp Val Thr Asp Ala Met Val Asn Gln Asn Trp Asp Ala Arg
        275                 280                 285
```

-continued

```
Arg Ile Phe Lys Glu Ala Glu Lys Phe Phe Val Ser Val Gly Leu Pro
290                 295                 300

Asn Met Thr Gln Gly Phe Trp Glu Asn Ser Met Leu Thr Glu Pro Gly
305                 310                 315                 320

Asp Gly Arg Lys Val Val Cys His Pro Thr Ala Trp Asp Leu Gly Lys
            325                 330                 335

Gly Asp Phe Arg Ile Lys Met Cys Thr Lys Val Thr Met Asp Asp Phe
            340                 345                 350

Leu Thr Ala His His Glu Met Gly His Ile Gln Tyr Asp Met Ala Tyr
            355                 360                 365

Ala Ala Gln Pro Phe Leu Leu Arg Asn Gly Ala Asn Glu Gly Phe His
370                 375                 380

Glu Ala Val Gly Glu Ile Met Ser Leu Ser Ala Thr Pro Asn His
385                 390                 395                 400

Leu Lys Thr Ile Gly Leu Leu Ser Pro Ala Phe Ser Glu Asp Asn Glu
                405                 410                 415

Thr Glu Ile Asn Phe Leu Leu Lys Gln Ala Leu Thr Ile Val Gly Thr
                420                 425                 430

Leu Pro Phe Thr Tyr Met Leu Glu Lys Trp Arg Trp Met Val Phe Lys
            435                 440                 445

Gly Ala Ile Pro Lys Glu Gln Trp Met Gln Lys Trp Trp Glu Met Lys
450                 455                 460

Arg Asn Ile Val Gly Val Val Glu Pro Val Pro His Asp Glu Thr Tyr
465                 470                 475                 480

Cys Asp Pro Ala Ser Leu Phe His Val Ala Asn Asp Tyr Ser Phe Ile
                485                 490                 495

Arg Tyr Tyr Thr Arg Thr Ile Tyr Gln Phe Gln Phe Gln Glu Ala Leu
            500                 505                 510

Cys Gln Ile Ala Lys His Glu Gly Pro Leu His Lys Cys Asp Ile Ser
            515                 520                 525

Asn Ser Thr Glu Ala Gly Lys Lys Leu Leu Glu Met Leu Ser Leu Gly
530                 535                 540

Arg Ser Glu Pro Trp Thr Leu Ala Leu Glu Arg Val Val Gly Ala Lys
545                 550                 555                 560

Asn Met Asn Val Thr Pro Leu Leu Asn Tyr Phe Glu Pro Leu Phe Thr
                565                 570                 575

Trp Leu Lys Glu Gln Asn Arg Asn Ser Phe Val Gly Trp Asp Thr Asp
            580                 585                 590

Trp Arg Pro Tyr Ser Asp Gln Ser Ile Lys Val Arg Ile Ser Leu Lys
            595                 600                 605

Ser Ala Leu Gly Glu Lys Ala Tyr Glu Trp Asn Asp Asn Glu Met Tyr
610                 615                 620

Leu Phe Arg Ser Ser Ile Ala Tyr Ala Met Arg Glu Tyr Phe Ser Lys
625                 630                 635                 640

Val Lys Asn Gln Thr Ile Pro Phe Val Glu Asp Asn Val Trp Val Ser
                645                 650                 655

Asp Leu Lys Pro Arg Ile Ser Phe Asn Phe Phe Val Thr Phe Ser Asn
            660                 665                 670

Asn Val Ser Asp Val Ile Pro Arg Ser Glu Val Glu Asp Ala Ile Arg
            675                 680                 685

Met Ser Arg Ser Arg Ile Asn Asp Ala Phe Arg Leu Asp Asp Asn Ser
690                 695                 700

Leu Glu Phe Leu Gly Ile Glu Pro Thr Leu Ser Pro Pro Tyr Arg Pro
```

```
                705                 710                 715                 720

Pro Val Thr

<210> SEQ ID NO 24
<211> LENGTH: 805
<212> TYPE: PRT
<213> ORGANISM: Sus scrofa

<400> SEQUENCE: 24

Met Ser Gly Ser Phe Trp Leu Leu Leu Ser Leu Ile Pro Val Thr Ala
1               5                   10                  15

Ala Gln Ser Thr Thr Glu Glu Leu Ala Lys Thr Phe Leu Glu Lys Phe
            20                  25                  30

Asn Leu Glu Ala Glu Asp Leu Ala Tyr Gln Ser Ser Leu Ala Ser Trp
        35                  40                  45

Asn Tyr Asn Thr Asn Ile Thr Asp Glu Asn Ile Gln Lys Met Asn Asp
    50                  55                  60

Ala Arg Ala Lys Trp Ser Ala Phe Tyr Glu Glu Gln Ser Arg Ile Ala
65                  70                  75                  80

Lys Thr Tyr Pro Leu Asp Glu Ile Gln Thr Leu Ile Leu Lys Arg Gln
                85                  90                  95

Leu Gln Ala Leu Gln Gln Ser Gly Thr Ser Gly Leu Ser Ala Asp Lys
            100                 105                 110

Ser Lys Arg Leu Asn Thr Ile Leu Asn Thr Met Ser Thr Ile Tyr Ser
        115                 120                 125

Ser Gly Lys Val Leu Asp Pro Asn Asn Pro Gln Glu Cys Leu Val Leu
    130                 135                 140

Glu Pro Gly Leu Asp Glu Ile Met Glu Asn Ser Lys Asp Tyr Ser Arg
145                 150                 155                 160

Arg Leu Trp Ala Trp Glu Ser Trp Arg Ala Glu Val Gly Lys Gln Leu
                165                 170                 175

Arg Pro Leu Tyr Glu Glu Tyr Val Val Leu Glu Asn Glu Met Ala Arg
            180                 185                 190

Ala Asn Asn Tyr Glu Asp Tyr Gly Asp Tyr Trp Arg Gly Asp Tyr Glu
        195                 200                 205

Val Thr Gly Thr Gly Asp Tyr Asp Tyr Ser Arg Asn Gln Leu Met Glu
    210                 215                 220

Asp Val Glu Arg Thr Phe Ala Glu Ile Lys Pro Leu Tyr Glu His Leu
225                 230                 235                 240

His Ala Tyr Val Arg Ala Lys Leu Met Asp Ala Tyr Pro Ser Arg Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Gly Glu Lys
        275                 280                 285

Pro Ser Ile Asp Val Thr Glu Ala Met Val Asn Gln Ser Trp Asp Ala
    290                 295                 300

Ile Arg Ile Phe Glu Glu Ala Glu Lys Phe Phe Val Ser Ile Gly Leu
305                 310                 315                 320

Pro Asn Met Thr Gln Gly Phe Trp Asn Asn Ser Met Leu Thr Glu Pro
                325                 330                 335

Gly Asp Gly Arg Lys Val Val Cys His Pro Thr Ala Trp Asp Leu Gly
            340                 345                 350

Lys Gly Asp Phe Arg Ile Lys Met Cys Thr Lys Val Thr Met Asp Asp
```

```
                    355                 360                 365
        Phe Leu Thr Ala His His Glu Met Gly His Ile Gln Tyr Asp Met Ala
            370                 375                 380
        Tyr Ala Ile Gln Pro Tyr Leu Leu Arg Asn Gly Ala Asn Glu Gly Phe
        385                 390                 395                 400
        His Glu Ala Val Gly Glu Ile Met Ser Leu Ser Ala Ala Thr Pro His
                        405                 410                 415
        Tyr Leu Lys Ala Leu Gly Leu Leu Pro Pro Asp Phe Tyr Glu Asp Ser
                    420                 425                 430
        Glu Thr Glu Ile Asn Phe Leu Leu Lys Gln Ala Leu Thr Ile Val Gly
                        435                 440                 445
        Thr Leu Pro Phe Thr Tyr Met Leu Glu Lys Trp Arg Trp Met Val Phe
            450                 455                 460
        Lys Gly Glu Ile Pro Lys Glu Gln Trp Met Gln Lys Trp Trp Glu Met
        465                 470                 475                 480
        Lys Arg Glu Ile Val Gly Val Val Glu Pro Leu Pro His Asp Glu Thr
                        485                 490                 495
        Tyr Cys Asp Pro Ala Cys Leu Phe His Val Ala Glu Asp Tyr Ser Phe
                    500                 505                 510
        Ile Arg Tyr Tyr Thr Arg Thr Ile Tyr Gln Phe Gln Phe His Glu Ala
                        515                 520                 525
        Leu Cys Arg Thr Ala Lys His Glu Gly Pro Leu Tyr Lys Cys Asp Ile
                    530                 535                 540
        Ser Asn Ser Thr Glu Ala Gly Gln Lys Leu Leu Gln Met Leu Ser Leu
        545                 550                 555                 560
        Gly Lys Ser Glu Pro Trp Thr Leu Ala Leu Glu Asn Ile Val Gly Val
                        565                 570                 575
        Lys Thr Met Asp Val Lys Pro Leu Leu Ser Tyr Phe Glu Pro Leu Leu
                    580                 585                 590
        Thr Trp Leu Lys Ala Gln Asn Gly Asn Ser Ser Val Gly Trp Asn Thr
                    595                 600                 605
        Asp Trp Thr Pro Tyr Ala Asp Gln Ser Ile Lys Val Arg Ile Ser Leu
            610                 615                 620
        Lys Ser Ala Leu Gly Lys Glu Ala Tyr Glu Trp Asn Asp Asn Glu Met
        625                 630                 635                 640
        Tyr Leu Phe Arg Ser Ser Ile Ala Tyr Ala Met Arg Asn Tyr Phe Ser
                        645                 650                 655
        Ser Ala Lys Asn Glu Thr Ile Pro Phe Gly Ala Glu Asp Val Trp Val
                    660                 665                 670
        Ser Asp Leu Lys Pro Arg Ile Ser Phe Asn Phe Phe Val Thr Ser Pro
                    675                 680                 685
        Ala Asn Met Ser Asp Ile Ile Pro Arg Ser Asp Val Glu Lys Ala Ile
                    690                 695                 700
        Ser Met Ser Arg Ser Arg Ile Asn Asp Ala Phe Arg Leu Asp Asp Asn
        705                 710                 715                 720
        Thr Leu Glu Phe Leu Gly Ile Gln Pro Thr Leu Gly Pro Pro Asp Glu
                        725                 730                 735
        Pro Pro Val Thr Val Trp Leu Ile Ile Phe Gly Val Met Gly Leu
                    740                 745                 750
        Val Val Val Gly Ile Val Val Leu Ile Phe Thr Gly Ile Arg Asp Arg
                        755                 760                 765
        Arg Lys Lys Lys Gln Ala Ser Ser Glu Glu Asn Pro Tyr Gly Ser Met
                    770                 775                 780
```

```
Asp Leu Ser Lys Gly Glu Ser Asn Ser Gly Phe Gln Asn Gly Asp Asp
785                 790                 795                 800

Ile Gln Thr Ser Phe
            805

<210> SEQ ID NO 25
<211> LENGTH: 723
<212> TYPE: PRT
<213> ORGANISM: Sus scrofa

<400> SEQUENCE: 25

Gln Ser Thr Thr Glu Glu Leu Ala Lys Thr Phe Leu Glu Lys Phe Asn
1               5                   10                  15

Leu Glu Ala Glu Asp Leu Ala Tyr Gln Ser Ser Leu Ala Ser Trp Asn
                20                  25                  30

Tyr Asn Thr Asn Ile Thr Asp Glu Asn Ile Gln Lys Met Asn Asp Ala
            35                  40                  45

Arg Ala Lys Trp Ser Ala Phe Tyr Glu Glu Gln Ser Arg Ile Ala Lys
    50                  55                  60

Thr Tyr Pro Leu Asp Glu Ile Gln Thr Leu Ile Leu Lys Arg Gln Leu
65                  70                  75                  80

Gln Ala Leu Gln Gln Ser Gly Thr Ser Gly Leu Ser Ala Asp Lys Ser
                85                  90                  95

Lys Arg Leu Asn Thr Ile Leu Asn Thr Met Ser Thr Ile Tyr Ser Ser
            100                 105                 110

Gly Lys Val Leu Asp Pro Asn Asn Pro Gln Glu Cys Leu Val Leu Glu
        115                 120                 125

Pro Gly Leu Asp Glu Ile Met Glu Asn Ser Lys Asp Tyr Ser Arg Arg
130                 135                 140

Leu Trp Ala Trp Glu Ser Trp Arg Ala Glu Val Gly Lys Gln Leu Arg
145                 150                 155                 160

Pro Leu Tyr Glu Glu Tyr Val Val Leu Glu Asn Glu Met Ala Arg Ala
                165                 170                 175

Asn Asn Tyr Glu Asp Tyr Gly Asp Tyr Trp Arg Gly Asp Tyr Glu Val
            180                 185                 190

Thr Gly Thr Gly Asp Tyr Asp Tyr Ser Arg Asn Gln Leu Met Glu Asp
        195                 200                 205

Val Glu Arg Thr Phe Ala Glu Ile Lys Pro Leu Tyr Glu His Leu His
210                 215                 220

Ala Tyr Val Arg Ala Lys Leu Met Asp Ala Tyr Pro Ser Arg Ile Ser
225                 230                 235                 240

Pro Thr Gly Cys Leu Pro Ala His Leu Leu Gly Asp Met Trp Gly Arg
                245                 250                 255

Phe Trp Thr Asn Leu Tyr Pro Leu Thr Val Pro Phe Gly Glu Lys Pro
            260                 265                 270

Ser Ile Asp Val Thr Glu Ala Met Val Asn Gln Ser Trp Asp Ala Ile
        275                 280                 285

Arg Ile Phe Glu Glu Ala Glu Lys Phe Phe Val Ser Ile Gly Leu Pro
    290                 295                 300

Asn Met Thr Gln Gly Phe Trp Asn Asn Ser Met Leu Thr Glu Pro Gly
305                 310                 315                 320

Asp Gly Arg Lys Val Val Cys His Pro Thr Ala Trp Asp Leu Gly Lys
                325                 330                 335

Gly Asp Phe Arg Ile Lys Met Cys Thr Lys Val Thr Met Asp Asp Phe
```

```
                    340                 345                 350
Leu Thr Ala His His Glu Met Gly His Ile Gln Tyr Asp Met Ala Tyr
                355                 360                 365
Ala Ile Gln Pro Tyr Leu Leu Arg Asn Gly Ala Asn Glu Gly Phe His
            370                 375                 380
Glu Ala Val Gly Glu Ile Met Ser Leu Ser Ala Ala Thr Pro His Tyr
385                 390                 395                 400
Leu Lys Ala Leu Gly Leu Leu Pro Pro Asp Phe Tyr Glu Asp Ser Glu
                405                 410                 415
Thr Glu Ile Asn Phe Leu Leu Lys Gln Ala Leu Thr Ile Val Gly Thr
                420                 425                 430
Leu Pro Phe Thr Tyr Met Leu Glu Lys Trp Arg Trp Met Val Phe Lys
            435                 440                 445
Gly Glu Ile Pro Lys Glu Gln Trp Met Gln Lys Trp Trp Glu Met Lys
            450                 455                 460
Arg Glu Ile Val Gly Val Val Glu Pro Leu Pro His Asp Glu Thr Tyr
465                 470                 475                 480
Cys Asp Pro Ala Cys Leu Phe His Val Ala Glu Asp Tyr Ser Phe Ile
                485                 490                 495
Arg Tyr Tyr Thr Arg Thr Ile Tyr Gln Phe Gln Phe His Glu Ala Leu
                500                 505                 510
Cys Arg Thr Ala Lys His Glu Gly Pro Leu Tyr Lys Cys Asp Ile Ser
            515                 520                 525
Asn Ser Thr Glu Ala Gly Gln Lys Leu Leu Gln Met Leu Ser Leu Gly
            530                 535                 540
Lys Ser Glu Pro Trp Thr Leu Ala Leu Glu Asn Ile Val Gly Val Lys
545                 550                 555                 560
Thr Met Asp Val Lys Pro Leu Leu Ser Tyr Phe Glu Pro Leu Leu Thr
                565                 570                 575
Trp Leu Lys Ala Gln Asn Gly Asn Ser Ser Val Gly Trp Asn Thr Asp
            580                 585                 590
Trp Thr Pro Tyr Ala Asp Gln Ser Ile Lys Val Arg Ile Ser Leu Lys
            595                 600                 605
Ser Ala Leu Gly Lys Glu Ala Tyr Glu Trp Asn Asp Asn Glu Met Tyr
610                 615                 620
Leu Phe Arg Ser Ser Ile Ala Tyr Ala Met Arg Asn Tyr Phe Ser Ser
625                 630                 635                 640
Ala Lys Asn Glu Thr Ile Pro Phe Gly Ala Glu Asp Val Trp Val Ser
                645                 650                 655
Asp Leu Lys Pro Arg Ile Ser Phe Asn Phe Phe Val Thr Ser Pro Ala
            660                 665                 670
Asn Met Ser Asp Ile Ile Pro Arg Ser Asp Val Glu Lys Ala Ile Ser
            675                 680                 685
Met Ser Arg Ser Arg Ile Asn Asp Ala Phe Arg Leu Asp Asp Asn Thr
            690                 695                 700
Leu Glu Phe Leu Gly Ile Gln Pro Thr Leu Gly Pro Pro Asp Glu Pro
705                 710                 715                 720
Pro Val Thr

<210> SEQ ID NO 26
<211> LENGTH: 200
<212> TYPE: PRT
<213> ORGANISM: SARS-CoV-2
```

<400> SEQUENCE: 26

```
Pro Asn Ile Thr Asn Leu Cys Pro Phe Gly Glu Val Phe Asn Ala Thr
1               5                   10                  15

Arg Phe Ala Ser Val Tyr Ala Trp Asn Arg Lys Arg Ile Ser Asn Cys
            20                  25                  30

Val Ala Asp Tyr Ser Val Leu Tyr Asn Ser Ala Ser Phe Ser Thr Phe
        35                  40                  45

Lys Cys Tyr Gly Val Ser Pro Thr Lys Leu Asn Asp Leu Cys Phe Thr
50                  55                  60

Asn Val Tyr Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser
            195                 200
```

<210> SEQ ID NO 27
<211> LENGTH: 710
<212> TYPE: PRT
<213> ORGANISM: SARS-CoV-2

<400> SEQUENCE: 27

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Gln Cys Val Asn Leu Thr Thr Arg Thr Gln
        35                  40                  45

Leu Pro Pro Ala Tyr Thr Asn Ser Phe Thr Arg Gly Val Tyr Tyr Pro
50                  55                  60

Asp Lys Val Phe Arg Ser Ser Val Leu His Ser Thr Gln Asp Leu Phe
65                  70                  75                  80

Leu Pro Phe Phe Ser Asn Val Thr Trp Phe His Ala Ile His Val Ser
                85                  90                  95

Gly Thr Asn Gly Thr Lys Arg Phe Asp Asn Pro Val Leu Pro Phe Asn
            100                 105                 110

Asp Gly Val Tyr Phe Ala Ser Thr Glu Lys Ser Asn Ile Ile Arg Gly
        115                 120                 125

Trp Ile Phe Gly Thr Thr Leu Asp Ser Lys Thr Gln Ser Leu Leu Ile
130                 135                 140

Val Asn Asn Ala Thr Asn Val Val Ile Lys Val Cys Glu Phe Gln Phe
145                 150                 155                 160
```

```
Cys Asn Asp Pro Phe Leu Gly Val Tyr Tyr His Lys Asn Asn Lys Ser
                165                 170                 175

Trp Met Glu Ser Glu Phe Arg Val Tyr Ser Ala Asn Asn Cys Thr
        180                 185                 190

Phe Glu Tyr Val Ser Gln Pro Phe Leu Met Asp Leu Glu Gly Lys Gln
            195                 200                 205

Gly Asn Phe Lys Asn Leu Arg Glu Phe Val Phe Lys Asn Ile Asp Gly
        210                 215                 220

Tyr Phe Lys Ile Tyr Ser Lys His Thr Pro Ile Asn Leu Val Arg Asp
225                 230                 235                 240

Leu Pro Gln Gly Phe Ser Ala Leu Glu Pro Leu Val Asp Leu Pro Ile
                245                 250                 255

Gly Ile Asn Ile Thr Arg Phe Gln Thr Leu Leu Ala Leu His Arg Ser
                260                 265                 270

Tyr Leu Thr Pro Gly Asp Ser Ser Gly Trp Thr Ala Gly Ala Ala
                275                 280                 285

Ala Tyr Tyr Val Gly Tyr Leu Gln Pro Arg Thr Phe Leu Leu Lys Tyr
        290                 295                 300

Asn Glu Asn Gly Thr Ile Thr Asp Ala Val Asp Cys Ala Leu Asp Pro
305                 310                 315                 320

Leu Ser Glu Thr Lys Cys Thr Leu Lys Ser Phe Thr Val Glu Lys Gly
                325                 330                 335

Ile Tyr Gln Thr Ser Asn Phe Arg Val Gln Pro Thr Glu Ser Ile Val
                340                 345                 350

Arg Phe Pro Asn Ile Thr Asn Leu Cys Pro Phe Gly Glu Val Phe Asn
        355                 360                 365

Ala Thr Arg Phe Ala Ser Val Tyr Ala Trp Asn Arg Lys Arg Ile Ser
        370                 375                 380

Asn Cys Val Ala Asp Tyr Ser Val Leu Tyr Asn Ser Ala Ser Phe Ser
385                 390                 395                 400

Thr Phe Lys Cys Tyr Gly Val Ser Pro Thr Lys Leu Asn Asp Leu Cys
                405                 410                 415

Phe Thr Asn Val Tyr Ala Asp Ser Phe Val Ile Arg Gly Asp Glu Val
            420                 425                 430

Arg Gln Ile Ala Pro Gly Gln Thr Gly Lys Ile Ala Asp Tyr Asn Tyr
        435                 440                 445

Lys Leu Pro Asp Asp Phe Thr Gly Cys Val Ile Ala Trp Asn Ser Asn
450                 455                 460

Asn Leu Asp Ser Lys Val Gly Gly Asn Tyr Asn Tyr Leu Tyr Arg Leu
465                 470                 475                 480

Phe Arg Lys Ser Asn Leu Lys Pro Phe Glu Arg Asp Ile Ser Thr Glu
            485                 490                 495

Ile Tyr Gln Ala Gly Ser Thr Pro Cys Asn Gly Val Glu Gly Phe Asn
                500                 505                 510

Cys Tyr Phe Pro Leu Gln Ser Tyr Gly Phe Gln Pro Thr Asn Gly Val
            515                 520                 525

Gly Tyr Gln Pro Tyr Arg Val Val Val Leu Ser Phe Glu Leu Leu His
        530                 535                 540

Ala Pro Ala Thr Val Cys Gly Pro Lys Lys Ser Thr Asn Leu Val Lys
545                 550                 555                 560

Asn Lys Cys Val Asn Phe Asn Phe Asn Gly Leu Thr Gly Thr Gly Val
                565                 570                 575

Leu Thr Glu Ser Asn Lys Lys Phe Leu Pro Phe Gln Gln Phe Gly Arg
```

```
              580                 585                 590
Asp Ile Ala Asp Thr Thr Asp Ala Val Arg Asp Pro Gln Thr Leu Glu
            595                 600                 605

Ile Leu Asp Ile Thr Pro Cys Ser Phe Gly Gly Val Ser Val Ile Thr
        610                 615                 620

Pro Gly Thr Asn Thr Ser Asn Gln Val Ala Val Leu Tyr Gln Asp Val
625                 630                 635                 640

Asn Cys Thr Glu Val Pro Val Ala Ile His Ala Asp Gln Leu Thr Pro
                645                 650                 655

Thr Trp Arg Val Tyr Ser Thr Gly Ser Asn Val Phe Gln Thr Arg Ala
            660                 665                 670

Gly Cys Leu Ile Gly Ala Glu His Val Asn Asn Ser Tyr Glu Cys Asp
        675                 680                 685

Ile Pro Ile Gly Ala Gly Ile Cys Ala Ser Tyr Gln Thr Gln Thr Asn
    690                 695                 700

Ser Pro Arg Arg Ala Arg
705                 710

<210> SEQ ID NO 28
<211> LENGTH: 203
<212> TYPE: PRT
<213> ORGANISM: SARS-CoV

<400> SEQUENCE: 28

Met Asn Ile Thr Asn Leu Cys Pro Phe Gly Glu Val Phe Asn Ala Thr
1               5                   10                  15

Lys Phe Pro Ser Val Tyr Ala Trp Glu Arg Lys Lys Ile Ser Asn Cys
            20                  25                  30

Val Ala Asp Tyr Ser Val Leu Tyr Asn Ser Thr Phe Phe Ser Thr Phe
        35                  40                  45

Lys Cys Tyr Gly Val Ser Ala Thr Lys Leu Asn Asp Leu Cys Phe Ser
    50                  55                  60

Asn Val Tyr Ala Asp Ser Phe Val Val Lys Gly Asp Asp Val Arg Gln
65                  70                  75                  80

Ile Ala Pro Gly Gln Thr Gly Val Ile Ala Asp Tyr Asn Tyr Lys Leu
                85                  90                  95

Pro Asp Asp Phe Met Gly Cys Val Leu Ala Trp Asn Thr Arg Asn Ile
            100                 105                 110

Asp Ala Thr Ser Thr Gly Asn Tyr Asn Tyr Lys Tyr Arg Tyr Leu Arg
        115                 120                 125

His Gly Lys Leu Arg Pro Phe Glu Arg Asp Ile Ser Asn Val Pro Phe
    130                 135                 140

Ser Pro Asp Gly Lys Pro Cys Thr Pro Pro Ala Leu Asn Cys Tyr Trp
145                 150                 155                 160

Pro Leu Asn Asp Tyr Gly Phe Tyr Thr Thr Thr Gly Ile Gly Tyr Gln
                165                 170                 175

Pro Tyr Arg Val Val Val Leu Ser Phe Glu Leu Leu Asn Ala Pro Ala
            180                 185                 190

Thr Tyr Leu Ser Leu Asn Thr Ala Ala Ala Leu
        195                 200

<210> SEQ ID NO 29
<211> LENGTH: 805
<212> TYPE: PRT
<213> ORGANISM: Homo sapiens
```

<400> SEQUENCE: 29

```
Met Ser Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

```
His Leu Lys Ser Ile Gly Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
        530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Gln Ser Ile Lys Val Arg Ile Ser Leu
        610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Asp Val Arg Val
                660                 665                 670

Ala Asn Leu Lys Pro Arg Ile Ser Phe Asn Phe Phe Val Thr Ala Pro
            675                 680                 685

Lys Asn Val Ser Asp Ile Ile Pro Arg Thr Glu Val Glu Lys Ala Ile
        690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
            755                 760                 765

Lys Lys Lys Asn Lys Ala Arg Ser Gly Glu Asn Pro Tyr Ala Ser Ile
        770                 775                 780

Asp Ile Ser Lys Gly Glu Asn Asn Pro Gly Phe Gln Asn Thr Asp Asp
785                 790                 795                 800

Val Gln Thr Ser Phe
                805

<210> SEQ ID NO 30
<211> LENGTH: 723
```

<212> TYPE: PRT
<213> ORGANISM: Homo sapiens

<400> SEQUENCE: 30

Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
370                 375                 380

Glu Ala Val Gly Glu Ile Met Ser Leu Ser Ala Ala Thr Pro Lys His
385                 390                 395                 400

-continued

```
Leu Lys Ser Ile Gly Leu Leu Ser Pro Asp Phe Gln Glu Asp Asn Glu
                405                 410                 415
Thr Glu Ile Asn Phe Leu Leu Lys Gln Ala Leu Thr Ile Val Gly Thr
            420                 425                 430
Leu Pro Phe Thr Tyr Met Leu Glu Lys Trp Arg Trp Met Val Phe Lys
        435                 440                 445
Gly Glu Ile Pro Lys Asp Gln Trp Met Lys Lys Trp Trp Glu Met Lys
    450                 455                 460
Arg Glu Ile Val Gly Val Val Glu Pro Val Pro His Asp Glu Thr Tyr
465                 470                 475                 480
Cys Asp Pro Ala Ser Leu Phe His Val Ser Asn Asp Tyr Ser Phe Ile
                485                 490                 495
Arg Tyr Tyr Thr Arg Thr Leu Tyr Gln Phe Gln Phe Gln Glu Ala Leu
            500                 505                 510
Cys Gln Ala Ala Lys His Glu Gly Pro Leu His Lys Cys Asp Ile Ser
        515                 520                 525
Asn Ser Thr Glu Ala Gly Gln Lys Leu Phe Asn Met Leu Arg Leu Gly
    530                 535                 540
Lys Ser Glu Pro Trp Thr Leu Ala Leu Glu Asn Val Val Gly Ala Lys
545                 550                 555                 560
Asn Met Asn Val Arg Pro Leu Leu Asn Tyr Phe Glu Pro Leu Phe Thr
                565                 570                 575
Trp Leu Lys Asp Gln Asn Lys Asn Ser Phe Val Gly Trp Ser Thr Asp
            580                 585                 590
Trp Ser Pro Tyr Ala Asp Gln Ser Ile Lys Val Arg Ile Ser Leu Lys
        595                 600                 605
Ser Ala Leu Gly Asp Arg Ala Tyr Glu Trp Asn Asp Asn Glu Met Tyr
    610                 615                 620
Leu Phe Arg Ser Ser Val Ala Tyr Ala Met Arg Gln Tyr Phe Leu Lys
625                 630                 635                 640
Val Lys Asn Gln Met Ile Leu Phe Gly Glu Glu Asp Val Arg Val Ala
                645                 650                 655
Asn Leu Lys Pro Arg Ile Ser Phe Asn Phe Phe Val Thr Ala Pro Lys
            660                 665                 670
Asn Val Ser Asp Ile Ile Pro Arg Thr Glu Val Glu Lys Ala Ile Arg
        675                 680                 685
Met Ser Arg Ser Arg Ile Asn Asp Ala Phe Arg Leu Asn Asp Asn Ser
    690                 695                 700
Leu Glu Phe Leu Gly Ile Gln Pro Thr Leu Gly Pro Pro Asn Gln Pro
705                 710                 715                 720
Pro Val Ser
```

<210> SEQ ID NO 31
<211> LENGTH: 805
<212> TYPE: PRT
<213> ORGANISM: Rhinolophus sinicus

<400> SEQUENCE: 31

```
Met Ser Ser Ser Ser Trp Leu Leu Leu Ser Leu Val Ala Val Thr Thr
1               5                   10                  15
Ala Gln Phe Thr Thr Glu Asp Leu Ala Lys Ile Phe Leu Asp Glu Phe
            20                  25                  30
Asn Ser Glu Ala Glu Asn Leu Ser Tyr Gln Ser Ser Leu Ala Ser Trp
        35                  40                  45
```

```
Asp Tyr Asn Thr Asn Ile Asn Asp Glu Asn Val Gln Lys Met Asp Glu
 50                  55                  60

Ala Gly Ala Lys Trp Ser Ala Phe Tyr Glu Glu Gln Ser Lys Leu Ala
 65                  70                  75                  80

Lys Asn Tyr Pro Leu Glu Gln Ile Gln Asn Val Thr Val Lys Leu Gln
                 85                  90                  95

Leu Gln Ile Leu Gln Gln Ser Gly Ser Pro Val Leu Ser Glu Asp Lys
            100                 105                 110

Ser Lys Arg Leu Asn Ser Ile Leu Asn Ala Met Ser Thr Ile Tyr Ser
        115                 120                 125

Thr Gly Lys Val Cys Lys Pro Asn Lys Pro His Glu Cys Leu Leu Leu
    130                 135                 140

Glu Pro Gly Leu Asp Asn Ile Met Gly Thr Ser Lys Asp Tyr Ser Glu
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Val Leu Lys Asn Glu Met Ala Arg
            180                 185                 190

Gly Tyr His Tyr Glu Asp Tyr Gly Asp Tyr Trp Arg Arg Asp Tyr Glu
        195                 200                 205

Thr Glu Glu Ser Pro Gly Pro Gly Tyr Ser Arg Asp Gln Leu Met Lys
    210                 215                 220

Asp Val Glu Arg Ile Phe Thr Glu Ile Lys Pro Leu Tyr Glu His Leu
225                 230                 235                 240

His Ala Tyr Val Arg Ala Lys Leu Met Asp Thr Tyr Pro Phe His Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Gly Gln Lys
        275                 280                 285

Pro Asn Ile Asp Val Thr Asp Glu Met Leu Lys Gln Gly Trp Asp Ala
    290                 295                 300

Asp Arg Ile Phe Lys Glu Ala Glu Lys Phe Phe Val Ser Val Gly Leu
305                 310                 315                 320

Pro Asn Met Thr Glu Gly Phe Trp Asn Asn Ser Met Leu Thr Glu Pro
                325                 330                 335

Gly Asp Gly Arg Lys Val Val Cys His Pro Thr Ala Trp Asp Leu Gly
            340                 345                 350

Lys Gly Asp Phe Arg Ile Lys Met Cys Thr Lys Val Thr Met Glu Asp
        355                 360                 365

Phe Leu Thr Ala His His Glu Met Gly His Ile Gln Tyr Asp Met Ala
    370                 375                 380

Tyr Ala Ser Gln Pro Tyr Leu Leu Arg Asn Gly Ala Asn Glu Gly Phe
385                 390                 395                 400

His Glu Ala Val Gly Glu Val Met Ser Leu Ser Val Ala Thr Pro Lys
                405                 410                 415

His Leu Lys Thr Met Gly Leu Leu Ser Pro Asp Phe Arg Glu Asp Asn
            420                 425                 430

Glu Thr Glu Ile Asn Phe Leu Leu Lys Gln Ala Leu Asn Ile Val Gly
        435                 440                 445

Thr Leu Pro Phe Thr Tyr Met Leu Glu Lys Trp Arg Trp Met Val Phe
    450                 455                 460
```

```
Lys Gly Glu Ile Pro Lys Glu Glu Trp Met Lys Trp Trp Glu Met
465                 470                 475                 480

Lys Arg Lys Ile Val Gly Val Val Glu Pro Val Pro His Asp Glu Thr
                485                 490                 495

Tyr Cys Asp Pro Ala Ser Leu Phe His Val Ala Asn Asp Tyr Ser Phe
            500                 505                 510

Ile Arg Tyr Tyr Thr Arg Thr Ile Phe Glu Phe Gln Phe His Glu Ala
        515                 520                 525

Leu Cys Arg Ile Ala Gln His Asp Gly Pro Leu His Lys Cys Asp Ile
530                 535                 540

Ser Asn Ser Thr Asp Ala Gly Lys Lys Leu His Gln Met Leu Ser Val
545                 550                 555                 560

Gly Lys Ser Gln Ala Trp Thr Lys Thr Leu Glu Asp Ile Val Asp Ser
                565                 570                 575

Arg Asn Met Asp Val Gly Pro Leu Leu Arg Tyr Phe Glu Pro Leu Tyr
            580                 585                 590

Thr Trp Leu Gln Glu Gln Asn Arg Lys Ser Tyr Val Gly Trp Asn Thr
        595                 600                 605

Asp Trp Ser Pro Tyr Ser Asp Gln Ser Ile Lys Val Arg Ile Ser Leu
610                 615                 620

Lys Ser Ala Leu Gly Glu Asn Ala Tyr Glu Trp Asn Asp Asn Glu Met
625                 630                 635                 640

Tyr Leu Phe Arg Ser Ser Val Ala Tyr Ala Met Arg Glu Tyr Phe Leu
                645                 650                 655

Lys Glu Lys His Gln Thr Ile Leu Phe Gly Ala Glu Asn Val Trp Val
            660                 665                 670

Ser Asn Leu Lys Pro Arg Ile Ser Phe Asn Phe His Val Thr Ser Pro
        675                 680                 685

Gly Asn Leu Ser Asp Ile Ile Pro Arg Pro Glu Val Glu Gly Ala Ile
690                 695                 700

Arg Met Ser Arg Ser Arg Ile Asn Asp Ala Phe Arg Leu Asp Asp Asn
705                 710                 715                 720

Ser Leu Glu Phe Leu Gly Ile Gln Pro Thr Leu Gly Pro Pro Tyr Gln
                725                 730                 735

Pro Pro Val Thr Ile Trp Leu Ile Val Phe Gly Val Val Met Ala Val
            740                 745                 750

Val Val Val Gly Ile Val Val Leu Ile Ile Thr Gly Ile Arg Asp Arg
        755                 760                 765

Arg Lys Thr Asp Gln Ala Arg Ser Glu Glu Asn Pro Tyr Ser Ser Val
770                 775                 780

Asp Leu Ser Lys Gly Glu Asn Asn Pro Gly Phe Gln Asn Gly Asp Asp
785                 790                 795                 800

Val Gln Thr Ser Phe
                805

<210> SEQ ID NO 32
<211> LENGTH: 723
<212> TYPE: PRT
<213> ORGANISM: Rhinolophus sinicus

<400> SEQUENCE: 32

Gln Phe Thr Thr Glu Asp Leu Ala Lys Ile Phe Leu Asp Glu Phe Asn
1               5                   10                  15

Ser Glu Ala Glu Asn Leu Ser Tyr Gln Ser Ser Leu Ala Ser Trp Asp
            20                  25                  30
```

```
Tyr Asn Thr Asn Ile Asn Asp Glu Asn Val Gln Lys Met Asp Glu Ala
         35                  40                  45
Gly Ala Lys Trp Ser Ala Phe Tyr Glu Glu Gln Ser Lys Leu Ala Lys
 50                  55                  60
Asn Tyr Pro Leu Glu Gln Ile Gln Asn Val Thr Val Lys Leu Gln Leu
 65                  70                  75                  80
Gln Ile Leu Gln Gln Ser Gly Ser Pro Val Leu Ser Glu Asp Lys Ser
                 85                  90                  95
Lys Arg Leu Asn Ser Ile Leu Asn Ala Met Ser Thr Ile Tyr Ser Thr
                100                 105                 110
Gly Lys Val Cys Lys Pro Asn Lys Pro His Glu Cys Leu Leu Leu Glu
            115                 120                 125
Pro Gly Leu Asp Asn Ile Met Gly Thr Ser Lys Asp Tyr Ser Glu Arg
        130                 135                 140
Leu Trp Ala Trp Glu Gly Trp Arg Ala Glu Val Gly Lys Gln Leu Arg
145                 150                 155                 160
Pro Leu Tyr Glu Glu Tyr Val Val Leu Lys Asn Glu Met Ala Arg Gly
                165                 170                 175
Tyr His Tyr Glu Asp Tyr Gly Asp Tyr Trp Arg Arg Asp Tyr Glu Thr
            180                 185                 190
Glu Glu Ser Pro Gly Pro Gly Tyr Ser Arg Asp Gln Leu Met Lys Asp
        195                 200                 205
Val Glu Arg Ile Phe Thr Glu Ile Lys Pro Leu Tyr Glu His Leu His
210                 215                 220
Ala Tyr Val Arg Ala Lys Leu Met Asp Thr Tyr Pro Phe His Ile Ser
225                 230                 235                 240
Pro Thr Gly Cys Leu Pro Ala His Leu Leu Gly Asp Met Trp Gly Arg
                245                 250                 255
Phe Trp Thr Asn Leu Tyr Pro Leu Thr Val Pro Phe Gly Gln Lys Pro
            260                 265                 270
Asn Ile Asp Val Thr Asp Glu Met Leu Lys Gln Gly Trp Asp Ala Asp
        275                 280                 285
Arg Ile Phe Lys Glu Ala Glu Lys Phe Phe Val Ser Val Gly Leu Pro
290                 295                 300
Asn Met Thr Glu Gly Phe Trp Asn Asn Ser Met Leu Thr Glu Pro Gly
305                 310                 315                 320
Asp Gly Arg Lys Val Val Cys His Pro Thr Ala Trp Asp Leu Gly Lys
                325                 330                 335
Gly Asp Phe Arg Ile Lys Met Cys Thr Lys Val Thr Met Glu Asp Phe
            340                 345                 350
Leu Thr Ala His His Glu Met Gly His Ile Gln Tyr Asp Met Ala Tyr
        355                 360                 365
Ala Ser Gln Pro Tyr Leu Leu Arg Asn Gly Ala Asn Glu Gly Phe His
370                 375                 380
Glu Ala Val Gly Glu Val Met Ser Leu Ser Val Ala Thr Pro Lys His
385                 390                 395                 400
Leu Lys Thr Met Gly Leu Leu Ser Pro Asp Phe Arg Glu Asp Asn Glu
                405                 410                 415
Thr Glu Ile Asn Phe Leu Leu Lys Gln Ala Leu Asn Ile Val Gly Thr
            420                 425                 430
Leu Pro Phe Thr Tyr Met Leu Glu Lys Trp Arg Trp Met Val Phe Lys
        435                 440                 445
```

```
Gly Glu Ile Pro Lys Glu Glu Trp Met Lys Lys Trp Trp Glu Met Lys
450                 455                 460

Arg Lys Ile Val Gly Val Val Glu Pro Val Pro His Asp Glu Thr Tyr
465                 470                 475                 480

Cys Asp Pro Ala Ser Leu Phe His Val Ala Asn Asp Tyr Ser Phe Ile
                485                 490                 495

Arg Tyr Tyr Thr Arg Thr Ile Phe Glu Phe Gln Phe His Glu Ala Leu
                500                 505                 510

Cys Arg Ile Ala Gln His Asp Gly Pro Leu His Lys Cys Asp Ile Ser
                515                 520                 525

Asn Ser Thr Asp Ala Gly Lys Lys Leu His Gln Met Leu Ser Val Gly
                530                 535                 540

Lys Ser Gln Ala Trp Thr Lys Thr Leu Glu Asp Ile Val Asp Ser Arg
545                 550                 555                 560

Asn Met Asp Val Gly Pro Leu Leu Arg Tyr Phe Glu Pro Leu Tyr Thr
                565                 570                 575

Trp Leu Gln Glu Gln Asn Arg Lys Ser Tyr Val Gly Trp Asn Thr Asp
                580                 585                 590

Trp Ser Pro Tyr Ser Asp Gln Ser Ile Lys Val Arg Ile Ser Leu Lys
                595                 600                 605

Ser Ala Leu Gly Glu Asn Ala Tyr Glu Trp Asn Asp Asn Glu Met Tyr
610                 615                 620

Leu Phe Arg Ser Ser Val Ala Tyr Ala Met Arg Glu Tyr Phe Leu Lys
625                 630                 635                 640

Glu Lys His Gln Thr Ile Leu Phe Gly Ala Glu Asn Val Trp Val Ser
                645                 650                 655

Asn Leu Lys Pro Arg Ile Ser Phe Asn Phe His Val Thr Ser Pro Gly
                660                 665                 670

Asn Leu Ser Asp Ile Ile Pro Arg Pro Glu Val Glu Gly Ala Ile Arg
                675                 680                 685

Met Ser Arg Ser Arg Ile Asn Asp Ala Phe Arg Leu Asp Asp Asn Ser
690                 695                 700

Leu Glu Phe Leu Gly Ile Gln Pro Thr Leu Gly Pro Pro Tyr Gln Pro
705                 710                 715                 720

Pro Val Thr
```

<210> SEQ ID NO 33
<211> LENGTH: 805
<212> TYPE: PRT
<213> ORGANISM: Sus scrofa

<400> SEQUENCE: 33

```
Met Ser Gly Ser Phe Trp Leu Leu Leu Ser Leu Ile Pro Val Thr Ala
1               5                   10                  15

Ala Gln Ser Thr Thr Glu Glu Leu Ala Lys Thr Phe Leu Glu Lys Phe
                20                  25                  30

Asn Leu Glu Ala Glu Asp Leu Ala Tyr Gln Ser Ser Leu Ala Ser Trp
            35                  40                  45

Thr Ile Asn Thr Asn Ile Thr Asp Glu Asn Ile Gln Lys Met Asn Asp
        50                  55                  60

Ala Arg Ala Lys Trp Ser Ala Phe Tyr Glu Glu Ser Arg Ile Ala
65                  70                  75                  80

Lys Thr Tyr Pro Leu Asp Glu Ile Gln Thr Leu Ile Leu Lys Arg Gln
                85                  90                  95
```

```
Leu Gln Ala Leu Gln Gln Ser Gly Thr Ser Gly Leu Ser Ala Asp Lys
            100                 105                 110

Ser Lys Arg Leu Asn Thr Ile Leu Asn Thr Met Ser Thr Ile Tyr Ser
        115                 120                 125

Ser Gly Lys Val Leu Asp Pro Asn Asn Pro Gln Glu Cys Leu Val Leu
130                 135                 140

Glu Pro Gly Leu Asp Glu Ile Met Glu Asn Ser Lys Asp Tyr Ser Arg
145                 150                 155                 160

Arg Leu Trp Ala Trp Glu Ser Trp Arg Ala Glu Val Gly Lys Gln Leu
                165                 170                 175

Arg Pro Leu Tyr Glu Glu Tyr Val Val Leu Glu Asn Glu Met Ala Arg
            180                 185                 190

Ala Asn Asn Tyr Glu Asp Tyr Gly Asp Tyr Trp Arg Gly Asp Tyr Glu
        195                 200                 205

Val Thr Gly Thr Gly Asp Tyr Asp Tyr Ser Arg Asn Gln Leu Met Glu
210                 215                 220

Asp Val Glu Arg Thr Phe Ala Glu Ile Lys Pro Leu Tyr Glu His Leu
225                 230                 235                 240

His Ala Tyr Val Arg Ala Lys Leu Met Asp Ala Tyr Pro Ser Arg Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Gly Glu Lys
        275                 280                 285

Pro Ser Ile Asp Val Thr Glu Ala Met Val Asn Gln Ser Trp Asp Ala
290                 295                 300

Ile Arg Ile Phe Glu Glu Ala Glu Lys Phe Phe Val Ser Ile Gly Leu
305                 310                 315                 320

Pro Asn Met Thr Gln Gly Phe Trp Asn Asn Ser Met Leu Thr Glu Pro
                325                 330                 335

Gly Asp Gly Arg Lys Val Val Cys His Pro Thr Ala Trp Asp Leu Gly
            340                 345                 350

Lys Gly Asp Phe Arg Ile Lys Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ile Gln Pro Tyr Leu Leu Arg Asn Gly Ala Asn Glu Gly Phe
385                 390                 395                 400

His Glu Ala Val Gly Glu Ile Met Ser Leu Ser Ala Ala Thr Pro His
                405                 410                 415

Tyr Leu Lys Ala Leu Gly Leu Leu Pro Pro Asp Phe Tyr Glu Asp Ser
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Glu Gln Trp Met Gln Lys Trp Trp Glu Met
465                 470                 475                 480

Lys Arg Glu Ile Val Gly Val Val Glu Pro Leu Pro His Asp Glu Thr
                485                 490                 495

Tyr Cys Asp Pro Ala Cys Leu Phe His Val Ala Glu Asp Tyr Ser Phe
            500                 505                 510

Ile Arg Tyr Tyr Thr Arg Thr Ile Tyr Gln Phe Gln Phe His Glu Ala
```

515                 520                 525
Leu Cys Arg Thr Ala Lys His Glu Gly Pro Leu Tyr Lys Cys Asp Ile
530                 535                 540

Ser Asn Ser Thr Glu Ala Gly Gln Lys Leu Leu Gln Met Leu Ser Leu
545                 550                 555                 560

Gly Lys Ser Glu Pro Trp Thr Leu Ala Leu Glu Asn Ile Val Gly Val
                565                 570                 575

Lys Thr Met Asp Val Lys Pro Leu Leu Ser Tyr Phe Glu Pro Leu Leu
            580                 585                 590

Thr Trp Leu Lys Ala Gln Asn Gly Asn Ser Ser Val Gly Trp Asn Thr
        595                 600                 605

Asp Trp Thr Pro Tyr Ala Asp Gln Ser Ile Lys Val Arg Ile Ser Leu
610                 615                 620

Lys Ser Ala Leu Gly Glu Asp Ala Tyr Glu Trp Asn Asp Asn Glu Met
625                 630                 635                 640

Tyr Leu Phe Arg Ser Ser Ile Ala Tyr Ala Met Arg Asn Tyr Phe Ser
                645                 650                 655

Ser Ala Lys Asn Glu Thr Ile Pro Phe Gly Ala Val Asp Val Trp Val
            660                 665                 670

Ser Asp Leu Lys Pro Arg Ile Ser Phe Asn Phe Val Thr Ser Pro
        675                 680                 685

Ala Asn Met Ser Asp Ile Ile Pro Arg Ser Asp Val Glu Lys Ala Ile
690                 695                 700

Ser Met Ser Arg Ser Arg Ile Asn Asp Ala Phe Arg Leu Asp Asp Asn
705                 710                 715                 720

Thr Leu Glu Phe Leu Gly Ile Gln Pro Thr Leu Gly Pro Pro Asp Glu
                725                 730                 735

Pro Pro Val Thr Val Trp Leu Ile Ile Phe Gly Val Val Met Gly Leu
            740                 745                 750

Val Val Val Gly Ile Val Val Leu Ile Phe Thr Gly Ile Arg Asp Arg
        755                 760                 765

Arg Lys Lys Lys Gln Ala Ser Ser Glu Glu Asn Pro Tyr Gly Ser Met
770                 775                 780

Asp Leu Ser Lys Gly Glu Ser Asn Ser Gly Phe Gln Asn Gly Asp Asp
785                 790                 795                 800

Ile Gln Thr Ser Phe
                805

<210> SEQ ID NO 34
<211> LENGTH: 723
<212> TYPE: PRT
<213> ORGANISM: Sus scrofa

<400> SEQUENCE: 34

Gln Ser Thr Thr Glu Glu Leu Ala Lys Thr Phe Leu Glu Lys Phe Asn
1               5                   10                  15

Leu Glu Ala Glu Asp Leu Ala Tyr Gln Ser Ser Leu Ala Ser Trp Thr
            20                  25                  30

Ile Asn Thr Asn Ile Thr Asp Glu Asn Ile Gln Lys Met Asn Asp Ala
        35                  40                  45

Arg Ala Lys Trp Ser Ala Phe Tyr Glu Glu Gln Ser Arg Ile Ala Lys
    50                  55                  60

Thr Tyr Pro Leu Asp Glu Ile Gln Thr Leu Ile Leu Lys Arg Gln Leu
65                  70                  75                  80

Gln Ala Leu Gln Gln Ser Gly Thr Ser Gly Leu Ser Ala Asp Lys Ser
                85                  90                  95

Lys Arg Leu Asn Thr Ile Leu Asn Thr Met Ser Thr Ile Tyr Ser Ser
            100                 105                 110

Gly Lys Val Leu Asp Pro Asn Pro Gln Glu Cys Leu Val Leu Glu
            115                 120                 125

Pro Gly Leu Asp Glu Ile Met Glu Asn Ser Lys Asp Tyr Ser Arg Arg
            130                 135                 140

Leu Trp Ala Trp Glu Ser Trp Arg Ala Glu Val Gly Lys Gln Leu Arg
145                 150                 155                 160

Pro Leu Tyr Glu Glu Tyr Val Val Leu Glu Asn Glu Met Ala Arg Ala
                165                 170                 175

Asn Asn Tyr Glu Asp Tyr Gly Asp Tyr Trp Arg Gly Asp Tyr Glu Val
            180                 185                 190

Thr Gly Thr Gly Asp Tyr Asp Tyr Ser Arg Asn Gln Leu Met Glu Asp
            195                 200                 205

Val Glu Arg Thr Phe Ala Glu Ile Lys Pro Leu Tyr Glu His Leu His
    210                 215                 220

Ala Tyr Val Arg Ala Lys Leu Met Asp Ala Tyr Pro Ser Arg Ile Ser
225                 230                 235                 240

Pro Thr Gly Cys Leu Pro Ala His Leu Leu Gly Asp Met Trp Gly Arg
                245                 250                 255

Phe Trp Thr Asn Leu Tyr Pro Leu Thr Val Pro Phe Gly Glu Lys Pro
                260                 265                 270

Ser Ile Asp Val Thr Glu Ala Met Val Asn Gln Ser Trp Asp Ala Ile
            275                 280                 285

Arg Ile Phe Glu Glu Ala Glu Lys Phe Phe Val Ser Ile Gly Leu Pro
            290                 295                 300

Asn Met Thr Gln Gly Phe Trp Asn Asn Ser Met Leu Thr Glu Pro Gly
305                 310                 315                 320

Asp Gly Arg Lys Val Val Cys His Pro Thr Ala Trp Asp Leu Gly Lys
                325                 330                 335

Gly Asp Phe Arg Ile Lys Met Cys Thr Lys Val Thr Met Asp Asp Phe
            340                 345                 350

Leu Thr Ala His His Glu Met Gly His Ile Gln Tyr Asp Met Ala Tyr
            355                 360                 365

Ala Ile Gln Pro Tyr Leu Leu Arg Asn Gly Ala Asn Glu Gly Phe His
            370                 375                 380

Glu Ala Val Gly Glu Ile Met Ser Leu Ser Ala Ala Thr Pro His Tyr
385                 390                 395                 400

Leu Lys Ala Leu Gly Leu Leu Pro Pro Asp Phe Tyr Glu Asp Ser Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
            435                 440                 445

Gly Glu Ile Pro Lys Glu Gln Trp Met Gln Lys Trp Trp Glu Met Lys
            450                 455                 460

Arg Glu Ile Val Gly Val Glu Pro Leu Pro His Asp Glu Thr Tyr
465                 470                 475                 480

Cys Asp Pro Ala Cys Leu Phe His Val Ala Glu Asp Tyr Ser Phe Ile
                485                 490                 495

Arg Tyr Tyr Thr Arg Thr Ile Tyr Gln Phe Gln Phe His Glu Ala Leu

-continued

```
                500                 505                 510
Cys Arg Thr Ala Lys His Glu Gly Pro Leu Tyr Lys Cys Asp Ile Ser
        515                 520                 525

Asn Ser Thr Glu Ala Gly Gln Lys Leu Leu Gln Met Leu Ser Leu Gly
        530                 535                 540

Lys Ser Glu Pro Trp Thr Leu Ala Leu Glu Asn Ile Val Gly Val Lys
545                 550                 555                 560

Thr Met Asp Val Lys Pro Leu Leu Ser Tyr Phe Glu Pro Leu Leu Thr
                565                 570                 575

Trp Leu Lys Ala Gln Asn Gly Asn Ser Ser Val Gly Trp Asn Thr Asp
            580                 585                 590

Trp Thr Pro Tyr Ala Asp Gln Ser Ile Lys Val Arg Ile Ser Leu Lys
        595                 600                 605

Ser Ala Leu Gly Glu Asp Ala Tyr Glu Trp Asn Asp Asn Glu Met Tyr
    610                 615                 620

Leu Phe Arg Ser Ser Ile Ala Tyr Ala Met Arg Asn Tyr Phe Ser Ser
625                 630                 635                 640

Ala Lys Asn Glu Thr Ile Pro Phe Gly Ala Val Asp Val Trp Val Ser
                645                 650                 655

Asp Leu Lys Pro Arg Ile Ser Phe Asn Phe Phe Val Thr Ser Pro Ala
            660                 665                 670

Asn Met Ser Asp Ile Ile Pro Arg Ser Asp Val Glu Lys Ala Ile Ser
        675                 680                 685

Met Ser Arg Ser Arg Ile Asn Asp Ala Phe Arg Leu Asp Asp Asn Thr
        690                 695                 700

Leu Glu Phe Leu Gly Ile Gln Pro Thr Leu Gly Pro Pro Asp Glu Pro
705                 710                 715                 720

Pro Val Thr
```

SARS-COV-2 SURROGATE VIRUS NEUTRALIZATION ASSAY TEST KIT

RELATED APPLICATIONS AND INCORPORATION BY REFERENCE

This application claims priority to Singapore Patent Application No. 10202002784P filed Mar. 25, 2020 and Singapore Patent Application No. 10202004468Q filed on May 14, 2020.

The foregoing applications, and all documents cited therein or during their prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

Citation or identification of any document in this application is not an admission that such document is available as prior art to the present disclosure.

FIELD OF THE INVENTION

The present disclosure relates to the detection of antibodies to severe acute respiratory syndrome-related coronavirus (SARSr-CoV), and the diagnosis of SARSr-CoV infection.

BACKGROUND OF THE INVENTION

The coronavirus disease 2019 (COVID-19) outbreak, started in Wuhan, China, has spread rapidly to other cities in China, and affected more than 160 countries with more than 332,930 infections and 14,509 deaths as of 23 Mar. 2020. The etiological agent is severe acute respiratory syndrome coronavirus 2 (SARS-CoV-2), which is genetically 80% identical to severe acute respiratory syndrome coronavirus (SARS-CoV or SARS-CoV-1) which caused the 2002-2003 outbreak of severe acute respiratory syndrome [3].

Current diagnosis is based on clinical history and chest radiographic findings, and confirmation currently relies on nucleic acid-based assays.

There is an urgent need for reliable and easy-to-use assays for the detection of SARS-CoV-2, to expand the tools available to combat this worst pandemic in mankind's modern history.

Unlike molecular tests, serological tests are more difficult to develop and often suffer from specificity issues. The current "gold standard" is virus neutralization test (VNT) which requires the use of live virus in a specialized biocontainment facility, biosafety level 3 (BSL3) lab. The test process is not only expensive and at a biosafety risk, but also slow, typically taking 3-5 days to get results.

Several groups are developing ELISA-based tests to meet the need for BSL2-based tests which can be completed within hours rather than days. The present inventor was the first to use ELISA and VNT assays to facilitate contact tracing in Singapore [30]. Since then, several other groups have developed ELISA tests for SARS-CoV-2 infection [31, 32]. Most groups are using indirect ELISA format (coating ELISA plate with antigen, followed by binding with test sera, and HRP-conjugated secondary antibodies) (FIG. 1). This is the simplest/cheapest serological assay format, hence widely adopted. But it usually suffers from specificity issues. ELISA tests are currently used for "front line" screenings and there is usually a need for confirmation by the more specific and reliable VNT assays [30].

All current ELISA tests are species- (mostly human) and subtype- (IgG or IgM) specific. This can be a major drawback for surveillance studies beyond human sera. There is an urgent need for serological surveillance of different wildlife species to understand the missing link which might be responsible for the transmission of the virus from animal(s) to humans. It is a huge undertaking to develop specific ELISAs for all of the many wildlife species to be surveyed.

SUMMARY OF THE INVENTION

In a first aspect, the present disclosure provides a kit which may comprise: (i) a polypeptide encoded by a SARSr-CoV or a fragment thereof, (ii) a polypeptide which binds specifically to the polypeptide or fragment of (i), and (iii) means for detecting interaction between the polypeptide or fragment of (i), and the polypeptide of (ii).

Also provided is a kit which may comprise: (i) a spike protein or a fragment thereof encoded by a SARSr-CoV, and (ii) an ACE2 protein or a fragment thereof which binds specifically to the spike protein or fragment of (i).

In some embodiments, the kit may further comprise means for detecting interaction between the spike protein or fragment of (i) and the ACE2 protein or fragment of (ii).

In some embodiments, the spike protein or fragment of (i) or the ACE2 protein or fragment of (ii) may be conjugated to a detection entity. In some embodiments, the spike protein or fragment of (i) or the ACE2 protein or fragment of (ii) may be immobilised on a solid support.

In some embodiments,
(a) the spike protein or fragment of (i) is conjugated to a detectable entity, and wherein the ACE2 or fragment of (ii) is immobilised on a solid support; or (b) the ACE2 or fragment of (ii) is conjugated to a detectable entity, and wherein the spike protein or fragment of (i) is immobilised on a solid support.

In some embodiments, the SARSr-CoV may be SARS-CoV-2 or a variant thereof.

In some embodiments, the spike protein or fragment may comprise or consist of the S1 subunit. In some embodiments, the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 12 or 27. In some embodiments, the spike protein or fragment may comprise or consist of the receptor binding domain (RBD) of the spike protein. In some embodiments the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 13 or 26. In some embodiments, the the spike protein or fragment may comprise or consist of the receptor binding motif (RBM) of the spike protein. In some embodiments the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NO: 14.

In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 15, 16 or 29. In some embodiments, the ACE2 protein or fragment may comprise or consist of the extracellular domain. In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 17 or 30.

In some embodiments, the detection entity may be a horseradish peroxidase.

The present disclosure also provides a composition which may comprise:

(a) a solid support, and
(b) (i) a polypeptide encoded by a SARSr-CoV or a fragment thereof, and/or (ii) a polypeptide which binds specifically to the polypeptide or fragment of (i).

The present disclosure also provides a composition which may comprise:

(a) a solid support, and
(b) (i) a spike protein or a fragment thereof encoded by a SARSr-CoV, and/or (ii) an ACE2 protein or a fragment thereof which binds specifically to the spike protein or fragment of (i).

In some embodiments, the composition may further comprise means for detecting interaction between the spike protein or fragment of (i) and the ACE2 protein or fragment of (ii).

In some embodiments, the spike protein or fragment of (i) or the ACE2 protein or fragment of (ii) may be immobilised on the solid support.

In some embodiments, the spike protein or fragment of (i) or the ACE2 protein or fragment of (ii) may be conjugated to a detection entity.

In some embodiments, (a) the spike protein or fragment of (i) is conjugated to a detectable entity, and wherein the ACE2 or fragment of (ii) is immobilised on the solid support; or
(b) the ACE2 or fragment of (ii) is conjugated to a detectable entity, and wherein the spike protein or fragment of (i) is immobilised on the solid support.

In some embodiments, the SARSr-CoV may be SARS-CoV-2 or a variant thereof.

In some embodiments, the spike protein or fragment may comprise or consist of the S1 subunit. In some embodiments, the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 12 or 27. In some embodiments, the spike protein or fragment may comprise or consist of the receptor binding domain (RBD) of the spike protein. In some embodiments, the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 13 or 26. In some embodiments, the the spike protein or fragment may comprise or consist of the receptor binding motif (RBM) of the spike protein. In some embodiments the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NO: 14.

In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 15, 16 or 29. In some embodiments, the ACE2 protein or fragment may comprise or consist of the extracellular domain. In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 17 or 30.

In some embodiments the detection entity may be a horseradish peroxidase.

The present disclosure also provides a polypeptide which may comprise the amino acid sequence of a polypeptide encoded by a SARSr-CoV or a fragment thereof, wherein the polypeptide may be conjugated to a detection entity.

The present disclosure also provides a polypeptide which may comprise the amino acid sequence of a spike protein or a fragment thereof encoded by a SARSr-CoV, wherein the polypeptide may be conjugated to a detection entity.

In some embodiments, the SARSr-CoV may be SARS-CoV-2 or a variant thereof.

In some embodiments, the spike protein or fragment may comprise or consist of the S1 subunit. In some embodiments, the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 12 or 27. In some embodiments, the spike protein or fragment may comprise or consist of the receptor binding domain (RBD) of the spike protein. In some embodiments, the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 13 or 26. In some embodiments, the the spike protein or fragment may comprise or consist of the receptor binding motif (RBM) of the spike protein. In some embodiments the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NO: 14.

The present disclosure also provides a polypeptide which may bind specifically to a polypeptide encoded by a SARSr-CoV or a fragment thereof, wherein the polypeptide may be conjugated to a detection entity.

The present disclosure also provides a polypeptide which may comprise the amino acid sequence of an ACE2 protein or a fragment thereof, wherein the polypeptide may be conjugated to a detection entity.

In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 15, 16 or 29. In some embodiments, the ACE2 protein or fragment may comprise or consist of the extracellular domain. In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 17 or 30.

In some embodiments, the detection entity may be a horseradish peroxidase.

The present disclosure also provides a nucleic acid encoding a polypeptide according to the present disclosure.

The present disclosure also provides a vector which may comprise the nucleic acid according to the present disclosure.

The present disclosure also provides a cell which may comprise the nucleic acid or vector according to the present disclosure.

The present disclosure also provides the use of the kit, composition or polypeptide according to the present disclosure, in a method for detecting the presence of antibodies to a SARSr-CoV in a sample.

In some embodiments, the SARSr-CoV may be SARS-CoV-2 or a variant thereof.

The present disclosure also provides the use of the kit, composition or polypeptide according to the present disclosure, in a method for determining whether a subject is or has been infected with a SARSr-CoV.

In some embodiments, the SARSr-CoV may be SARS-CoV-2 or a variant thereof.

In some embodiments, the subject may be a mammal. In some embodiments, the subject may be a human.

The present disclosure also provides a method of analysing a sample for the presence of antibodies to a SARSr-CoV, which may comprise:
 contacting the sample with: (i) a polypeptide encoded by a SARSr-CoV or a fragment thereof, and (ii) a polypeptide which binds specifically to the polypeptide or fragment of (i), and
 determining the level of interaction between the polypeptide or fragment of (i) and the polypeptide of (ii).

In some embodiments, the SARSr-CoV may be SARS-CoV-2 or a variant thereof.

In some embodiments, the sample may be a blood sample, a lymph sample, a saliva sample, a synovial fluid sample. In some embodiments, the sample may be serum.

The present disclosure also provides a method of determining whether a subject is or has been infected with a SARSr-CoV, which may comprise:
 contacting a sample from the subject with: (i) a polypeptide encoded by a SARSr-CoV or a fragment thereof, and (ii) a polypeptide which binds specifically to the polypeptide or fragment of (i), and
 determining the level of interaction between the polypeptide or fragment of (i) and the polypeptide of (ii).

In some embodiments, the SARSr-CoV may be SARS-CoV-2 or a variant thereof.

In some embodiments, the subject may be a mammal. In some embodiments, the subject may be a human.

In some embodiments, the sample may be a blood sample, a lymph sample, a saliva sample, a synovial fluid sample. In some embodiments, the sample may be serum.

The present disclosure also provides a method of analysing a sample for the presence of antibodies to a SARSr-CoV, which may comprise:
 contacting the sample with: (i) a spike protein or a fragment thereof encoded by a SARSr-CoV, and (ii) an ACE2 protein or a fragment thereof which binds specifically to the spike protein or fragment of (i), and
 determining the level of interaction between the spike protein or fragment of (i) and the ACE2 or fragment of (ii).

The present disclosure also provides a method of determining whether a subject is or has been infected with a SARSr-CoV, which may comprise:
 contacting a sample obtained from the subject with: (i) a spike protein or a fragment thereof encoded by a SARSr-CoV, and (ii) an ACE2 protein or a fragment thereof which binds specifically to the spike protein or fragment of (i), and
 determining the level of interaction between the spike protein or fragment of (i) and the ACE2 or fragment of (ii).

In some embodiments, the spike protein or fragment of (i) or the ACE2 protein or fragment of (ii) may be conjugated to a detection entity.

In some embodiments, the spike protein or fragment of (i) or the ACE2 protein or fragment of (ii) may be immobilised on a solid support.

In some embodiments, the spike protein or fragment of (i) may be conjugated to a detectable entity, and wherein the ACE2 or fragment of (ii) may be immobilised on a solid support.

In some embodiments, the SARSr-CoV may be SARS-CoV-2 or a variant thereof.

In some embodiments, the subject may be a mammal. In some embodiments, the subject may be a human.

In some embodiments, the sample may be a blood sample, a lymph sample, a saliva sample, a synovial fluid sample. In some embodiments, the sample may be serum.

In some embodiments, the spike protein or fragment may comprise or consist of the S1 subunit. In some embodiments, the spike protein or fragment comprises or consists of an amino acid sequence having at least 70%, 75%, 80%, 85%, 90%, 91%, 92%, 93%, 94%, 95%, 96%, 97%, 98% or 99% sequence identity to SEQ ID NOs: 12 or 27. In some embodiments, the spike protein or fragment may comprise or consist of the receptor binding domain (RBD) of the spike protein. In some embodiments the spike protein or fragment may comprise or consist of an amino acid sequence having at least 70%, 75%, 80%, 85%, 90%, 95% or 99% sequence identity to SEQ ID NOs: 13 or 26. In some embodiments, the spike protein or fragment may comprise or consist of the receptor binding motif (RBM) of the spike protein. In some embodiments the spike protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NO: 14.

In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 15, 16 or 29. In some embodiments, the ACE2 protein or fragment may comprise or consist of the extracellular domain. In some embodiments, the ACE2 protein or fragment may comprise or consist of an amino acid sequence having at least 70%, 75%, 80%, 85%, 90%, 91%, 92%, 93%, 94%, 95%, 96%, 97%, 98% or 99% sequence identity to SEQ ID NOs: 17 or 30.

In some embodiments, the detection entity may be a horseradish peroxidase.

Other features and advantages of the instant disclosure will be apparent from the following detailed description and examples which should not be construed as limiting. The contents of all references, GenBank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

FIGS. 8A to 8G. Graphs showing species-independent and virus-specific neutralization. (8A) Rabbit anti-SARS-CoV-2 RBD sera from immunization (n=3). (8B) Ferret anti-SARS-CoV sera from infection (n=2). (8C) Rabbit anti-SARS-CoV sera from immunization (n=2). (8D) SARS-CoV-2 sVNT using different coronavirus sera: human COVID-19 sera (n=10), human SARS sera sampled in 2003 (n=7, <1 year), human SARS-CoV sera sampled in 2020 (n=10, >17 years), human OC43 sera (n=8), human 229E/NL63 sera (n=10), MERS-CoV sera from experimentally infected alpaca (n=4). (8E) Comparative analysis of homologous and heterologous NAb levels for the 2003 SARS serum panel. (8F) Comparative analysis of homologous and heterologous NAb levels for the 2020 SARS serum panel. (8G) Comparative analysis of homologous N-specific antibodies in the three serum cohorts. SARS-CoV-2 N protein indirect ELISA for COVID-19 sera and SARS-CoV N protein indirect ELISA for the two SARS serum panels.

DETAILED DESCRIPTION OF THE INVENTION

Figure 1:
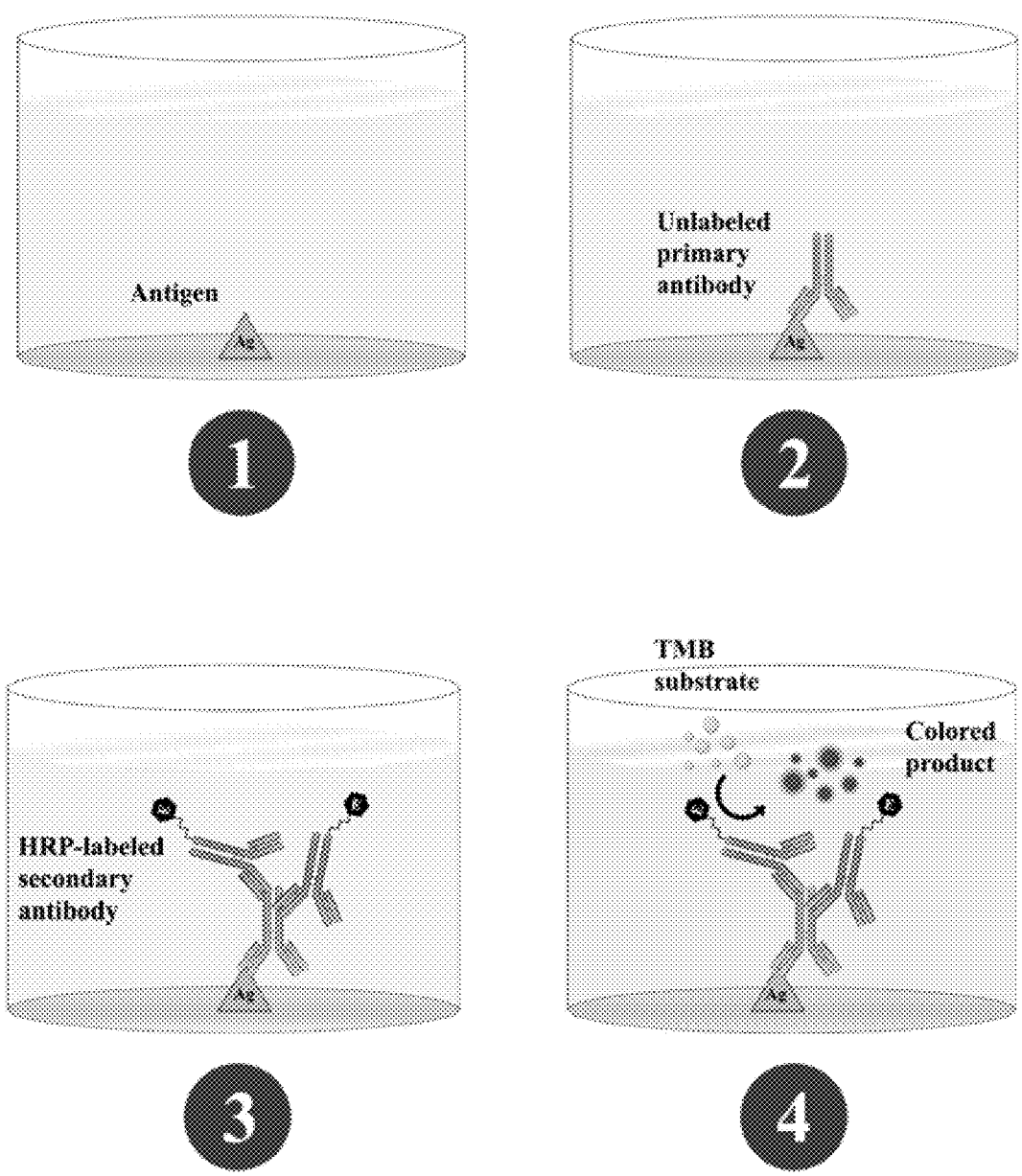
FIG. 1. Schematic representation of the principle of indirect ELISA. 1) Antigen coating; 2) Binding of antigen-specific antibody; 3) Binding of HRP-conjugated secondary antibody; 4) Colour development with HRP substrate (TMB).
Figure 2A:
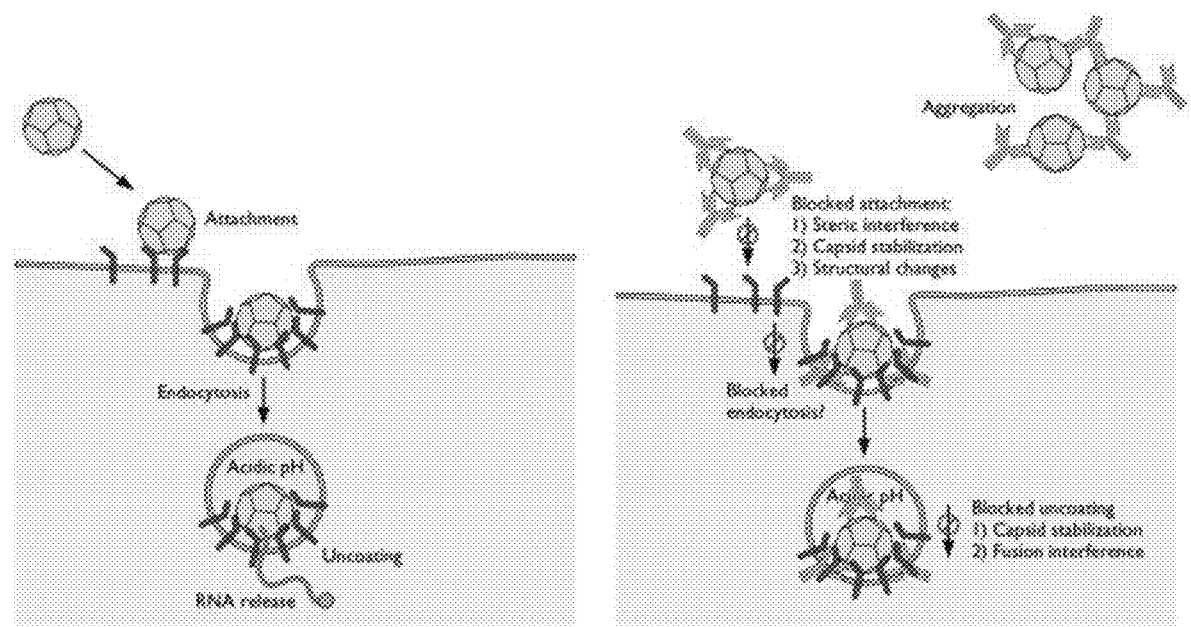
FIGS. 2A and 2B. Schematic representation of the principle of virus neutralization. (2A) Most virus-neutralizing antibodies act by blocking virus attachment although some can also act by blocking uncoating. (2B) Surrogate virus neutralization mimics the action of most neutralizing antibodies by blocking receptor-viral protein interaction in an ELISA plate well.
Figure 2B:
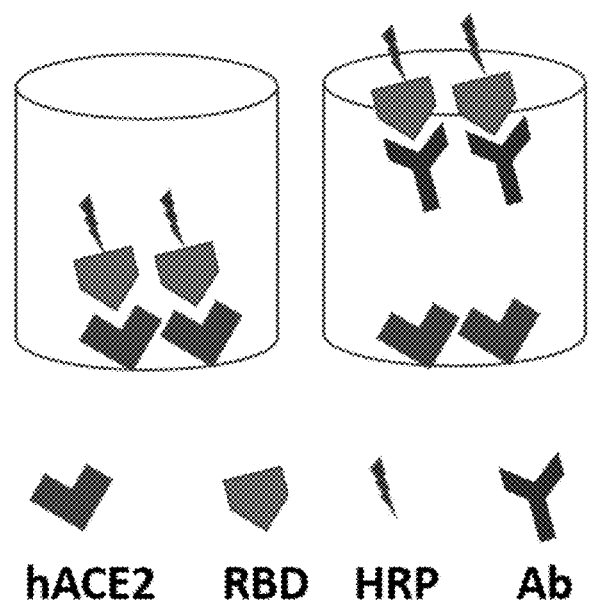

The present invention is based on the principle of using surrogate molecules of live SARSr-CoV in assays for the detection of the presence of neutralising antibody to SARSr-CoV. The invention strips the traditional virus neutralisation test back to its molecular elements, based on antibodies blocking the molecular interaction of the cell entry receptor (ACE2) and the key viral spike protein S1 domain (RBD) (FIG. 2B).

Advantageously, analysis of samples using the articles and in accordance with methods of the present disclosure is more reliable than ELISA-based analysis, and is more versatile, not being limited to the detection of certain antibody isotypes or the detection of antibodies in samples derived from a limited number of species. Rather, the articles and methods of the present disclosure can be employed to detect neutralising antibodies to SARSr-CoV across all antibody isotypes and in samples derived from any species. As the disclosed articles and methods provide for more sensitive and specific analysis, there is no need to confirm results by virus neutralisation tests, as is typically required for ELISA-based analysis.

Moreover, the analysis of samples using the articles and in accordance with methods of the present disclosure is associated with the advantage over virus neutralisation tests that it does not employ live virus or infectious material, and is therefore safe and does not require the use of BSL3 facilities. Furthermore, the use of the articles and methods of the present disclosure is less expensive and time-consuming than virus neutralisation tests, with results obtainable in a matter of hours.

The present disclosure concerns severe acute respiratory syndrome-related coronavirus (SARSr-CoV). The virology of SARSr-CoV and epidemiology of disease associated with SARSr-CoV infection are reviewed, for example, in Cheng et al., Clin Microbiol Rev (2007) 20(4): 660-694 and de Wit et al., Nat Rev Microbiol (2016) 14: 523-534, both of which are hereby incorporated by reference in their entirety.

SARSr-CoV is a species of coronavirus of the genus Betacoronavirus and subgenus Sarbecoronavirus that infects humans, bats and certain other mammals. It is an enveloped positive-sense single-stranded RNA virus.

Two strains of SARSr-CoV have caused serious outbreaks of severe respiratory diseases in humans: SARS-CoV, which caused an outbreak of severe acute respiratory syndrome (SARS) between 2002 and 2003, and SARS-CoV-2, which has caused the coronavirus disease 2019 (COVID-19) pandemic. There are hundreds of strains of SARSr-CoV known only to infect non-human species; bats are a major reservoir of many strains of SARS-related coronaviruses.

In some embodiments in accordance with the various aspects of the present disclosure, the SARSr-CoV is a strain of SARSr-CoV that causes coronavirus disease in humans.

In some embodiments, the SARSr-CoV is SARS-CoV or a variant thereof, or SARS-CoV-2 or a variant thereof. In some embodiments, the SARSr-CoV is SARS-CoV-2 or a variant thereof.

In some embodiments herein, "SARS-CoV" refers to the SARSr-CoV strain having the nucleotide sequence with a GenBank Accession No.: AY278488.2 ("SARS coronavirus BJ01, complete genome") see, e.g., Wu et al., Genomics Proteomics Bioinformatics 1 (2), 131-144 (2003). A variant of SARS-CoV may comprise a nucleotide sequence having at least 80% sequence identity, e.g. one of at least 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to the nucleotide sequence with a GenBank Accession No.: AY278488.2.

As used herein, "sequence identity" refers to the percent of nucleotides/amino acid residues in a subject sequence that are identical to nucleotides/amino acid residues in a reference sequence, after aligning the sequences and, if necessary, introducing gaps, to achieve the maximum percent sequence identity between the sequences. Pairwise and multiple sequence alignment for the purposes of determining percent sequence identity between two or more amino acid or nucleic acid sequences can be achieved in various ways known to a person of skill in the art, for instance, using the publicly available computer software such as ClustalOmega (Soding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such softwares, the default parameters, e.g. for gap penalty and extension penalty, are preferably used.

In some embodiments herein, "SARS-CoV-2" refers to the SARSr-CoV strain having the nucleotide sequence with a GenBank Accession No.: MN996527.1 ("Severe acute respiratory syndrome coronavirus 2 isolate WIV02, complete genome"), reported in Zhou et al., Nature (2020) 579: 270-273. A variant of SARS-CoV-2 may comprise a nucleotide sequence having at least 80% sequence identity, e.g. one of at least 81%, 82%, 83%, 84%, 85%, 86%, 8'7%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% sequence identity to the nucleotide sequence with a GenBank Accession No.: MN996527.1.

In preferred embodiments, the SARSr-CoV is SARS-CoV-2 or a variant thereof.

The present disclosure also concerns polypeptides encoded by a SARSr-CoV.

Herein, a polypeptide refers to any molecule which may comprise three or more amino acid residues joined by peptide bonds. A polypeptide according to the present disclosure encompasses peptides (e.g. tripeptides, oligopeptides, etc.), and also polypeptides which may comprise chemical modification, such e.g. glycosylation (glycopolypeptides), phosphorylation, hydroxylation, sulfonation, palmitoylation, and disulfide formation. Polypeptides may also be referred to as proteins.

Constituent proteins and glycoproteins encoded by the SARSr-CoV genome are described e.g. in Masters, Adv Virus Res. (2006) 66:193-292 and Song et al., Viruses (2019) 11(1): 59, both of which are hereby incorporated by reference in their entirety. The SARSr-CoV genome encodes four major structural proteins: the spike (S) protein, the envelope (E) protein, the membrane (M) protein, and the nucleocapsid (N) protein.

The spike protein of SARS-CoV may have the amino acid sequence shown in SEQ ID NO: 1. The envelope protein of SARS-CoV may have the amino acid sequence shown in SEQ ID NO: 2. The membrane protein of SARS-CoV may have the amino acid sequence shown in SEQ ID NO: 3. The nucleocapsid protein of SARS-CoV may have the amino acid sequence shown in SEQ ID NO: 4.

The spike protein of SARS-CoV-2 may have the amino acid sequence shown in SEQ ID NO: 5. The envelope protein of SARS-CoV-2 may have the amino acid sequence shown in SEQ ID NO: 6. The membrane protein of SARS-CoV-2 may have the amino acid sequence shown in SEQ ID NO: 7. The nucleocapsid protein of SARS-CoV-2 may have the amino acid sequence shown in SEQ ID NO: 8.

In some embodiments, a polypeptide encoded by a SARS-CoV may comprise or consist of the amino acid sequence of SEQ ID NO: 1, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 1. In some embodiments, a polypeptide encoded by a SARS-CoV may comprise or consist of the amino acid sequence of SEQ ID NO: 2, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 2. In some embodiments, a polypeptide encoded by a SARS-CoV may comprise or consist of the amino acid sequence of SEQ ID NO: 3, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 3. In some embodiments, a polypeptide encoded by a SARS-CoV may comprise or consist of the amino acid sequence of SEQ ID NO: 4, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 4.

In some embodiments, a polypeptide encoded by a SARS-CoV-2 may comprise or consist of the amino acid sequence of SEQ ID NO: 5, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 5. In some embodiments, a polypeptide encoded by a SARS-CoV-2 may comprise or consist of the amino acid sequence of SEQ ID NO: 6, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 6. In some embodiments, a polypeptide encoded by a SARS-CoV-2 may comprise or consist of the amino acid sequence of SEQ ID NO: 7, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 7. In some embodiments, a polypeptide encoded by a SARS-CoV-2 may comprise or consist of the amino acid sequence of SEQ ID NO: 8, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 8.

In some embodiments, a polypeptide encoded by a SARSr-CoV is selected from a spike protein, an envelope protein, a membrane protein and a nucleocapsid protein, or a fragment of a spike protein, envelope protein, membrane protein or nucleocapsid protein. In some embodiments, a polypeptide encoded by a SARSr-CoV is selected from a spike protein, an envelope protein or a membrane protein, or a fragment of a spike protein, envelope protein or membrane protein. In some embodiments, a polypeptide encoded by a SARSr-CoV is a spike protein or a fragment of a spike protein.

As used herein, a "fragment" of a reference protein/polypeptide may be of any length (by number of amino acids), although may optionally be at least 25% of the length of the reference protein/polypeptide and may have a maximum length of one of 50%, 75%, 80%, 85%, 90%, 91%, 92%, 93%, 94%, 95%, 96%, 97%, 98%, or 99% of the reference protein/polypeptide.

The SARSr-CoV spike protein comprises S1 and S2 subunits. The S1 subunit comprises a minimal receptor-binding domain (RBD) through which the SARSr-CoV binds to ACE2 expressed by host cells. Although virus neutralization can be achieved by other type of antibodies, receptor/entry blocking antibodies represent a substantial majority of neutralization antibodies for any given virus [33].

The RBD has been shown to be sufficient for binding to ACE2 in in vitro experiments [34]. From SARS studies, it has been shown that most neutralizing antibodies to SARS-CoV are directed against the RBD region [35].

The RBD in turn comprises the receptor binding motif (RBM), which is the region of the RBD that contacts ACE2.

In some embodiments, a polypeptide encoded by a SARSr-CoV may comprise or consist of the S1 subunit of a spike protein. In some embodiments, a polypeptide encoded by a SARSr-CoV may comprise or consist of the RBD of a spike protein. In some embodiments, a polypeptide encoded by a SARSr-CoV may comprise or consist of the RBM of a spike protein.

The S1 subunit of the spike protein of SARS-CoV may have the amino acid sequence shown in SEQ ID NO: 9. The RBD of the spike protein of SARS-CoV may have the amino acid sequence shown in SEQ ID NOs: 10 or 28. The RBM of the spike protein of SARS-CoV may have the amino acid sequence shown in SEQ ID NO: 11.

The S1 subunit of the spike protein of SARS-CoV-2 may have the amino acid sequence shown in SEQ ID NOs: 12 or 27. The RBD of the spike protein of SARS-CoV-2 may have the amino acid sequence shown in SEQ ID NOs: 13 or 26. The RBM of the spike protein of SARS-CoV-2 may have the amino acid sequence shown in SEQ ID NO: 14.

In some embodiments, a polypeptide encoded by a SARSr-CoV (e.g. a spike protein or a fragment thereof encoded by a SARSr-CoV) may comprise or consist of the amino acid sequence of SEQ ID NO: 9, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 9. In some embodiments, a polypeptide encoded by a SARSr-CoV (e.g. a spike protein or a fragment thereof encoded by a SARSr-CoV) may comprise or consist of the amino acid sequence of SEQ ID NOs: 10 or 28, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 10 or 28. In some embodiments, a polypeptide encoded by a SARSr-CoV (e.g. a spike protein or a fragment thereof encoded by a SARSr-CoV) may comprise or consist of the amino acid sequence of SEQ ID NO: 11, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 11.

In some embodiments, a polypeptide encoded by a SARSr-CoV (e.g. a spike protein or a fragment thereof encoded by a SARSr-CoV) may comprise or consist of the amino acid sequence of SEQ ID NOs: 12 or 27, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 12 or 27. In some embodiments, a polypeptide encoded by a SARSr-CoV (e.g. a spike protein or a fragment thereof encoded by a SARSr-CoV) may comprise or consist of the amino acid sequence of SEQ ID NOs: 13 or 26, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 13 or 26. In some embodiments, a polypeptide encoded by a SARSr-CoV (e.g. a spike protein or a fragment thereof encoded by a SARSr-CoV) may comprise or consist of the amino acid sequence of SEQ ID NO: 14, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 14.

The present disclosure also concerns polypeptides which bind specifically to polypeptides/fragments thereof encoded by a SARSr-CoV.

As used herein, "specific binding" refers to interaction which is selective for the relevant molecule, and which can be discriminated from non-specific binding. A polypeptide that binds specifically to a given molecule preferably binds the molecule with greater affinity, and/or with greater duration than it binds to other molecules to which the polypeptide does not bind specifically.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the polypeptide to a non-target molecule is less than about 10% of the level of binding to the molecule to which the polypeptide binds specifically, as measured e.g. by ELISA, SPR, Bio-Layer Interferometry or by RIA. Alternatively, specific binding may be reflected in terms of binding affinity, wherein the polypeptide binds to the molecule to which the polypeptide binds specifically with a dissociation constant ($K_D$) that is at least 0.1 order of magnitude (i.e. $0.1\times10^n$, where n is an integer representing the order of magnitude) greater than the $K_D$ of the polypeptide towards a non-target molecule. This may optionally be one of at least 0.2, 0.3, 0.4, 0.5, 0.6, 0.7, 0.8, 0.9, 1.0, 1.5, or 2.0.

A polypeptide which binds specifically to a polypeptide/fragment encoded by a SARSr-CoV may be e.g. an interaction partner for the polypeptide/fragment encoded by a SARSr-CoV, or an antigen-binding molecule which binds specifically to the polypeptide/fragment encoded by a SARSr-CoV.

An interaction partner for a polypeptide/fragment encoded by a SARSr-CoV may be any polypeptide which associates with the polypeptide/fragment. The association may involve covalent interaction (e.g. disulfide bonding) and/or non-covalent interaction (e.g. electrostatic interaction (e.g. ionic bonding, hydrogen bonding), Van der Waals forces) between the polypeptide/fragment encoded by a SARSr-CoV and the interaction partner.

As used herein, an "antigen-binding molecule" refers to a molecule which is capable of specific binding to a target polypeptide, and encompasses e.g. monoclonal antibodies, polyclonal antibodies, monospecific and multispecific antibodies (e.g., bispecific antibodies), and antibody fragments (e.g. Fv, scFv, Fab, scFab, F(ab')2, Fab2, diabodies, triabodies, scFv-Fc, minibodies, single domain antibodies (e.g. VhH), etc.) and aptamers.

In some embodiments, an interaction partner for a polypeptide/fragment encoded by a SARSr-CoV is a polypeptide expressed by a cell to which the SARSr-CoV binds, or a fragment thereof. In some embodiments, an interaction partner is a receptor molecule expressed at the cell surface of a cell to which the SARSr-CoV binds, or a fragment thereof.

In some embodiments, a polypeptide which binds specifically to a polypeptide/fragment encoded by a SARSr-CoV may comprise or consist of the amino acid sequence of an ACE2 or a fragment thereof, or comprise or consist of an amino acid sequence having at least 60% sequence identity, e.g. one of at least 65%, 70%, 75%, 80%, 85%, 90%, 91%, 92%, 93%, 94%, 95%, 96%, 97%, 98%, 99% or 100% sequence identity to the amino acid sequence of an ACE2 or a fragment thereof.

Angiotensin-converting enzyme 2 (ACE2) is a single-pass type I transmembrane carboxypeptidase which attaches to the cell membrane of cells of the outer surface tissues of lungs, arteries, heart, kidney, and intestines. The structure and function of ACE2 is described e.g. in Hamming et al., J Pathol (2004) 203(2): 631-637, which is hereby incorporated by reference in its entirety. ACE2 has been identified to be the entry point into cells for SARS-CoV and SARS-CoV-2, via interaction with the spike protein. The SARSr-CoV spike protein binds to the extracellular domain of ACE2. ACE2 has been identified as the key cell entry receptor for both SARS-CoV and SARS-CoV-2 [3, 7].

In this specification "ACE2" refers to ACE2 from any species and includes ACE2 isoforms, fragments, variants (including mutants) or homologues from any species. In some embodiments, the ACE2 is ACE2 from a mammal (e.g. a therian, placental, epitherian, preptotheria, archontan, primate (rhesus, cynomolgous, non-human primate or human)). In some embodiments, the ACE2 is ACE2 from a human, bat, pangolin, civet or pig. Isoforms, fragments, variants or homologues of ACE2 may optionally be characterised as having at least 70% sequence identity, preferably one of 80%, 85%, 90%, 91%, 92%, 93%, 94%, 95%, 96%, 97%, 98%, 99% or 100% amino acid sequence identity to the amino acid sequence of an immature or mature ACE2 isoform from a given species, e.g. human.

Human ACE2 isoform 1's amino acid sequence is set forth in SEQ ID NOs: 15 or 29. Human ACE2 isoform 2's amino acid sequence is shown in SEQ ID NO: 16. The extracellular domain of human ACE2 isoform 1 is shown in SEQ ID NOs: 17 or 30.

The bat ACE2 may have the amino acid sequence shown in SEQ ID NOs: 18 or 31. The extracellular domain of bat ACE2 may have the amino acid sequence shown in SEQ ID NOs: 19 or 32.

Pangolin ACE2 may have the amino acid sequence shown in SEQ ID NO: 20. The extracellular domain of pangolin ACE2 may have the amino acid sequence shown in SEQ ID NO: 21.

Civet ACE2 may have the amino acid sequence shown in SEQ ID NO: 22. The extracellular domain of civet ACE2 may have the amino acid sequence shown in SEQ ID NO: 23.

Pig ACE2 may have the amino acid sequence shown in SEQ ID NOs: 24 or 33. The extracellular domain of pig ACE2 may have the amino acid sequence shown in SEQ ID NOs: 25 or 34.

In some embodiments, an ACE2 or fragment thereof may comprise or consist of the amino acid sequence of SEQ ID NOs: 15 or 29, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 15 or 29.

In some embodiments, an ACE2 or fragment thereof may comprise or consist of the amino acid sequence of SEQ ID NO: 16, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 16.

In some embodiments, an ACE2 or fragment thereof may comprise or consist of the amino acid sequence of SEQ ID NOs: 17 or 30, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 17 or 30.

In some embodiments, an ACE2 or fragment thereof may comprise or consist of the amino acid sequence of SEQ ID NOs: 18 or 31, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 18 or 31.

In some embodiments, an ACE2 or fragment thereof may comprise or consist of the amino acid sequence of SEQ ID NOs: 19 or 32, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 19 or 32.

In some embodiments, an ACE2 or fragment thereof may comprise or consist of the amino acid sequence of SEQ ID NO: 20, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 20.

In some embodiments, an ACE2 or fragment thereof may comprise or consist of the amino acid sequence of SEQ ID NO: 21, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 21.

In some embodiments, an ACE2 or fragment thereof may comprise or consist of the amino acid sequence of SEQ ID NO: 22, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 22.

In some embodiments, an ACE2 or fragment thereof may comprise or consist of the amino acid sequence of SEQ ID NO: 23, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NO: 23.

In some embodiments, an ACE2 or fragment thereof may comprise or consist of the amino acid sequence of SEQ ID NOs: 24 or 33, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 24 or 33.

In some embodiments, an ACE2 or fragment thereof may comprise or consist of the amino acid sequence of SEQ ID NOs: 25 or 34, or an amino acid sequence having at least 70% sequence identity, e.g. one of at least 80%, 85%, 90%, 91%, 92%, 93%, 94%, 95%, 96%, 97%, 98% or 99% amino acid sequence identity to the amino acid sequence of SEQ ID NOs: 25 or 34.

In some embodiments, the ACE2 or fragment according to the present disclosure is selected in accordance with the kits, compositions, uses and methods of the present disclosure to display (i) specific binding to the polypeptide/fragment thereof encoded by a SARSr-CoV (e.g. a spike protein or a fragment thereof encoded by a SARSr-CoV), and (ii) an affinity of binding to the polypeptide/fragment thereof encoded by a SARSr-CoV providing for sufficient sensitivity for the reliable detection of the presence in a sample of antibodies to the polypeptide/fragment thereof encoded by a SARSr-CoV (e.g. a spike protein or a fragment thereof encoded by a SARSr-CoV).

The present disclosure provides kits and compositions which may comprise a polypeptide encoded by a SARSr-CoV or a fragment thereof (e.g. a spike protein or a fragment thereof encoded by a SARSr-CoV), and/or a polypeptide which binds specifically to the polypeptide encoded by a SARSr-CoV or fragment (e.g. an ACE2 protein or a fragment thereof which binds specifically to a spike protein or a fragment thereof encoded by a SARSr-CoV).

In some embodiments in accordance with such aspects the kits and compositions may further comprise a solid support.

The solid support may be any solid support to which a polypeptide can readily be immobilised (e.g. by adsorption or conjugation), and which is suitable for the analysis of antibody containing samples, e.g. blood derived samples such as serum samples in accordance with the present disclosure. Suitable solid supports for use in such kits and compositions are well known to the skilled person.

In some embodiments, a solid support may comprise or consist of polystyrene, polypropylene, polycarbonate, cyclo-olefin, glass or quartz. In some embodiments, a solid support may be a microtiter (or "multiwell") plate or microarray plate. In some embodiments, a solid support may be a bead, e.g. a magnetic bead.

A polypeptide according to the present disclosure may be immobilised on (or 'coated' on) a solid support according to the present disclosure in accordance with methods well known to the skilled person. A polypeptide may be covalently or non-covalently immobilised on a solid support.

For example, a polypeptide may be immobilised on a solid support by applying a solution of a polypeptide in buffer solution under conditions suitable for, and for sufficient time to allow, the polypeptide to adsorb to the surface of the solid support. Alternatively, a polypeptide may be conjugated to a solid support, e.g. through a covalent bond.

In some embodiments, articles of the present disclosure may further comprise means for detecting interaction between a polypeptide encoded by a SARSr-CoV or a fragment thereof (e.g. a spike protein or a fragment thereof encoded by a SARSr-CoV) and a polypeptide which binds specifically to the polypeptide encoded by the SARSr-CoV or fragment (e.g. an ACE2 protein or a fragment thereof which binds specifically to a spike protein or a fragment thereof encoded by the SARSr-CoV).

The means for detecting interaction can be any suitable means. For example, the means could employ an antibody capable of specifically binding to the polypeptide complex formed by interaction between the polypeptide encoded by a SARSr-CoV or a fragment thereof and the polypeptide which binds specifically to the polypeptide encoded by the SARSr-CoV or fragment, or could employ a reporter of interaction between the polypeptide encoded by a SARSr-CoV or a fragment thereof and the polypeptide which binds specifically to the polypeptide encoded by the SARSr-CoV or fragment.

In some embodiments, the means for detecting interaction may employ a detection entity. By way of illustration, in the experimental examples hereinbelow SARS-CoV-2 S1 and RBD polypeptides are conjugated to a horseradish peroxidase (HRP) moiety. After washing to remove unbound SARS-CoV-2 S1 and RBD polypeptide, the level of horseradish peroxidase activity is indicative of the amount of S1/RBD bound to the immobilised ACE2.

Accordingly, in some embodiments in accordance with the various aspects of the present disclosure the polypeptide encoded by a SARSr-CoV or a fragment thereof (e.g. a spike protein or a fragment thereof encoded by a SARSr-CoV), and/or the polypeptide which binds specifically to the polypeptide encoded by a SARSr-CoV or fragment (e.g. an ACE2 protein or a fragment thereof which binds specifically to a spike protein or a fragment thereof encoded by a SARSr-CoV) are/is conjugated to a detection entity for use to detect interaction between the polypeptide encoded by a SARSr-CoV or a fragment thereof and the polypeptide which binds specifically to the polypeptide encoded by the SARSr-CoV or fragment.

A detection entity may, for example, be a detectable moiety, e.g. a fluorescent, luminescent, immuno-detectable, radio, chemical, nucleic acid or polypeptide label. In some embodiments, a detection entity may be a moiety having detectable activity, e.g. an enzymatic activity on a given substrate. Examples of detection entities having detectable activity include e.g. horseradish peroxidase (HRP) and luciferase moieties.

In some embodiments wherein a detection entity is a moiety having detectable activity, the kit or composition according to the present disclosure may further comprise reagents required for analysis of the detectable activity.

In some embodiments, the kit or composition according to the disclosure may employ detection by chemiluminescence. That is, in some embodiments, the detectable activity is chemiluminescence. Assays based on detection of chemiluminescence are described e.g. in Kricka et al., Analytica chimica acta, (2003), 500(1): 279-286 and Chen et al., Chinese Journal of Analytical Chemistry (2012) 40(1): 3-10, both of which are hereby incorporated by reference in their entirety.

In some embodiments a detection entity may e.g. be a chemical entity which produces electromagnetic radiation upon appropriate excitation. In some embodiments, a chemical entity may be an acridinium compound (e.g. an acridinium ester or acridinium sulfonamide ester), which may be excited using alkaline hydrogen peroxide.

In some embodiments a detection entity may e.g. be an enzyme entity which catalyses the production of electromagnetic radiation from a luminescent chemical. In some embodiments, an enzyme entity may be HRP, which may be used to catalyse decomposition of luminol in the presence of hydrogen peroxide. In some embodiments, an enzyme entity may be alkaline phosphatase, which may be used to catalyse decomposition of AMPPD.

In some embodiments, the polypeptide encoded by a SARSr-CoV or a fragment thereof (e.g. a spike protein or a fragment thereof (e.g. RBD) encoded by a SARSr-CoV) is provided in the kit or composition of the present disclosure such that in use to analyse a sample, the quantity or concentration of the polypeptide encoded by a SARSr-CoV or a fragment thereof (e.g. a spike protein or a fragment thereof (e.g. RBD) encoded by a SARSr-CoV) is (a) less than or equal to (in molar ratio) the quantity/concentration of neutralising antibodies to the SARSr-CoV in the sample being analysed using the kit or composition, and/or (b) sufficient to produce a detectable signal of interaction between the polypeptide encoded by a SARSr-CoV or a fragment thereof (e.g. a spike protein or a fragment thereof (e.g. RBD) encoded by a SARSr-CoV) and a polypeptide which binds specifically to the polypeptide encoded by the SARSr-CoV or fragment (e.g. an ACE2 protein or a fragment thereof which binds specifically to a spike protein or a fragment thereof encoded by the SARSr-CoV) in the absence of neutralising antibodies to the SARSr-CoV in the sample being analysed using the kit or composition.

The skilled person is able to determine suitable quantities/concentrations of polypeptide encoded by a SARSr-CoV (e.g. a spike protein) or fragment thereof where the compositions and kits are put to such use e.g. by determination of/reference to the quantity/concentration of neutralising antibodies to the SARSr-CoV in samples determined or otherwise known to contain neutralising antibodies to the SARSr-CoV. For example, in some embodiments a suitable quantity/concentration of the polypeptide may be less than or equal to (in molar ratio) the average (e.g. the mean) quantity/concentration of neutralising antibodies to the SARSr-CoV in reference sample(s) containing neutralising antibodies to the SARSr-CoV. In some embodiments, serial dilution of the sample to be tested may be used to determine a suitable quantity of a polypeptide encoded by a SARSr-CoV (e.g. a spike protein) or fragment thereof.

The skilled person is also able to determine suitable quantities/concentrations of polypeptide encoded by a SARSr-CoV (e.g. a spike protein) or fragment thereof where the compositions and kits are put to such use e.g. by determination of/reference to the minimal quantity/concentration required to produce a detectable signal of interaction between the polypeptide encoded by a SARSr-CoV or a fragment thereof (e.g. a spike protein or a fragment thereof (e.g. RBD) encoded by a SARSr-CoV) and the polypeptide which binds specifically to the polypeptide encoded by a SARSr-CoV or fragment (e.g. ACE2) in the absence of neutralising antibodies to the SARSr-CoV in the sample.

The present disclosure also provides the constituent polypeptides of the kits and compositions described herein. The polypeptides may be provided in isolated or substantially purified form.

In some embodiments the polypeptides of the present disclosure may comprise one or more linker sequences between amino acid sequences, e.g. between the amino acid sequence of a spike protein or a fragment thereof encoded by a SARSr-CoV and a detection entity.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence may comprise at least one glycine residue and/or at least one serine residue. In some embodiments the linker sequence may consist of glycine and serine residues. In some embodiments, the linker sequence may have a length of 1-2, 1-3, 1-4, 1-5 or 1-10 amino acids.

The polypeptides of the present disclosure may additionally comprise further amino acids or sequences of amino acids. For example, the polypeptide may comprise amino acid sequence(s) to facilitate expression, folding, trafficking, processing or purification of the polypeptide. For example, the polypeptide may comprise a sequence encoding a His, (e.g. 6×His), Myc, GST, MBP, FLAG, HA, E, or Biotin tag, optionally at the N- or C-terminus of the polypeptide.

The polypeptides of the present disclosure may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the polypeptide, and may be present in the newly synthesised polypeptide. The signal peptide provides for efficient trafficking and secretion of the polypeptide. Signal peptides are often removed by cleavage, and thus are not comprised in the mature polypeptide secreted from the cell expressing the polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Polypeptides according to the disclosure may be prepared according to methods for the production of polypeptides known to the skilled person.

Polypeptides may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety.

Alternatively, polypeptides may be produced by recombinant expression. Molecular biology techniques suitable for recombinant production of polypeptides are well known in the art, such as those set out in Green and Sambrook, Molecular Cloning: A Laboratory Manual (4th Edition), Cold Spring Harbor Press, 2012, and in Nat Methods. (2008); 5(2): 135-146, both of which are hereby incorporated by reference in their entirety.

For recombinant production according to the disclosure, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*. In some embodiments, the cell is a eukaryotic cell such as a yeast cell, a plant cell, insect cell or a mammalian cell, e.g. CHO, HEK (e.g. HEK293), HeLa or COS cells. In some embodiments, the cell is a CHO cell that transiently or stably expresses the polypeptides.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

In some embodiments polypeptides may be prepared by cell-free-protein synthesis (CFPS), e.g. using a system described in Zemella et al. Chembiochem (2015) 16(17): 2420-2431, which is hereby incorporated by reference in its entirety.

Production may involve culture or fermentation of a eukaryotic cell modified to express the polypeptide of interest. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art, and are described, for example, in Green and Sambrook, Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culturing the cells that express the polypeptide, the polypeptide of interest may be isolated. Any suitable method for separating proteins from cells known in the art may be used. In order to isolate the polypeptide it may be necessary to separate the cells from nutrient medium. If the polypeptide is secreted from the cells, the cells may be separated by centrifugation from the culture media that contain the secreted polypeptide of interest. If the polypeptide of interest is collected within the cell, protein isolation may comprise centrifugation to separate cells from cell culture medium, treatment of the cell pellet with a lysis buffer, and cell disruption e.g. by sonification, rapid freeze-thaw or osmotic lysis.

It may then be desirable to isolate the polypeptide of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the polypeptide of interest has been isolated from culture it may be desired or necessary to concentrate the polypeptide. A number of methods for concentrating proteins are known in the art, such as ultrafiltration or lyophilisation.

The present disclosure provides a nucleic acid encoding a polypeptide according to the present disclosure. It will be appreciated that "a nucleic acid" encompasses a plurality of such nucleic acids.

In some embodiments, the nucleic acid is purified or isolated, e.g. from other nucleic acid, or naturally-occurring biological material. In some embodiments the nucleic acid (s) comprise or consist of DNA and/or RNA.

The present disclosure also provides a vector which may comprise the nucleic acid according to the present disclosure.

The nucleotide sequence may be contained in a vector, e.g. an expression vector. A "vector" as used herein is a nucleic acid molecule used as a vehicle to transfer exogenous nucleic acid into a cell. The vector may be a vector for expression of the nucleic acid in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the disclosure.

The term "operably linked" may include the situation where a selected nucleic acid sequence and a regulatory nucleic acid sequence (e.g. promoter and/or enhancer) are covalently linked in such a way as to place the expression of nucleic acid sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. The resulting transcript(s) may then be translated into a desired peptide(s)/polypeptide(s).

Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes).

In some embodiments, the vector may be a eukaryotic vector, e.g. a vector which may comprises the elements necessary for expression of protein from the vector in a eukaryotic cell. In some embodiments, the vector may be a mammalian vector, e.g. that may comprises a cytomegalovirus (CMV) or SV40 promoter to drive protein expression.

The present disclosure also provides a cell which may comprises or expresses a polypeptide according to the present disclosure. Also provided is a cell which may comprises or expresses a nucleic acid or vector according to the present disclosure. The cell may be a eukaryotic cell, e.g. a mammalian cell. The mammal may be a primate (rhesus, cynomolgous, non-human primate or human) or a non-human mammal (e.g. rabbit, guinea pig, rat, mouse or other rodent (including any animal in the order Rodentia), cat, dog, pig, sheep, goat, cattle (including cows, e.g. dairy cows, or any animal in the genus Bos), horse (including any animal in the family Equidae), donkey, and non-human primate).

The present disclosure also provides a method for producing a cell which may comprises a nucleic acid or vector according to the present disclosure, which may comprise introducing a nucleic acid or vector according to the present disclosure into a cell. In some embodiments, introducing an isolated nucleic acid or vector according to the present disclosure into a cell comprises transformation, transfection, electroporation or transduction (e.g. retroviral transduction).

The present disclosure also provides a method for producing a cell which may express or comprise a polypeptide according to the present disclosure, which may comprise introducing a nucleic acid or vector according to the present disclosure in a cell. In some embodiments, the methods additionally comprise culturing the cell under conditions suitable for expression of the nucleic acid or vector by the cell. In some embodiments, the methods are performed in vitro.

The present disclosure also provides cells obtained or obtainable by the methods according to the present disclosure.

The present disclosure also concerns methods using and uses of the kits, compositions and polypeptides of the present disclosure.

The articles of the present disclosure are useful for detecting antibodies to a polypeptide encoded by a SARSr-CoV or a fragment thereof (e.g. a spike protein or a fragment thereof encoded by a SARSr-CoV).

In particular, the articles of the present disclosure are useful for detecting the presence of antibodies which reduce or inhibit binding of a polypeptide encoded by a SARSr-CoV or fragment thereof to a polypeptide which binds specifically to the polypeptide encoded by a SARSr-CoV or fragment. Such antibodies may be referred to as neutralising antibodies.

By way of further explanation, with reference to the experimental examples hereinbelow, the presence of antibodies which inhibit binding of SARS-CoV-2 spike protein S1 subunit and SARS-CoV-2 spike protein RBD are detected in samples based on the determination of a reduced level of interaction between the SARS-CoV-2 spike protein S1 subunit or SARS-CoV-2 spike protein RBD with ACE2 immobilised on the solid support. The presence of neutralising antibodies in the sample is inferred from the determination of a reduced level of interaction relative to a control condition lacking neutralising antibodies to SARS-CoV-2 spike protein S1 subunit or SARS-CoV-2 spike protein RBD.

Accordingly, the articles of the present disclosure are useful in methods for detecting the presence of antibodies to a SARSr-CoV in a sample. It will be appreciated that the methods are useful for the detection of the presence of antibodies to the spike protein or a fragment thereof encoded by a SARSr-CoV employed in the kit/composition.

By way of illustration, the assays exemplified herein employ SARS-CoV-2 spike protein S1 subunit or SARS-CoV-2 spike protein RBD, and are therefore useful for the detection of antibodies to SARS-CoV-2 spike protein S1 subunit or SARS-CoV-2 spike protein RBD.

Detection of the presence of antibodies to a SARSr-CoV in a sample may be indicative of an ongoing or previous infection with the SARSr-CoV. Detection of the presence of antibodies to a SARSr-CoV in a sample may be indicative of an ongoing or previous immune response, particularly a humoral immune response, to the SARSr-CoV.

Accordingly, the present disclosure provides methods for determining whether a subject is or has been infected with a SARSr-CoV, and also provides methods for determining whether a subject is mounting/has mounted an immune response (e.g. a humoral immune response) to a SARSr-CoV.

The methods may generally comprise analysing a sample in order to determine whether its contents reduce or inhibit interaction between a polypeptide encoded by a SARSr-CoV (e.g. a spike protein) or fragment thereof and a polypeptide which binds specifically to the polypeptide encoded by a SARSr-CoV or fragment (e.g. ACE2), relative to the level of interaction observed for an appropriate negative control condition.

An appropriate negative control condition may e.g. employ an equivalent sample known to lack antibodies capable of reducing or inhibiting interaction between a polypeptide encoded by a SARSr-CoV (e.g. a spike protein) or fragment thereof and a polypeptide which binds specifically to the polypeptide encoded by a SARSr-CoV or fragment (e.g. ACE2). For example, a control sample may be from a known naïve subject, e.g. a subject known not to have been infected with the SARSr-CoV.

Determination of reduced or inhibited interaction indicates the presence of neutralising antibodies to the polypeptide encoded by a SARSr-CoV or fragment thereof (e.g. the spike protein or fragment thereof) in the sample.

As used herein, "reduced" or "inhibited" interaction may be a level of interaction which is less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of interaction between the polypeptide encoded by a SARSr-CoV (e.g. a spike protein) or fragment thereof and the polypeptide which binds specifically to the polypeptide encoded by a SARSr-CoV or fragment (e.g. ACE2) observed in the negative control condition.

Alternatively, "reduced" or "inhibited" interaction may be expressed in terms of percentage inhibition of the level of interaction between the polypeptide encoded by a SARSr-CoV (e.g. a spike protein) or fragment thereof and the polypeptide which binds specifically to the polypeptide encoded by a SARSr-CoV or fragment (e.g. ACE2) observed in the negative control condition. In such instances, "reduced" or "inhibited" interaction may refer to percentage inhibition of greater than 0%, e.g. greater than 5%, 10%, 15%, 20%, 25%, 30%, 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, or 100% of the level of interaction between the polypeptide encoded by a SARSr-CoV (e.g. a spike protein) or fragment thereof and the polypeptide which binds specifically to the polypeptide encoded by a SARSr-CoV or fragment (e.g. ACE2) observed in the negative control condition.

In some embodiments, aspects of the present disclosure may comprise:
- contacting a sample obtained from the subject with: (i) a polypeptide encoded by a SARSr-CoV (e.g. a spike protein) or fragment thereof, and (ii) a polypeptide which binds specifically to the polypeptide encoded by a SARSr-CoV or fragment (e.g. ACE2), and
- determining the level of interaction between the polypeptide or fragment of (i) and the polypeptide of (ii).

In some embodiments, aspects of the present disclosure may comprise:
- (a) contacting a sample obtained from the subject with (i) a polypeptide encoded by a SARSr-CoV (e.g. a spike protein) or fragment thereof,
- (b) contacting the mixture formed by step (a) with (ii) a polypeptide which binds specifically to the polypeptide encoded by a SARSr-CoV or fragment (e.g. ACE2), and
- (c) determining the level of interaction between the polypeptide or fragment of (i) and the polypeptide of (ii).

In some embodiments, aspects of the present disclosure may comprise:
- (a) contacting a sample obtained from the subject with (i) a polypeptide which binds specifically to the polypeptide encoded by a SARSr-CoV or fragment (e.g. ACE2),
- (b) contacting the mixture formed by step (a) with (ii) a polypeptide encoded by a SARSr-CoV (e.g. a spike protein) or fragment thereof, and
- (c) determining the level of interaction between the polypeptide or fragment of (i) and the polypeptide of (ii).

In some embodiments, "contacting" samples/mixtures with polypeptides according to the present disclosure may comprise mixing such samples/mixture and compositions (e.g. solutions) which may comprise the polypeptides, e.g. in an appropriate container or on an appropriate solid support.

In some embodiments, "contacting" samples/mixtures with polypeptides according to the present disclosure may comprise applying a sample/mixture to a solid support to which the polypeptides are immobilised.

In some embodiments, the aspects may comprise contacting the sample with a composition which comprises a polypeptide encoded by a SARSr-CoV (e.g. a spike protein) or fragment thereof (RBD)), wherein the polypeptide is provided at a quantity or concentration which is (a) less than or equal to (in terms of molar ratio) the quantity/concentration of neutralising antibodies to the SARSr-CoV in the sample, and/or (b) sufficient to produce a detectable signal of interaction between the polypeptide or fragment of (i) and the polypeptide or fragment of (ii) in the absence of neutralising antibodies to the SARSr-CoV in the sample.

In some embodiments, the aspects may comprise determining the presence or absence of neutralising antibodies to the SARSr-CoV in the sample. In some embodiments, the aspects may comprise determining the quantity and/or concentration of neutralising antibodies to the SARSr-CoV in the sample.

The skilled person is able to determine suitable quantities/concentrations of polypeptide encoded by a SARSr-CoV (e.g. a spike protein) or fragment thereof to be employed in such methods e.g. by determination of/reference to the quantity/concentration of neutralising antibodies to the SARSr-CoV in samples determined or otherwise known to contain neutralising antibodies to the SARSr-CoV. For example, in some embodiments a suitable quantity/concentration of the polypeptide may be less than or equal to (in molar ratio) the average (e.g. the mean) quantity/concentration of neutralising antibodies to the SARSr-CoV in reference sample(s) containing neutralising antibodies to the SARSr-CoV.

The skilled person is also able to determine suitable quantities/concentrations of polypeptide encoded by a SARSr-CoV (e.g. a spike protein) or fragment thereof to be employed in such methods e.g. by determination of/reference to the minimal quantity/concentration required to produce a detectable signal of interaction between the polypeptide encoded by a SARSr-CoV or a fragment thereof (e.g. a spike protein or a fragment thereof (e.g. RBD) encoded by a SARSr-CoV) and the polypeptide which binds specifically to the polypeptide encoded by a SARSr-CoV or fragment (e.g. ACE2) in the absence of neutralising antibodies to the SARSr-CoV in the sample.

In some embodiments, the aspects may employ a range of different quantities/concentrations of polypeptide encoded by a SARSr-CoV (e.g. a spike protein) or fragment thereof for the analysis of a given sample. That is, in some embodiments, aspects of the present disclosure may comprise performing the analysis with a range of different quantities/concentrations of the polypeptide encoded by a SARSr-CoV (e.g. a spike protein) or fragment thereof for the analysis of aliquots of a given same sample. The range of different quantities/concentrations of the polypeptide may be a dilution series, and may e.g. by prepared by serial dilution of a solution of the polypeptide.

In some embodiments, the aspects may further comprise one or more of the following:

obtaining a sample (e.g. a blood sample) from a subject;
preparing a blood-derived sample (e.g. a serum sample) from a blood sample obtained from a subject;
providing a composition or kit according to the present disclosure;
applying a blood-derived sample (e.g. a serum sample) to a composition according to the present disclosure;
incubating the sample with the polypeptides/composition for sufficient time and under appropriate conditions for the formation of antibody:antigen complexes;
aspiration of the sample;
washing to remove unbound proteins;
detection of interaction between the polypeptide or fragment of (i) and the polypeptide or fragment of (ii).

In some embodiments, the aspects may further comprise determining the level (e.g. the percentage) of inhibition of interaction between the polypeptide or fragment of (i) and the polypeptide or fragment of (ii).

In some embodiments, the aspects may further comprise comparing the level (e.g. the percentage) of inhibition of interaction between the polypeptide or fragment of (i) and the polypeptide or fragment of (ii) as observed to a reference threshold value for determining that the sample contains neutralising antibodies to the SARSr-CoV. In some embodiments, the aspects may further comprise determining on the basis of such comparison whether a sample contains or does not contain neutralising antibodies to the SARSr-CoV (i.e. determining the presence or absence of neutralising antibodies to the SARSr-CoV in the sample).

Appropriate reagents, buffers and washing steps to be employed in such methods are well known to the person skilled in the art of molecular biology, and can moreover be inferred by reference to the experimental examples herein and Bossart et al., J Viol Meth (2007) 142: 29-40, which is hereby incorporated by reference in its entirety.

In some aspects, the articles and methods of the present disclosure are employed for the diagnosis of infection with a SARSr-CoV, e.g. SARS-CoV-2. In some aspects, the articles and methods are employed for the diagnosis of a disease caused by infection with a SARSr-CoV, e.g. COVID-19.

Aspects of the present disclosure concern the analysis of samples from subjects. The sample may be of, or may be derived from, any product produced by a subject. A sample may be taken from any tissue or bodily fluid, e.g. a blood sample (including blood-derived samples), serum sample, lymph sample, saliva sample, synovial fluid sample. A blood-derived sample may be a selected fraction of a patient's blood, e.g. a selected cell-containing fraction, or a plasma or serum fraction.

The sample may be any sample containing the antibody products of a humoral immune response. In some embodiments the sample obtained from a subject is an antibody-containing sample or antibody-containing fraction thereof. The sample is preferably a blood sample or a blood-derived sample, more preferably a serum sample.

Samples may be collected (e.g. by venesection), processed and/or stored (e.g. frozen and stored at −80° C.) according to known techniques, and in accordance with the analysis to be subsequently performed on the sample.

A sample may be or may have been collected from a subject of interest. The subject according to the various aspects of the present disclosure may be any animal. In some embodiments, the subject is a mammal (e.g. a therian, placental, epitherian, preptotheria, archontan, primate (rhesus, cynomolgous, non-human primate or human)). In some embodiments, the subject is a human, bat, pangolin, civet or pig. The subject may be a non-human mammal, but is more preferably human. The subject may be male or female. The subject may be a patient.

The subject may be suspected of being infected with a SARSr-CoV, or may be suspected of having a disease caused by infection with a SARSr-CoV. The subject may be suspected of having previously been infected with a SARSr-CoV, or may be suspected of having previously had a disease caused by infection with a SARSr-CoV.

The subject may have been diagnosed with infection with a SARSr-CoV or may have been diagnosed with a disease caused by infection with a SARSr-CoV. The subject may have experienced infection with a SARSr-CoV or may have had a disease caused by infection with a SARSr-CoV.

In particular embodiments, the articles and methods of the present disclosure provide for the detection of the presence in a sample (e.g. a patient-derived sample) of neutralising antibodies to a SARSr-CoV (e.g. SARS-CoV-2), based on detection of blocking of the interaction/binding between an ACE2 protein or fragment thereof and a spike protein or fragment thereof encoded by the SARSr-CoV (e.g. the RBD of the SARSr-CoV) by such neutralising antibodies.

More particularly, preferred embodiments provide for the detection of the presence in a sample (e.g. a sample derived from a COVID-19 patient) of neutralising antibodies to a SARS-CoV-2, based on detection of blocking of the interaction/binding between an ACE2 protein or fragment thereof and the RBD of the SARS-CoV-2 by such neutralising antibodies.

Even where such neutralising antibodies are present in a sample, they will often be present at low levels (i.e. there will be a limited quantity of the antibody). In such instances, if there is an over-supply (i.e. an excess) of spike protein/fragment thereof (e.g. RBD) in the reaction mix, the quantity of antibodies in a test sample may be insufficient to bind to all of the spike protein/fragment thereof (e.g. RBD) available, and the surplus spike protein/fragment thereof (e.g. RBD) will bind to the ACE2 protein/fragment thereof yielding signal, and thus resulting in a false-negative result.

Therefore, in preferred embodiments in accordance with the preset disclosure, the quantity of spike protein/fragment thereof (e.g. RBD) is present in the reaction mix at a level which is (i) sufficient to provide a detectable level of signal (i.e. on interaction with the ACE2 protein/fragment thereof) in the absence of neutralising antibodies to the SARSr-CoV to enable the correct determination of true negative samples lacking neutralising antibodies to the SARSr-CoV, but (ii) not more, in terms of molar ratio (i.e. no molar excess of), than the amount of neutralising antibodies to the SARSr-CoV in the sample, such that all of the spike protein/fragment thereof (e.g. RBD) present in the reaction mix will be neutralized by the antibodies available in the sample, and false-negative results will be avoided.

It will be appreciated that one way to achieve the optimal quantity of the spike protein/fragment thereof (e.g. RBD) in the reaction mix is to prepare a solution (e.g. using a suitable buffer) containing the soluble spike protein/fragment thereof (e.g. RBD) at an appropriate concentration (e.g. by serial dilution of a stock solution), and to use an appropriate volume of the spike protein/fragment thereof (e.g. RBD)-containing solution in the reaction mix.

Another way to achieve the optimal quantity of the spike protein/fragment thereof (e.g. RBD) in the reaction mix is to provide an appropriate quantity of the spike protein/fragment thereof (e.g. RBD) to the reaction mix e.g. in a form immobilized on a solid support, e.g. in the form of the spike protein/fragment thereof (e.g. RBD) immobilized on beads.

The person of ordinary skill in the art would readily recognize permutations of the embodiments of particular interest described above may be devised, and that the articles and methods of the present disclosure can be calibrated and therefore be made quantitative or at least semi-quantitative.

In some embodiments in accordance with the various aspects of the present disclosure, the kits, compositions and methods may be characterised by reference to certain functional properties.

In some embodiments, a kit, composition and/or method according to the present disclosure may possess one or more of the following properties:
(i) Ability to detect the presence of neutralising antibodies to the SARSr-CoV in a sample with greater than 90% (e.g. one of greater than 91%, 92%, 93%, 94%, 95%, 96%, 97%, 98% or 99%, or 100%) specificity;
(ii) Ability to detect the presence of neutralising antibodies to the SARSr-CoV in a sample with greater than 90% (e.g. one of greater than 91%, 92%, 93%, 94%, 95%, 96%, 97%, 98% or 99%, or 100%) sensitivity;
(iii) Ability to detect the presence of neutralising antibodies to the SARSr-CoV in a sample without employing the relevant live SARSr-CoV;
(iv) Ability to detect the presence of neutralising antibodies to the SARSr-CoV irrespective of antibody isotype;
(v) Ability to detect the presence of neutralising antibodies to the SARSr-CoV in a sample irrespective of the species of the subject from which the sample is derived; and
(vi) Ability to arrive at a determination of the presence or absence of neutralising antibodies to the SARSr-CoV in a sample within less than 12 hours (e.g. one of less than 11 hours, 10 hours, 9 hours, 8 hours, 7 hours, 6 hours, 5 hours, 4 hours, 3 hours, 2 hours or 1 hour).

The disclosure includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the disclosure in diverse forms thereof.

For the avoidance of any doubt, any theoretical explanations provided herein are provided for the purposes of improving the understanding of a reader. The inventor will not be bound by any of these theoretical explanations.

Where a nucleic acid sequence is disclosed herein, the reverse complement thereof is also expressly contemplated. Also, where a polypeptide-encoding nucleic acid sequence is disclosed herein equivalent polypeptide-encoding sequences as a result of degeneracy of the genetic code are also expressly contemplated.

The singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Methods disclosed herein may be performed, or products may be present, in vitro, ex vivo, or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms. In some embodiments, methods performed in vivo may be performed on non-human animals. "Ex vivo" refers to something present or taking place outside an organism, e.g. outside the human or animal body, which may be on tissue (e.g. whole organs) or cells taken from the organism.

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press.

Aspects and embodiments of the present disclosure will now be discussed with reference to the accompanying figures and the following examples. Further aspects and embodiments will be apparent to those skilled in the art. All documents mentioned in this text are incorporated herein by reference in their entirety. While the disclosure has been described in conjunction with the exemplary embodiments described below, many equivalent modifications and variations will be apparent to those skilled in the art when given this disclosure. Accordingly, the exemplary embodiments of the disclosure are considered to be illustrative and not limiting. Various changes to the described embodiments may be made without departing from the spirit and scope of the disclosure.

EXAMPLES

Example 1: Surrogate Virus Neutralization Test

In this Example, the inventor presents a novel surrogate virus neutralization test (COVID-sVNT).

1.1 Materials and Methods

Recombinant His-tagged human ACE2 (hACE2, Cat #: 10108-H08H) was purchased from SinoBiologics. Recombinant SARS-CoV-2 nucleoprotein (NP) (Cat #: Z03488), spike protein S1 subunit (Cat #: Z03501) and spike protein RBD (Cat #: Z03479) were purchased from GenScript and conjugated with horse radish peroxidase (HRP) through customer service by GenScript.

1) Indirect ELISA: RBD protein (50 ng) was coated in a 96-well ELISA plate. Test serum was incubated at 1:100 dilution, after washing to remove unbound protein, followed by incubation with HRP-conjugated anti-human antibody (at a dilution of 1:10,000). After washing, HRP substrate was added for colour development.

2) Surrogate virus-host binding assay: hACE2 was coated onto wells of a 96-well plate at a concentration of 100 ng/well. After washing to remove unbound protein, HRP-conjugated recombinant nucleoprotein, S1 or RBD protein (20-100 ng) was then added to assess specific binding. After washing, HRP substrate was added for colour development.

3) Surrogate virus neutralization test (sVNT): hACE2 was coated onto wells of a 96-well plate at a concentration of 100 ng/well. In a separate plate, HRP-conjugated recombinant nucleoprotein, S1 or RBD protein (20-100 ng) was preincubated with different dilutions of test sera. The serum-HRP-protein mixes were then added to the hACE2 coated plate to assess specific inhibition/neutralization. After washing, HRP substrate was added for colour development.

1.2 Results

Six serum samples were used in this proof of concept study: two SARS-CoV-2 positive serum samples (COVID-55, COVID-63), two SARS-CoV positive serum samples (SARS-2, SARS-7), one negative serum sample (NEGATIVE), and one unknown serum sample (TEST-007).

The results of the above two assays are shown in the table 1 below.

TABLE 1

Results of indirect ELISA and sVNT

| Sample | ELISA[1] | sVNT-RBD[2] | sVNT-S1[2] | VNT[3] |
|---|---|---|---|---|
| COVID-55 | 1.49 | +ve | +ve | +ve |
| COVID-63 | 1.62 | +ve | +ve | +ve |
| TEST-007 | 1.04 | −ve | −ve | −ve |
| SARS-2 | 0.20 | −ve | −ve | −ve |
| SARS-7 | 0.25 | −ve | −ve | −ve |
| NEGATIVE | 0.10 | −ve | −ve | −ve |

Figure 3A:
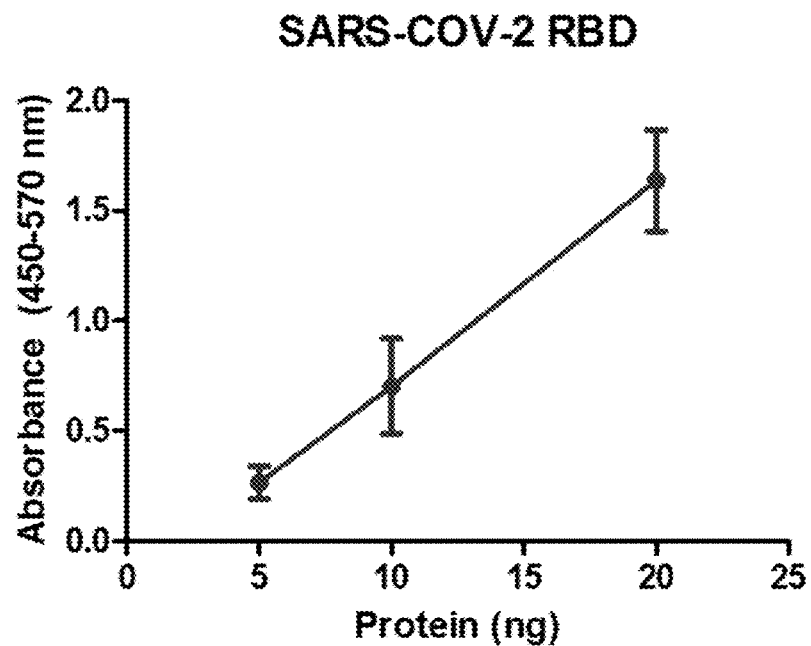
FIGS. 3A and 3B. Graphs showing the results of analysis of direct binding to hACE2 coated onto an ELISA plate for (3A) recombinant HRP-conjugated SARS-CoV-2 spike protein RBD, (3B) recombinant HRP-conjugated SARS-CoV-2 spike protein S1 subunit, and recombinant HRP-conjugated SARS-CoV-2 nucleoprotein.
Figure 3B:
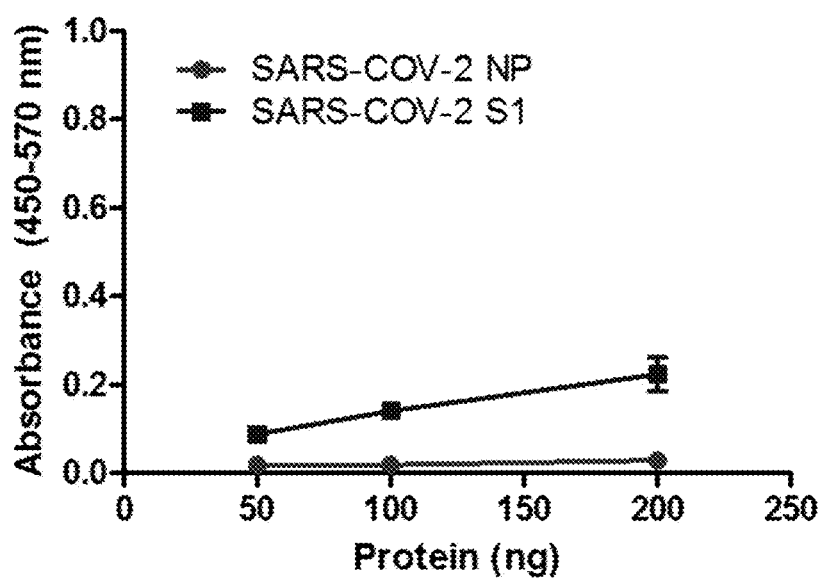

[1]Average from two independent experiments
[2]Inhibition/neutralization at 1:40 or greater dilution
[3]Neutralisiton at 1:20 or greater dilution In the surrogate virus-host binding assay, when different HRP-protein conjugates were added to the hACE2 coated plate, the HRP-NP displayed no binding at all (FIG. 3B) whereas both HRP-S1 and HRP-RBD displayed significant binding (FIGS. 3A and 3B), demonstrating that the recombinant S1 and RBD proteins were functional, and suitable to be used in surrogate virus neutralization assays.

As a proof of concept, the inventor conducted the sVNT using the same panel of sera used for the indirect ELISA.

Figure 4A:
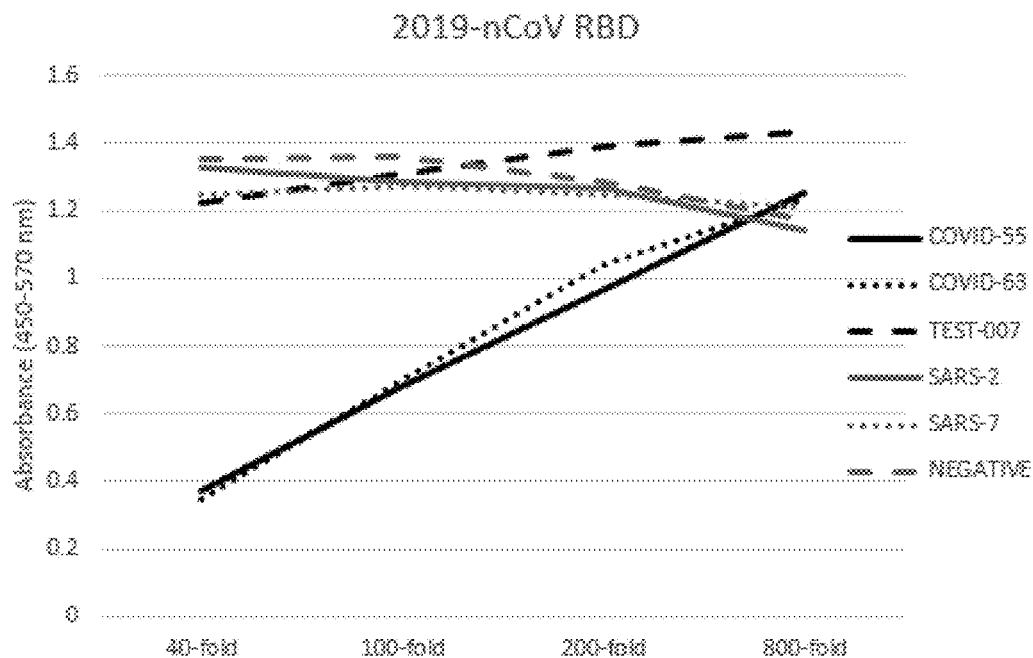
FIGS. 4A and 4B. Graphs showing the results of analysis of serum samples by surrogate virus neutralisation test (sVNT) using immobilised human ACE2 protein and (4A) HRP-conjugated SARS-CoV-2 spike protein RBD or (4B) HRP-conjugated SARS-CoV-2 spike protein S1 subunit.
Figure 4B:
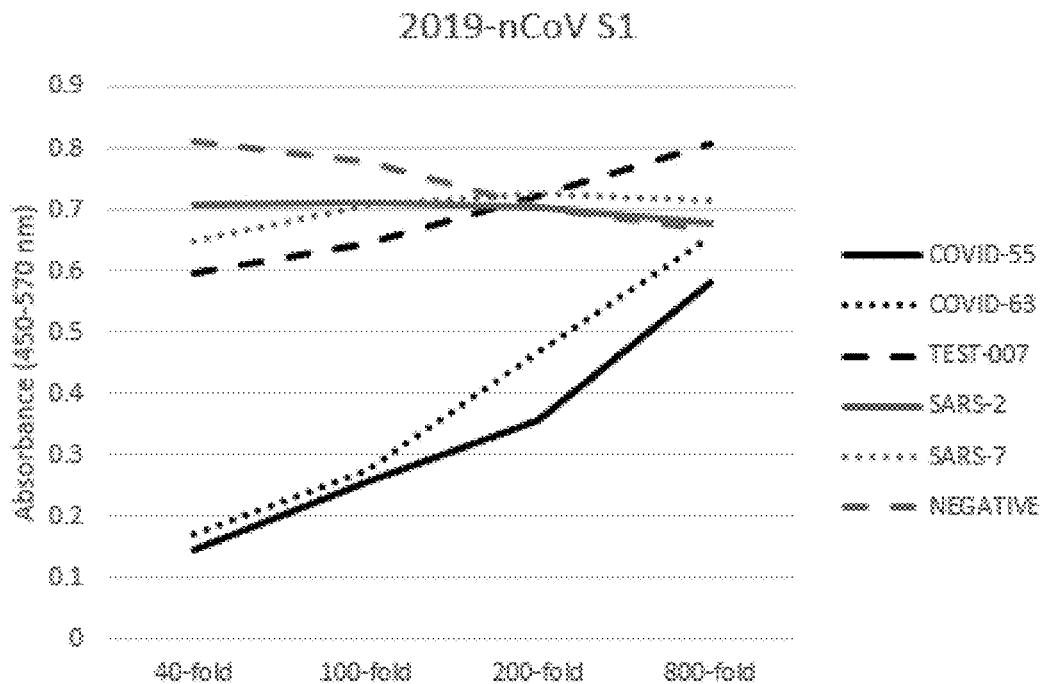

As shown in FIGS. 4A and 4B, only the two SARS-CoV-2 positive sera showed significant inhibition/neutralization in either RBD- (FIG. 4A) or S1- (FIG. 4B) based sVNT. The assay demonstrated excellent specificity, with the inhibition curves for COVID-19 samples in FIGS. 4A and 4B being completely dose and dilution dependent.

The inventor next performed analysis of 74 serum samples obtained from COVID-19 patients having been tested positive by PCR for SARS-CoV-2 infection, and 11 negative (healthy) human serum samples, using the version of the sVNT employing recombinant HRP-conjugated SARS-CoV-2 spike protein RBD.

Figure 5:
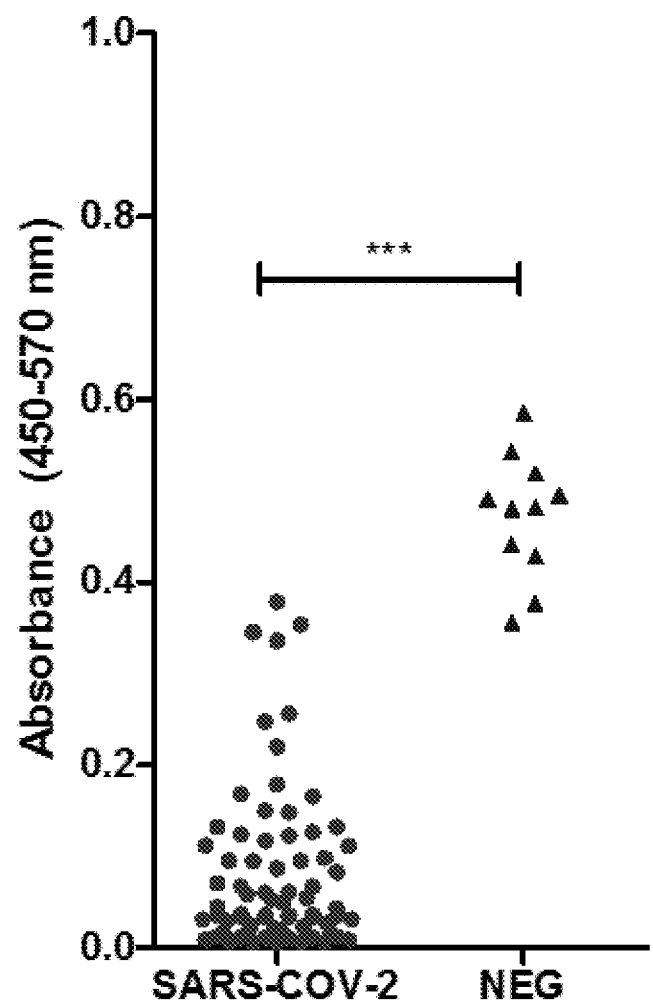
FIG. 5. Graph showing the results of analysis of 74 serum samples from PCR-confirmed COVID-19 patients and 11 negative (healthy) human serum samples using the sVNT using immobilised human ACE2 protein and HRP-conjugated SARS-CoV-2 spike protein RBD.

The results are shown in FIG. 5. The sVNT was able to reliably distinguish samples containing neutralising antibodies to SARS-CoV-2 from samples not containing such antibodies.

It is known that not all COVID-19 patients induce strong neutralising antibody responses to SARS-CoV-2, accounting for the results in samples determined by sVNT to be weakly-positive.

1.3 Conclusion

In conclusion, the inventor has developed an assay capable of detecting neutralising antibodies to SARS-CoV-2 with high sensitivity and specificity.

Importantly, the surrogate virus neutralization test is more specific than the widely-used indirect ELISA assay, as evidenced by the TEST-007 sample giving a positive reading in the indirect ELISA assay, but being shown by the surrogate virus neutralization test to be negative (as confirmed by the live virus neutralisation test).

Example 2: SARS-CoV-2 Surrogate Virus Neutralization Test (sVNT) Based on Antibody-Mediated Blockage of ACE2-Spike (RBD) Protein Interaction There is an urgent need for a robust serological test to detect neutralizing antibodies to SARS-CoV-2. Such a test is not only important for contact tracing, but for determining infection rate, herd immunity and predicted humoral protection. The current gold standard is a virus neutralization test (VNT) requiring live virus and a biosafety level 3 (BSL3) laboratory. On the other hand, the ELISA- or lateral flow-based assays are for the detection of binding antibodies, which does not directly correlate with their neutralizing ability. Here the inventor describes a SARS-CoV-2 surrogate virus neutralization test (sVNT) that is designed to detect total neutralizing antibodies in an isotype- and species-independent manner. This simple and rapid test is based on antibody-mediated blockage of virus-host interaction between the ACE2 receptor protein and the receptor binding domain (RBD) of the viral spike protein. The test has been validated with two COVID-19 patient cohorts in two different countries, achieving 100% specificity and 95-100% sensitivity, and is capable of differentiating antibody responses from other known human coronaviruses. Importantly, the sVNT does not require BSL3 containment, thereby making the test immediately accessible to the global community.

2.1 Introduction

The COVID-19 outbreak was first recognized in December 2019 in Wuhan, China[1], which has since spread to all parts of the world resulting in a total 2,160,207 infections with 146,088 deaths as of 18 Apr. 2020[2]. The causative agent was identified as 2019-nCoV, subsequently designated SARS-CoV-2[3,4], which belongs to the species SARS-related coronavirus (SARSr-CoV), same as for SARS-CoV, the causative agent of the SARS outbreak 17 years ago[5].

While molecular detection, such as polymerase chain reaction (PCR) and next generation sequencing (NGS), played and continue to play an important role in acute diagnosis and monitoring of genetic changes of the virus, there is now an urgent need for a reliable and versatile serological or antibody test. Such a test is needed for retrospective contact tracing, investigation of asymptomatic infection rate, accurate determination of case fatality rate, assessment of herd immunity and humoral protective immunity in recovered patients and recipients of vaccine candidates, and in the search for the natural reservoir host and intermediate host(s) [6]. Research laboratories and pharmaceutical companies are racing to produce antibody tests that can detect SARS-CoV-2 infection with sufficient specificity and sensitivity [6]. There are two types of antibody tests one can aim for. The first type is the virus neutralization test (VNT) which detects neutralizing antibodies (NAbs) in a patient's blood. VNT requires handling live SARS-CoV-2 in a specialized biosafety level 3 (BSL3) containment facility which is tedious and time consuming, taking 2-4 days to complete. Pseudovirus-based virus neutralization test (pVNT) is similar, but still requires the use of live viruses and cells although handled in a BSL2 laboratory [7, 8]. All other assays, such as ELISA and lateral flow rapid tests, represent the second assay type which detect only binding antibodies, and not NAbs [6, 9-11].

In this Example the inventor describes a surrogate virus neutralization test (sVNT) which detects NAbs, but without the need to use any live virus or cells and can be completed in 1-2 hours in a BSL2 lab. Using purified receptor binding domain (RBD) protein from the viral spike (S) protein and the host cell receptor ACE2, the test is designed to mimic the virus-host interaction by direct protein-protein interaction in a test tube or an ELISA plate well. This highly specific interaction can then be neutralized, i.e., blocked by highly specific NAbs in patient or animal sera in the same manner as in a conventional VNT.

2.2 Materials and Methods

Human embryonic kidney (HEK293T) cells (ATCC #CRL-3216) and African green monkey kidney (Vero-E6) cells (ATCC #CRL-1586) were maintained in Dulbecco's modified Eagle Medium (DMEM) supplemented with 10% fetal bovine serum. SARS-CoV-2, isolate BetaCoV/Singapore/2/2020 (Accession ID EPI ISL 406973), was used for virus neutralization test on Vero-E6 cells as described previously [26].

In Singapore, COVID-19 patient sera used in this study was from the Singapore PROTECT study as described [13]. Sera from recovered SARS patients from 2003 were as previously described [15]. For SARS recall sampling in 2020, the inventor obtained blood from consenting individuals previously admitted for SARS (ethics approval number: NHG DSRB E 2020/00091). The hCoV serum panel included post-infection samples from subjects confirmed CoV 229/NL63 and CoV OC43 positive using the SeeGene RV12 respiratory multiplex kit in a previous study (ethics approval number: NUS-IRB 11-3640) [27]. Negative control sera were obtained from residual serum samples from previous unrelated studies.

In Nanjing, China, COVID-19 convalescent sera were collected with written informed consent and approved by the ethics committee of the Second Hospital of Nanjing (ethics approval number: 2020-LS-ky003). Rabbit anti-SARS-CoV-2 RBD sera were purchased from GenScript. Rabbit and ferret anti-SARS-CoV sera, and alpaca anti-MERS-CoV sera were as described in previous studies [28, 29].

Direct Binding and sVNT Assay

For direct binding, hACE2 protein (GenScript, Cat #: Z03484) was coated at 100 ng/well in 100 mM carbonate-bicarbonate coating buffer (pH 9.6). HRP-conjugated SARS-CoV-2 nucleocapsid (briefly referred to as N hereinafter, GenScript, Cat #: Z03488), S1 (GenScript, Cat #: Z03501), RBD (GenScript, Cat #: Z03479) or HRP-conjugated SARS-CoV-RBD (customer-made by GenScript) was added to the hACE2 coated plate at different concentration in OptEIA assay diluent (BD) for 1 h at room temperature. Unbound HRP-conjugated antigens were removed by five phosphate buffered saline, 0.05% tween-20 (PBST) washes. Colorimetric signal was developed on the enzymatic reaction of HRP with chromogenic substrate, 3,3',5,5'-tetramethylbenzidine (TMB) (Invitrogen). Equal volume of TMB stop solution (KPL) was added to stop the reaction, and the absorbance reading at 450 nm and 570 nm were acquired using Cytation 5 microplate reader (BioTek). For the surrogate neutralization test (sVNT), 6 ng of HRP-RBD (from SARS-CoV or SARS-CoV-2) was pre-incubated with test serum at the final dilution of 1:20 for 1 h at 37° C., followed by hACE2 incubation for 1 h at room temperature. Inhibition (%)=(1−Sample OD value/Negative Control OD value)× 100.

Indirect ELISA

SARS-CoV-2 N protein and SARS-CoV N protein were expressed from the pcDNA3.1 SARS-CoV-2 N and pDualGC SARS-CoV N transfected HEK293T cells and purified using Ni Sepharose (GE healthcare). For indirect ELISA, 100 ng of each protein was coated onto MaxiSORP ELISA plate (Nunc) using 100 mM carbonate buffer and blocked with BD OptEIA (BD). COVID-19 and SARS patient sera were tested at a dilution of 1:50 and detected by Goat-anti-human IgG-HRP (Santa Cruz) at 1:10,000 dilution. The chromogenic signal was developed using TMB substrate (Invitrogen) and the reaction was stop with TMB stop solution (KPL). Absorbance readings at 450 and 570 nm were obtained using Cytation 5 microplate reader (Bio-Tek).

Capture ELISA 96-well Maxisorp plates (Nunc) were coated with 10 μg/ml of anti-human IgM (SeraCare) or anti-human IgG (Jackson labs) in bicarbonate buffer overnight at 4° C. Wells were blocked using BD OptEIA assay diluent (BD) for 1 h at 37° C., and heat-inactivated sera diluted 1:50 were next added and incubated for 1 h at 37° C. Following extensive washing, SARS-CoV-2-RBD-HRP (GenScript) diluted 4 μg/ml was added and incubated for 30 min at 37° C. Chromogenic reaction was quantified following the addition of TMB substrate (Invitrogen) and stop solution (KPL SeraCare). The absorbance of the samples was measured at 450 nm and the background at 570 nm. Negative controls consisted of 37 naïve human sera. Results are presented as fold-change over average reading of negative controls.

Statistical Analysis

Statistical analysis was perform using GraphPad Prism software with the Kruskal-Wallis test to compare multiple groups, followed by Dunn's multiple comparisons test. Data were considered significant if *P<0.05, P<0.01, *P<0.001, ****P<0.0001.

2.3 Results

Figure 6A:
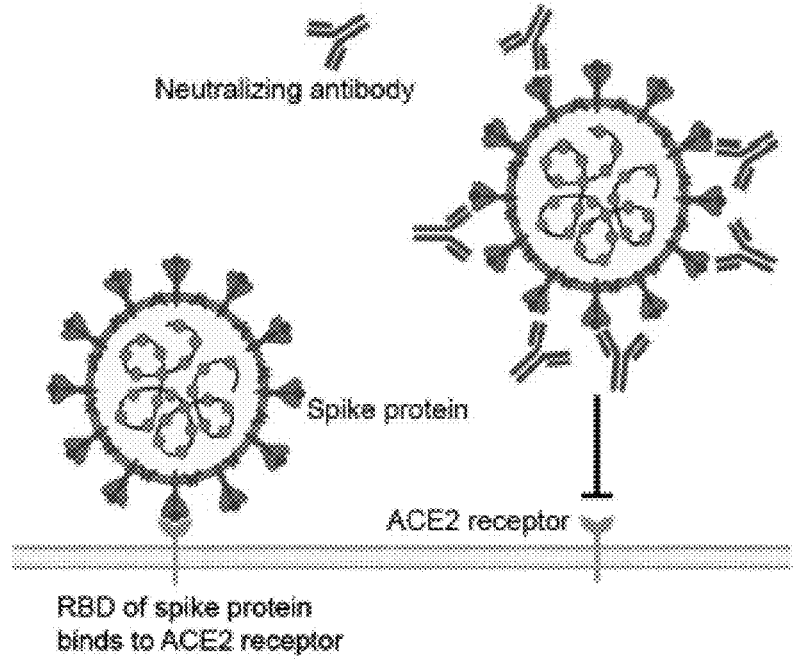
FIGS. 6A to 6F. Schematic representations and graphs showing the principle and initial validation of the SARS-CoV-2 surrogate virus neutralization test (sVNT). (6A) Mechanism of conventional virus neutralization test (VNT). Anti-SARS-CoV-2 neutralizing antibodies block SARS-CoV-2 Spike protein from binding to hACE2 receptor proteins on the host cell surface. (6B) In the sVNT assay, anti-SARS-CoV-2 neutralizing antibodies block HRP-conjugated RBD protein from binding to the hACE2 protein pre-coated on an ELISA plate. (6C) Binding of HRP-conjugated SARS-CoV-2 N, S1 and RBD proteins to hACE2. (6D) Inhibition of SARS-CoV-2 RBD-hACE2 interaction by COVID-19 patient sera. (6E) Binding of HRP-conjugated SARS-CoV RBD to hACE2. (6F) Inhibition of SARS-CoV RBD-hACE2 interaction by SARS patient sera.
Figure 6B:
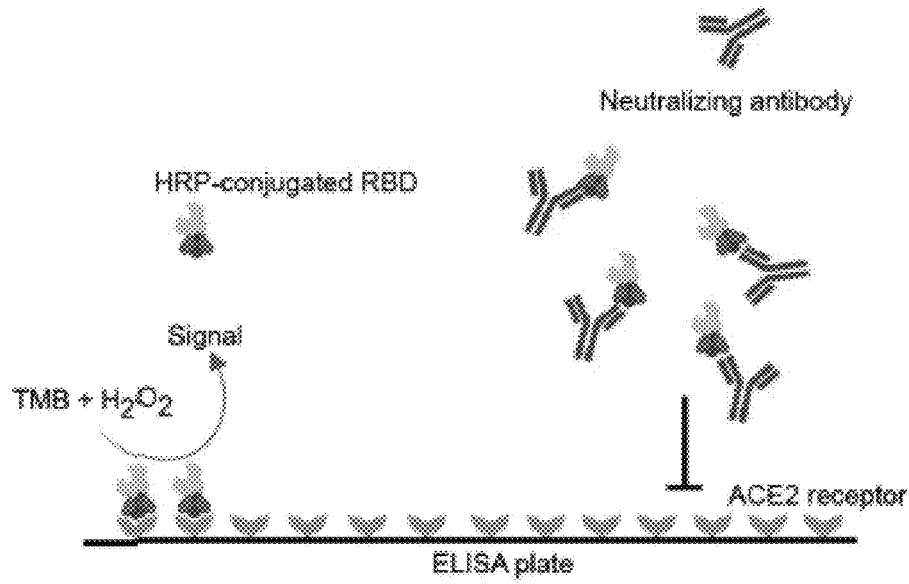

Biochemical Simulation of Virus-Receptor Interaction and Antibody-Mediated Neutralization Immediately after SARS-CoV-2 was identified as the causative agent of the COVID-19 outbreak, it was shown that the human angiotensin converting enzyme-2 (hACE2) is the main functional receptor for viral entry [3]. The inventor hypothesized that the virus-receptor binding can be mimicked in vitro via a protein-protein interaction using purified recombinant hACE2 and the RBD of the SARS-CoV-2 S protein. This interaction can be blocked by virus NAbs present in the test serum, using the same principle as a conventional VNT conducted using live virus inside a BSL3 facility (FIGS. 6A and 6B).

Figure 6C:
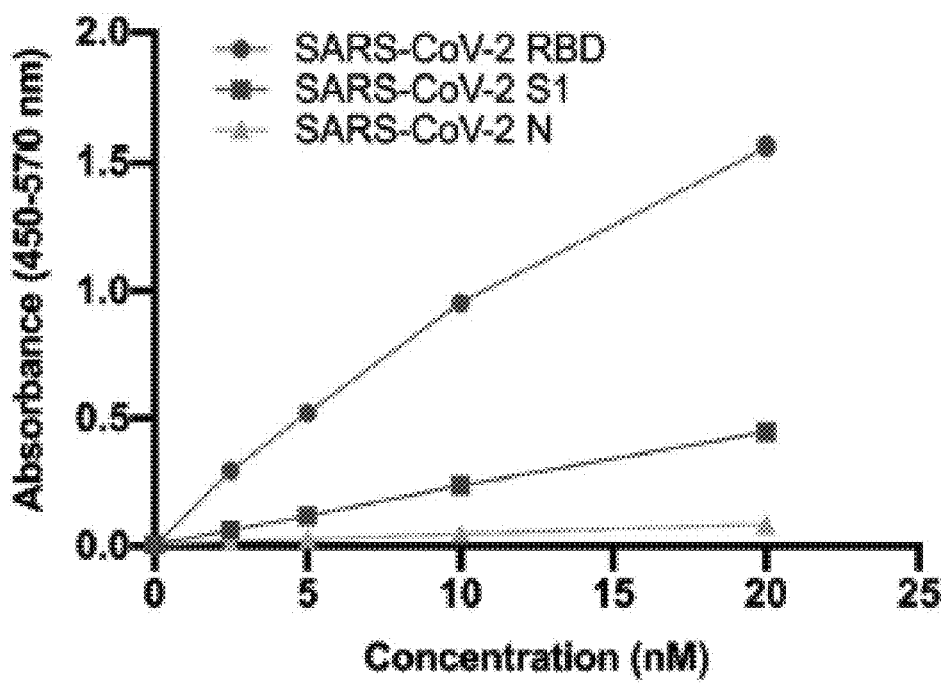
Figure 6D:
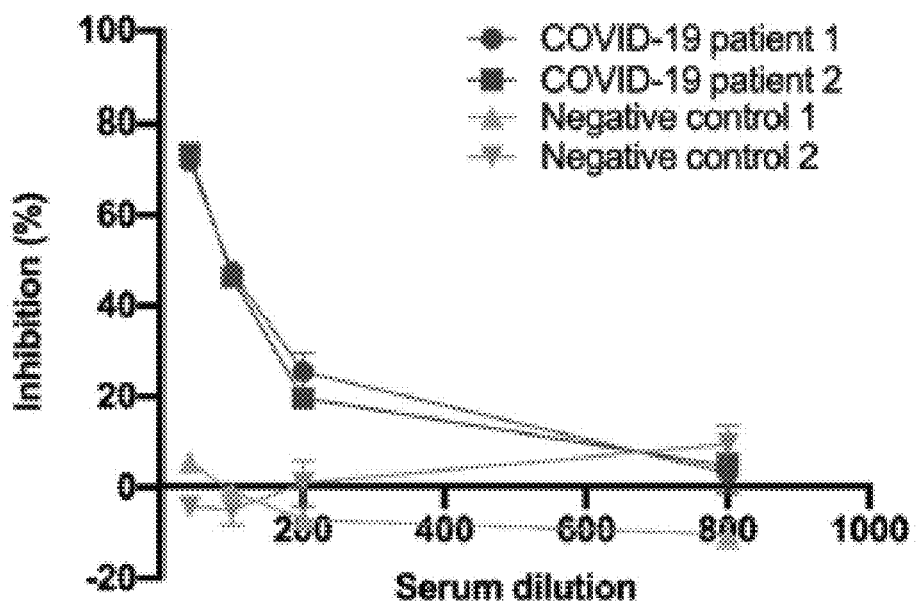
Figure 6E:
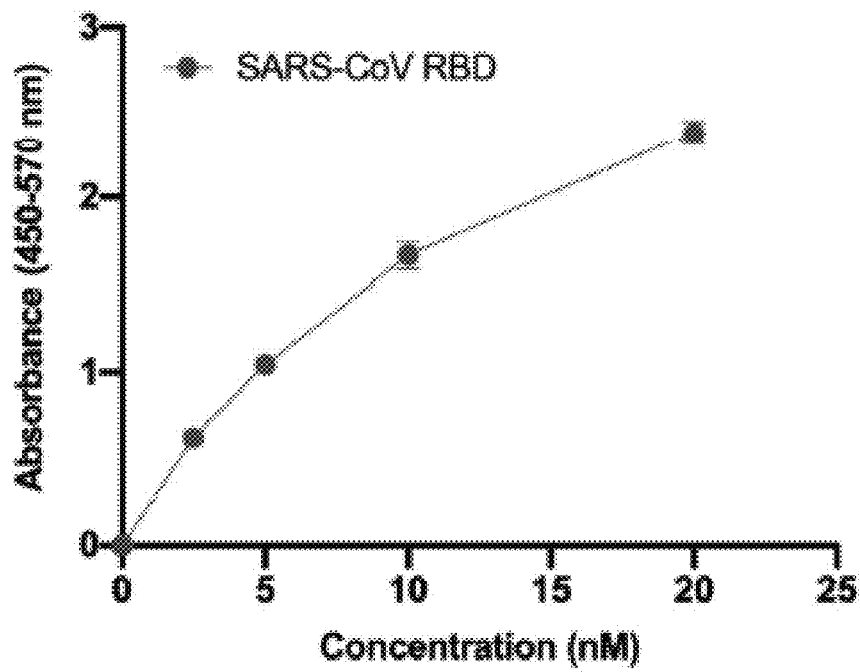
Figure 6F:
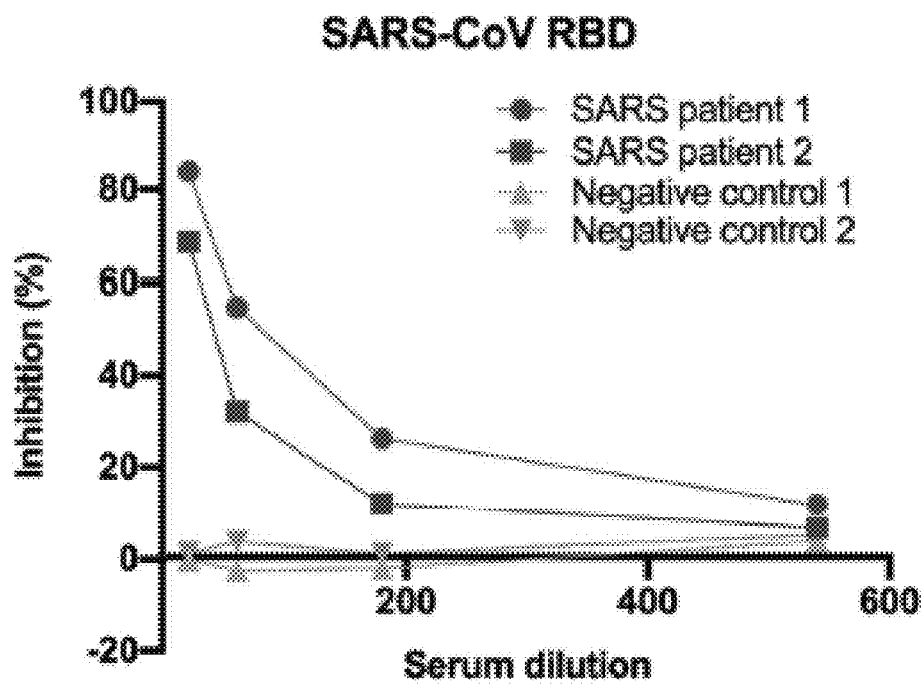

Direct binding was demonstrated using different SARS-CoV-2 proteins conjugated with horseradish peroxidase (HRP). There is a dose-dependent specific binding between hACE2 and RBD or S1, but not with the nucleocapsid (N) protein, with the RBD producing the best binding characteristics (FIG. 6C). The HRP-RBD protein was chosen for subsequent studies. It was then demonstrated that the specific RBD-hACE2 binding can be blocked or neutralized by COVID-19 sera in a dose-dependent manner, but not by sera from healthy controls (FIG. 6D). To prove that the same principle works with the closely related SARS-CoV, which also uses hACE2 as the entry receptor [12], similar experiments were repeated and proved that the SARS-CoV RBD performed in an almost identical manner in this new test format (FIGS. 6E and 6F), termed surrogate virus neutralization test (sVNT).

Isotype- and Species-Independent Neutralization

One of the advantages of the sVNT is its ability to detect total antibodies in patient sera, in contrast to most SARS-CoV-2 antibody tests published or marketed, which are almost all isotype-specific, mostly for IgM or IgG, with some for IgA [9-11]. From a panel of 77 COVID-19 positive sera from patients in Singapore, the inventor has designated four groups based on IgM or IgG ELISA levels, determined by in-house capture ELISA assays (see Methods), present in the patient convalescent sera: a) high IgM/low IgG; b) low IgM/high IgG; c) low IgM/low IgG; and d) high IgM/high IgG. All groups showed strong neutralization activity in the sVNT (FIGS. 7A-7D), demonstrating the isotype-independent performance of the assay. It is worth to note that for panel c with low IgM/IgG, the % inhibition in sVNT is still significant at 70-75%, demonstrating its superior sensitivity as this group of sera were deemed negative or weakly positive with isotype-specific capture ELISA based on IgM or IgG alone.

Figures 8A, 8B:
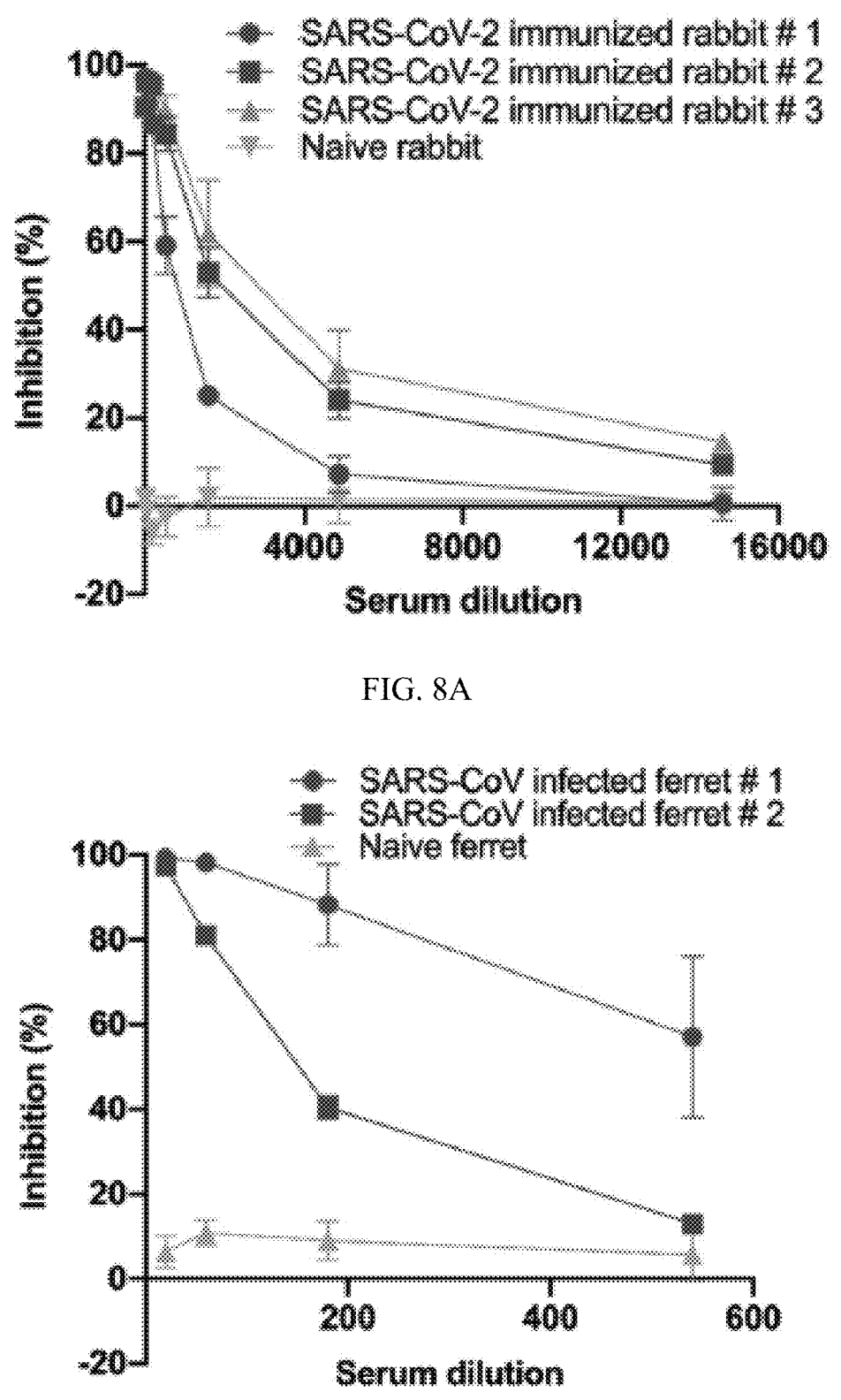

The inventor then tested different animal sera in the sVNT assays to demonstrate species-independent performance. Results from three independent rabbits immunized with the SARS-CoV-2 RBD protein, demonstrate very potent neutralizing activity in the SARS-CoV-2 sVNT (FIG. 8A). Similarly, sera from ferrets infected with SARS-CoV (FIG. 8B) and rabbits immunized with inactivated SARS-CoV (FIG. 8C) also showed an efficient dose-dependent inhibition of the hACE2-SARS-CoV RBD interaction in the SARS-CoV sVNT.

Specificity Against Other hCoVs and Comparison of SARS Sera Collected in 2003 vs 2020

Figures 8C, 8D:
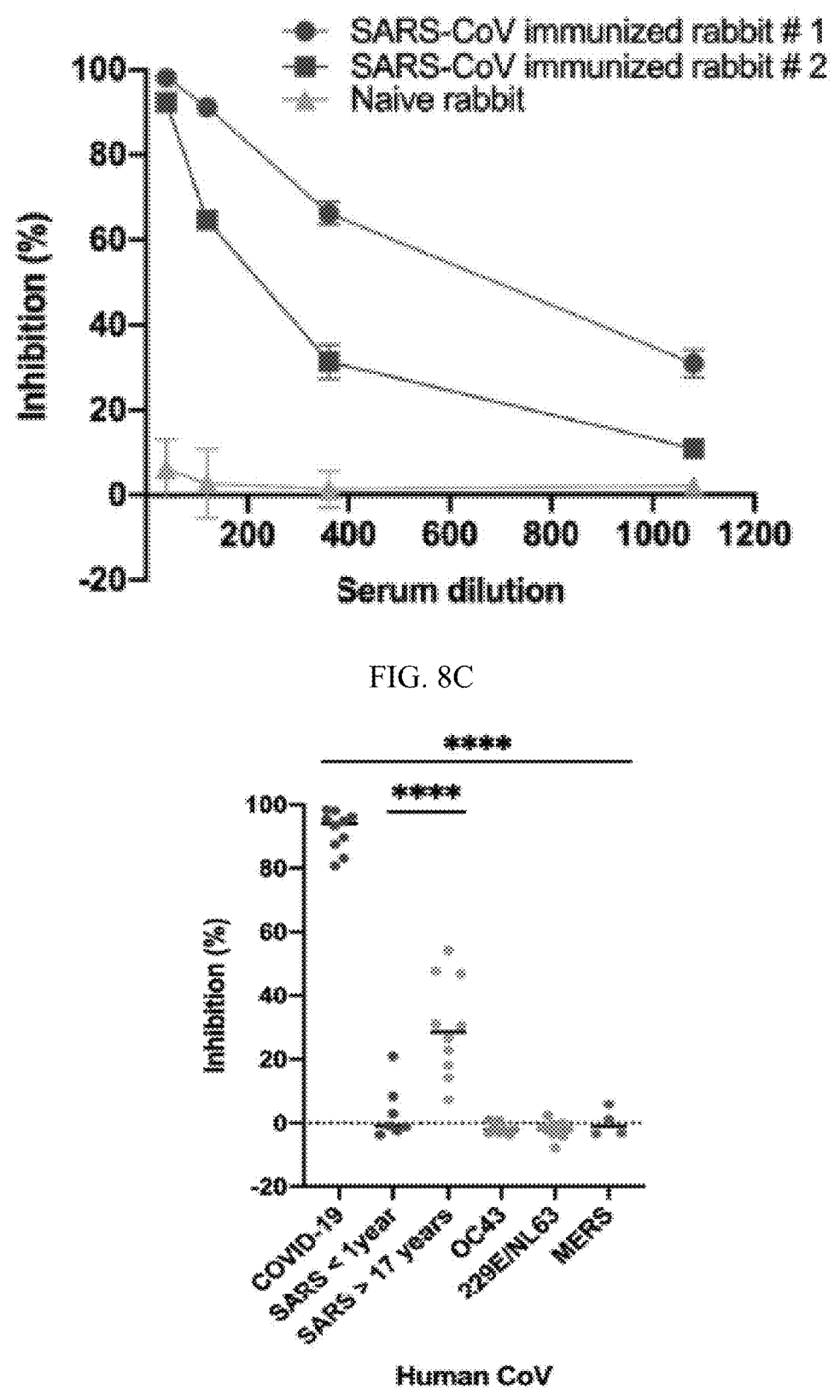

To demonstrate specificity, the inventor tested different panels of sera against other known human coronaviruses (hCoVs) and confirmed that the SARS-CoV-2 sVNT can differentiate antibody responses between COVID-19 and other coronavirus infections (FIG. 8D). For SARS sera, there is some level of cross reactivity as expected from their close genetical relatedness and previous published studies [3, 7]. But the difference in neutralization is statistically significant, and hence the sVNT can be used to differentiate SARS-CoV-2 infection from past SARS infection. For human sera from patients with 229/NL63 or OC43 infection and alpaca sera from experimental MERS-CoV infection, there is no detectable cross neutralization.

Figure 8E:
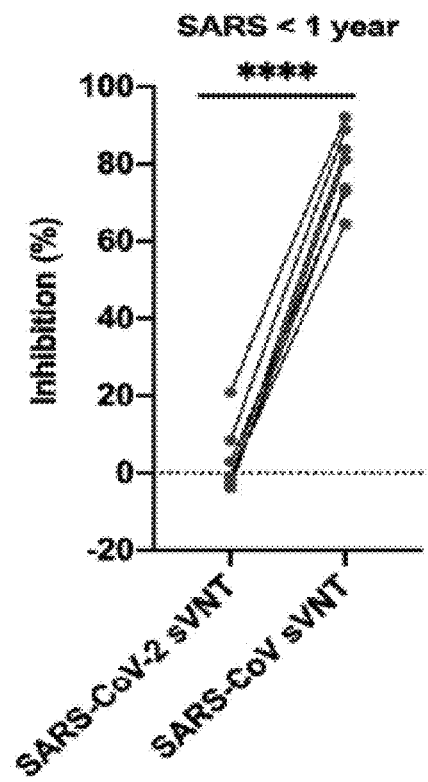
Figure 8F:
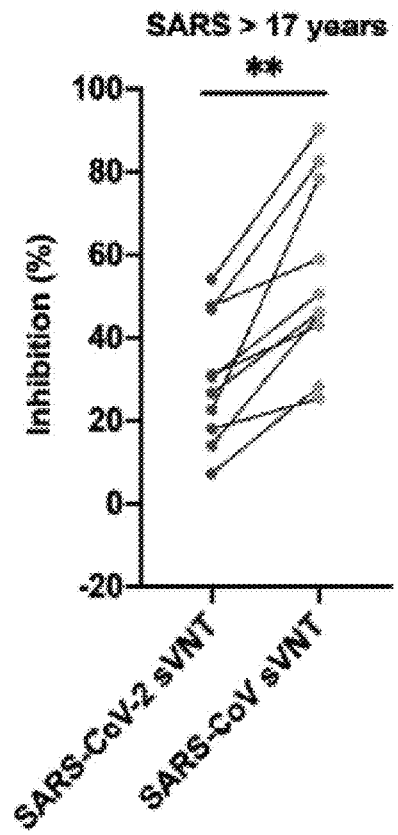
Figure 8G:
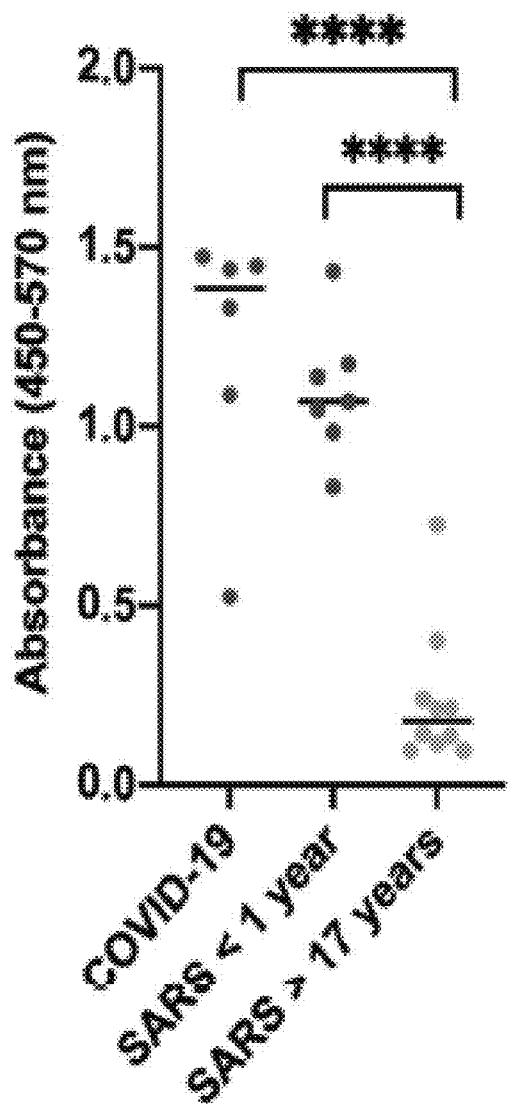

During the investigation of potential cross reactivity between SARS sera and SARS-CoV-2 virus, several important observations were made. Firstly, despite the lack of cross neutralization by SARS sera against the live SARS-CoV-2 virus in VNT observed by us and other groups [13], some level of cross neutralization in sVNT was detected (FIG. 8D), indicating sVNT is more sensitive than VNT. Secondly, SARS NAbs are detectable for at least 17 years in recovered patients (FIG. 8F). Thirdly, the cross neutralization level is higher in the 2020 SARS sera than the 2003 samples (FIG. 8D) although the homologous neutralizing level of the 2020 SARS sera (FIG. 8F) is lower than the 2003 SARS sera (FIG. 8E). Lastly, the N-specific antibody level was found to be much lower in the 2020 SARS sera than the 2003 samples (FIG. 8G).

Correlation Between Live Virus VNT and Biochemical sVNT

Figure 9A:
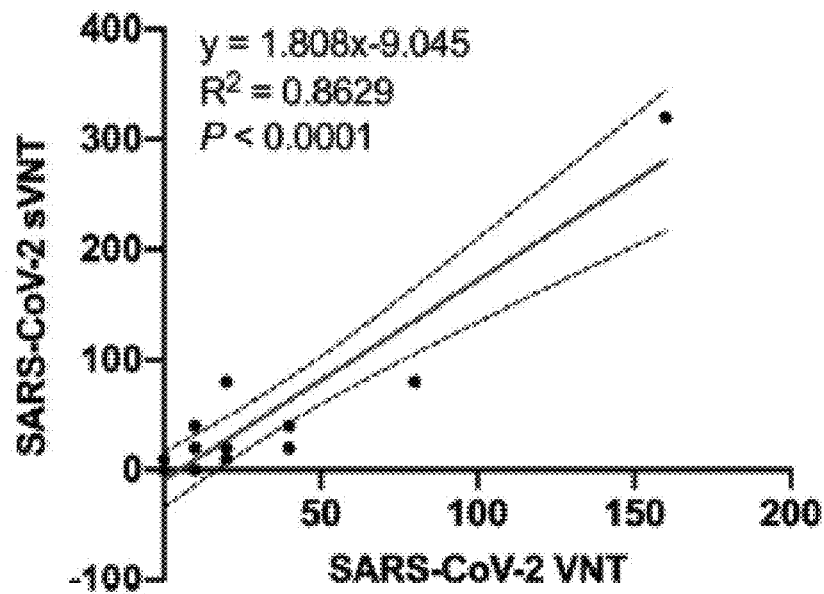
FIGS. 9A to 9C. Correlation between sVNT and VNT and sVNT testing with two COVID-19 patient cohorts from two different nations. (9A) Correlation analysis for 13 COVID-19 sera with different levels of SARS-CoV-2 antibodies by VNT and sVNT at 70% inhibition. Testing of healthy control and COVID-19 serum cohorts in Singapore (9B) (COVID-19 n=77, control n=75) and Nanjing, China (9C) (COVID-19 n=50, control n=50).
Figure 9B:
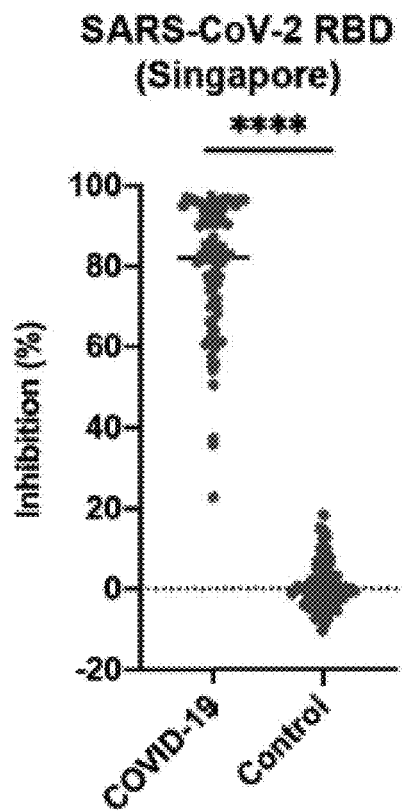
Figures 9C, 10:
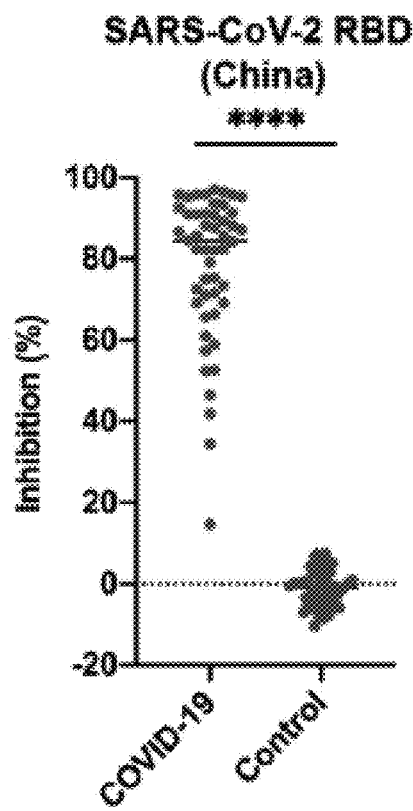
FIG. 10. Table showing correlation between VNT and sVNT for different COVID-19 sera. Neutralization titers were obtained from two biological replicates each with two technical replicates. sVNT titers at 90%, 70%, 50% and 30% inhibition, respectively, are shown.
Figure 11:
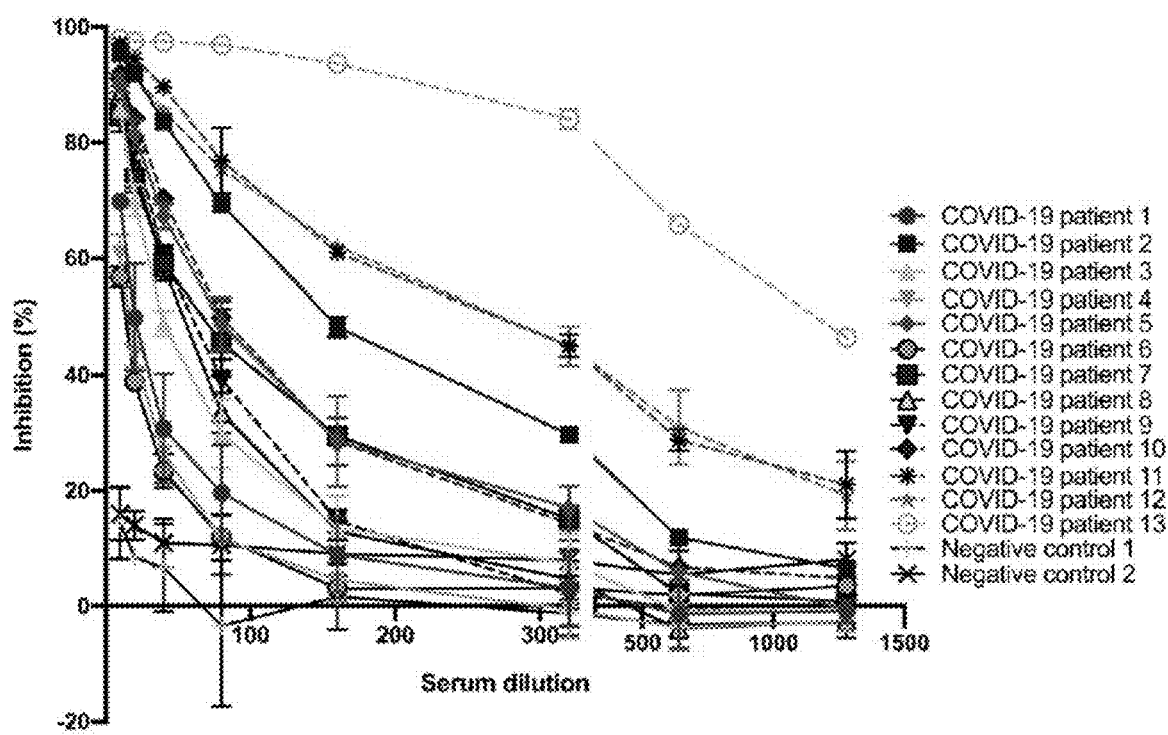
FIG. 11. Graph showing titration of COVID-19 sera with 417 different levels of SARS-CoV-2 antibodies. Serum samples were two-fold diluted starting at 1:10. Percentage inhibition was plotted at each dilution point for two negative controls and 13 COVID-19 sera from PCR positive patients.

A panel of COVID-19 sera with different levels of SARS-CoV-2 NAbs as shown by sVNT (FIG. 11) were chosen for a comparative and correlation study between the live virus based VNT and the RBD-hACE2 based sVNT. The results demonstrate good overall correlation between the two assays (FIG. 9A and FIG. 10). The SARS-CoV-2 sVNT is more sensitive than VNT. At the 50% inhibition cutoff, which is considered a stringent cutoff as evident from the titration curves in FIG. 11, all COVID-19 patient sera showed neutralization at 1:20 or greater with the COVID-19 Patient 13 serum reaching a neutralization titer equal to or greater than 640 (FIG. 11).

Validation with Two Cohorts of Positive and Negative Sera from Two Countries

To validate the performance of the SARS-CoV-2 sVNT, two different cohorts of positive and negative sera were analysed. The assay was performed in two different countries by two independent groups to further assure reliability and reproducibility. For the first cohort, 77 sera from PCR-confirmed COVID-19 patients in Singapore collected on days 14-33 after symptom onset and 75 healthy control sera were tested. All control sera were negative, resulting in a 100% specificity. Using a cutoff at 20% inhibition, the assay sensitivity is at 100%. The sensitivity decreases to 95.6% when a 40% cutoff is used (FIG. 9B). For the second cohort, 50 sera each of healthy controls and PCR-confirmed COVID-19 patients in Nanjing, China, sampled on days 27-61 after symptom onset were tested. The specificity is 100%. The sensitivity is 98% and 96% using a 20% and 40% cutoff, respectively (FIG. 9C).

2.3 Discussion

We are more than 100 days into the COVID-19 outbreak and attention worldwide, both in the scientific community and for policy makers, has shifted focus from acute diagnostic strategy and capacity to the use of serology for the "exit strategy", relying on accurate assessment of infection prevalence at the individual and population (herd) level. Discussion and debate on the role of serology has intensified greatly in this context [6].

While there are many COVID-19 lab-based or point-of-care (POC) antibody test kits commercially available, none are capable of measuring NAbs. VNT or pVNT remain the only platform for detection of NAbs. Both require live virus and cells, highly skilled operators, are less sensitive in general, and take days to obtain results. VNT and pVNT are thus not suitable for mass production and testing, even in the most developed nations.

The World Health Organization (WHO) has recently cautioned that positive results from antibody tests do not equal to protective immunity [14] due to two aspects or obstacles. Firstly, most, if not all, current testing done at large scale is for detection of binding antibodies only and does not measure NAbs; secondly, the presence of NAbs may or may not correlate with protection. While the second aspect will take much more in-depth scientific and clinical research to resolve in the specific context of COVID-19 infection, past experiences with viral infection in general argue that in most recovered patients NAb level is a good indicator of protective immunity, despite the fact that some patients may not obey this "rule of thumb" [15, 16]. In this Example, the inventor describes a novel sVNT platform to tackle the first obstacle.

The data presented here demonstrated that sVNT is as specific as, and more sensitive than VNT. The results obtained from sVNT correlates well with VNT. The major advantage of sVNT is that it can be rapidly conducted in most research or clinical labs without the need to use live biological materials and biosafety containment. The sVNT is also amenable to high throughput testing and/or fully automated testing after minimal adaptation.

Another advantage of sVNT is its ability to detect SARS-CoV-2 antibodies in a species-independent manner. As the origin of SARS-CoV-2 and early transmission event remain elusive, the sVNT assay will be ideally suited for "virus hunting" as past studies have amply demonstrated that serological surveys are more superior than molecular detection as the virus-specific antibodies last much longer in animals than the viral genetic material [17-19]. Sampling serum for antibody detection is also more reliable than other sampling approaches used for molecular detection as the target tissues can vary from virus to virus [20-22].

Figure 7A:
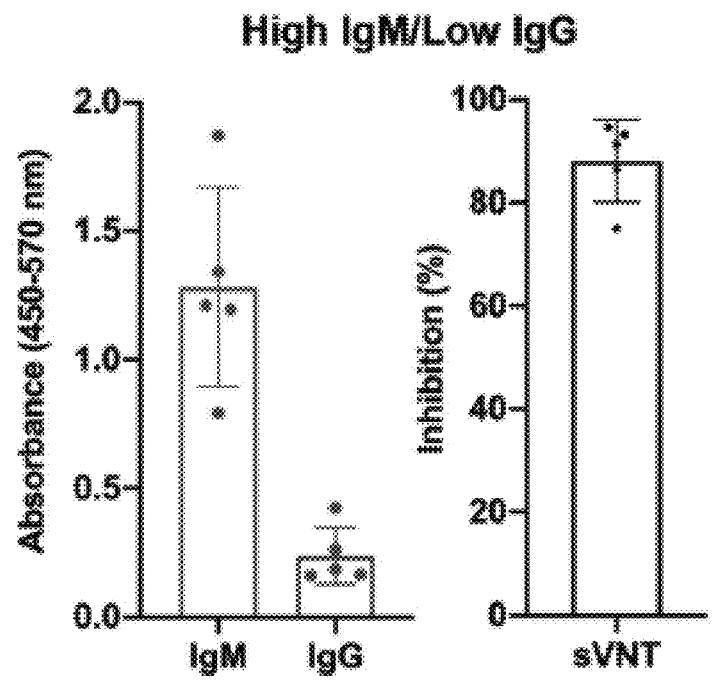
FIGS. 7A to 7D. Bar charts showing isotype-independent neutralization by human sera with different levels of IgM and IgG antibodies. (7A) High IgM/Low IgG (n=5); (7B) Low IgM/High IgG (n=3); (7C) Low IgM/Low IgG (n=9); (7D) High IgM/High IgG (n=5). The IgM and IgG levels were determined by isotype-specific capture ELISA.
Figure 7B:
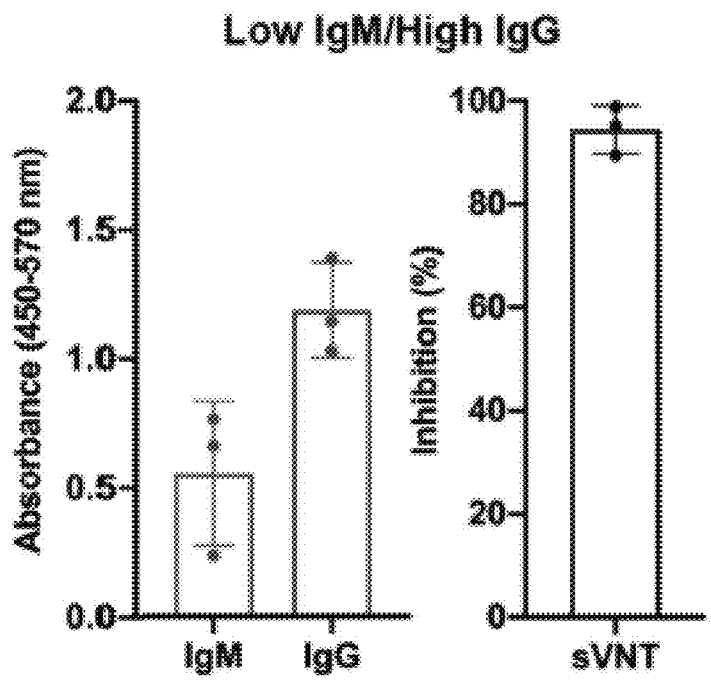
Figure 7C:
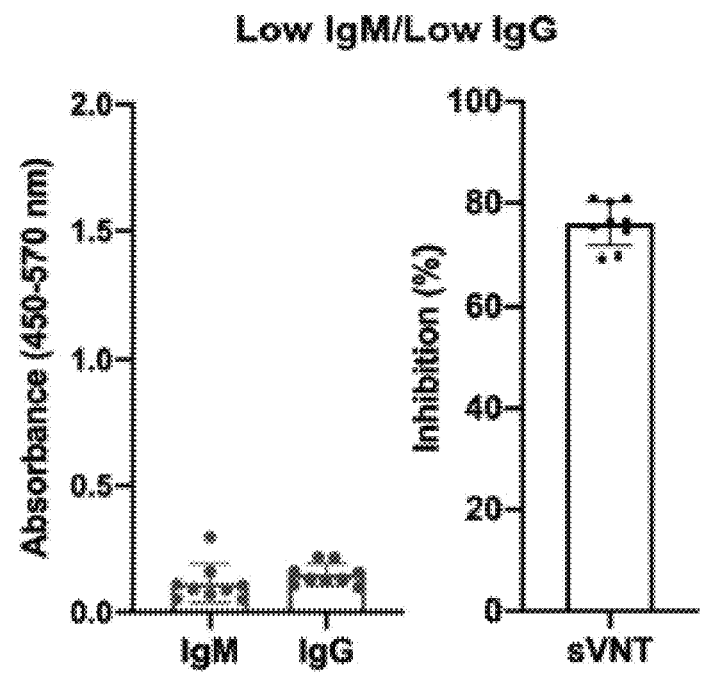
Figure 7D:
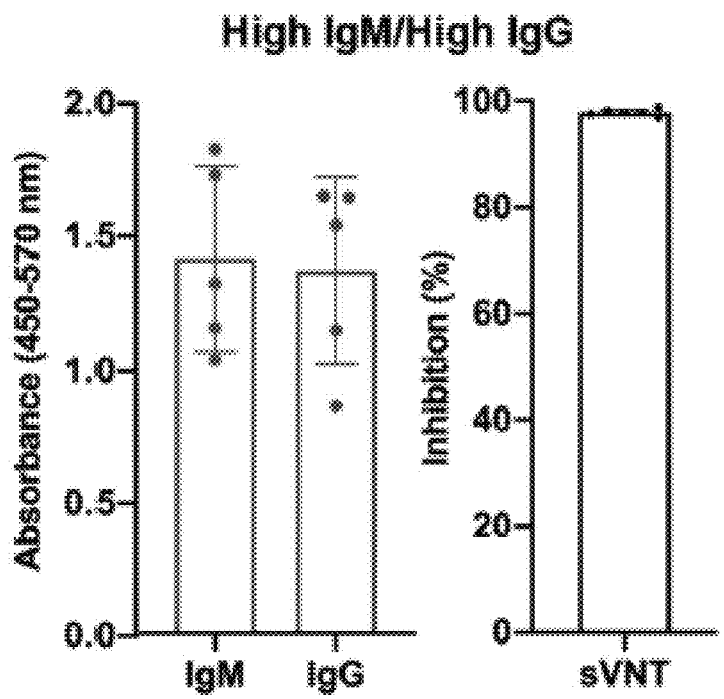

In addition, sVNT offers a key advantage over most ELISA or POC tests in its ability to detect total NAbs in an isotype-independent manner. This will not only simplify the testing strategy, but also further increase test sensitivity. As shown in FIG. 7C for the serum panel of COVID-19 patients showing low IgM and IgG in the isotype-specific ELISAs, the sVNT assay still detected significant level of NAbs. Although the mechanism needs further investigation, there are at least two possibilities: the presence of other Ig isotypes or neutralization synergy or cooperativity from the combination of different isotype antibodies targeting different neutralization critical epitopes, as previously observed for HIV and other viruses [23-25].

Results obtained for the two SARS serum panels are very interesting. The long lasting NAbs 17 years after initial infection is encouraging news for recovered COVID-19 patients considering the close relationship of the two viruses. The mechanism and biological significance of the increased cross neutralization towards SARS-COV-2 coupled with the decrease/disappearance of N-specific antibodies 17 years after infection warrants further investigation in the context of better understanding SARSr-CoV immune response dynamics.

In summary, the inventor has addressed the challenge of COVID-19 serology with a new approach that enables the detection of NAbs in an easy, safe, rapid and inexpensive manner with enhanced specificity and sensitivity. The data indicate that their performance is generally well correlated. Its application can cover many aspects of COVID-19 investigation from contact tracing, sero-prevalence survey, reservoir/intermediate animal tracking to assessment of herd immunity, longevity of protective immunity and efficacy of different vaccine candidates.

Exemplary sequences of the disclosure are set forth below.

| SEQ ID NO: | DESCRIPTION | SEQUENCE |
|---|---|---|
| 1 | SARS-CoV spike protein | MFIFLLFLTLTSGSDLDRCTTFDDVQAPNYTQHTSSMRGVYYPDEIFRSDTLYLTQDLFLPFY SNVTGFHTINHTFDNPVIPFKDGIYFAATEKSNVVRGWVFGSTMNNKSQSVIIINNSTNVVIR ACNFELCDNPFFAVSKPMGTQTHTMIFDNAFNCTFEYISDAFSLDVSEKSGNFKHLREFVFK NKDGFLYVYKGYQPIDVVRDLPSGFNTLKPIFKLPLGINITNFRAILTAFSPAQDTWGTSAAA YFVGYLKPTTFMLKYDENGTITDAVDCSQNPLAELKCSVKSIAEIDKGIYQTSNFRVVPSGDV VRFPNITNLCPFGEVFNATKFPSVYAWERKKISNCVADYSVLYNSTFFSTFKCYGVSATKLN DLCFSNVYADSFVVKGDDVRQIAPGQTGVIADYNYKLPDDFMGCVLAWNTRNIDATSTGN YNYKYRYLRHGKLRPFERDISNVPFSPDGKPCTPPALNCYWPLNDYGFYTTTGIGYQPYRV VVLSFELLNAPATVCGPKLSTDLIKNQCVNFNFNGLTGTGVLTPSSKRFQPFQQFGRDVSDF TDSVRDPKTSEILDISPCSFGGVSVITPGTNASSEVAVLYQDVNCTDVSTAIHADQLTPAWRI YSTGNNVFQTQAGCLIGAEHVDTSYECDIPIGAGICASYHTVSLLRSTSQKSIVAYTMSLGAD SSIAYSNNTIAIPTNFSISITTEVMPVSMAKTSVDCNMYICGDSTECANLLLQYGSFCTQLNRA LSGIAAEQDRNTREVFAQVKQMYKTPTLKYFGGFNFSQILPDPLKPTKRSFIEDLLFNKVTLA DAGFMKQYGECLGDINARDLICAQKFNGLTVLPPLLTDDMIAAYTAALVSGTATAGWTFG AGAALQIPFAMQMAYRFNGIGVTQNVLYENQKQIANQFNKAISQIQESLTTTSTALGKLQD VVNQNAQALNTLVKQLSSNFGAISSVLNDILSRLDKVEAEVQIDRLITGRLQSLQTYVTQQLI RAAEIRASANLAATKMSECVLGQSKRVDFCGKGYHLMSFPQAAPHGVVFLHVTYVPSQER NFTTAPAICHEGKAYFPREGVFVFNGTSWFITQRNFFSPQIITTDNTFVSGNCDVVIGIINNTV YDPLQPELDSFKEELDKYFKNHTSPDVDLGDISGINASVVNIQKEIDRLNEVAKNLNESLIDL QELGKYEQYIKWPWYVWLGFIAGLIAIVMVTILLCCMTSCCSCLKGACSCGSCCKFDEDDS EPVLKGVKLHYT |
| 2 | SARS-CoV envelope protein | MYSFVSEETGTLIVNSVLLFLAFVVFLLVTLAILTALRLCAYCCNIVNVSLVKPTVYVYSRV KNLNSSEGVPDLLV |
| 3 | SARS-CoV membrane protein | MADNGTITVEELKQLLEQWNLVIGFLFLAWIMLLQFAYSNRNRFLYIIKLVFLWLLWPVTL ACFVLAAVYRINWVTGGIAIAMACIVGLMWLSYFVASFRLFARTRSMWSFNPETNILLNVP LRGTIVTRPLMESELVIGAVIIRGHLRMAGHSLGRCDIKDLPKEITVATSRTLSYYKLGASQR VGTDSGFAAYNRYRIGNYKLNTDHAGSNDNIALLVQ |
| 4 | SARS-CoV nucleocapsid protein | MSDNGPQSNQRSAPRITFGGPTDSTDNNQNGGRNGARPKQRRPQGLPNNTASWFTALTQH GKEELRFPRGQGVPINTNSGPDDQIGYYRRATRRVRGGDGKMKELSPRWYFYYLGTGPEAS LPYGANKEGIVWVATEGALNTPKDHIGTRNPNNNAATVLQLPQGTTLPKGFYAEGSRGGSQ ASSRSSSRSRGNSRNSTPGSSRGNSPARMASGGGETALALLLLDRLNQLESKVSGKGQQQQ GQTVTKKSAAEASKKPRQKRTATKQYNVTQAFGRRGPEQTQGNFGDQDLIRQGTDYKHW PQIAQFAPSASAFFGMSRIGMEVTPSGTWLTYHGAIKLDDKDPQFKDNVILLNKHIDAYKTF PPTEPKKDKKKKTDEAQPLPQRQKKQPTVTLLPAADMDDFSRQLQNSMSGASADSTQA |
| 5 | SARS-CoV-2 spike protein | MFLLTTKRTMFVFLVLLPLVSSQCVNLTTRTQLPPAYTNSFTRGVYYPDKVFRSSVLHSTQD LFLPFFSNVTWFHAIHVSGTNGTKRFDNPVLPFNDGVYFASTEKSNIIRGWIFGTTLDSKTQS LLIVNNATNVVVKVCEFQFCNDPFLGVYYHKNNKSWMESEFRVYSSANNCTFEYVSQPFLM DLEGKQGNFKNLREFVFKNIDGYFKIYSKHTPINLVRDLPQGFSALEPLVDLPIGINITRFQTL LALHRSYLTPGDSSSGWTAGAAAYYVGYLQPRTFLLKYNENGTITDAVDCALDPLSETKCT LKSFTVEKGIYQTSNFRVQPTESIVRFPNITNLCPFGEVFNATRFASVYAWNRKRISNCVADY SVLYNSASFSTFKCYGVSPTKLNDLCFTNVYADSFVIRGDEVRQIAPGQTGKIADYNYKLPD DFTGCVIAWNSNNLDSKVGGNYNYLYRLFRKSNLKPFERDISTEIYQAGSTPCNGVEGFNC YFPLQSYGFQPTNGVGYQPYRVVVLSFELLHAPATVCGPKKSTNLVKNKCVNFNFNGLTGT GVLTESNKKFLPFQQFGRDIADTTDAVRDPQTLEILDITPCSFGGVSVITPGTNTSNQVAVLY QDVNCTEVPVAIHADQLTPTWRVYSTGSNVFQTRAGCLIGAEHVNNSYECDIPIGAGICASY QTQTNSPRRARSVASQSIIAYTMSLGAENSVAYSNNSIAIPTNFTISVTTEILPVSMTKTSVDC TMYICGDSTECSNLLLQYGSFCTQLNRALTGIAVEQDKNTQEVFAQVKQIYKTPPIKDFGGF NFSQILPDPSKPSKRSFIEDLLFNKVTLADAGFEKYGDCLGDIAARDLICAQKFNGLTVLPPL LTDEMIAQYTSALLAGTITSGWTFGAGAALQIPFAMQMAYRFNGIGVTQNVLYENQKLIAN QFNSAIGKIQDSLSSTASALGKLQDVVNQNAQALNTLVKQLSSNFGAISSVLNDILSRLDKV EAEVQIDRLITGRLQSLQTYVTQQLIRAAEIRASANLAATKMSECVLGQSKRVDFCGKGYHL MSFPQSAPHGVVFLHVTYVPAQEKNFTTAPAICHDGKAHFPREGVFVSNGTHWFVTQRNFY EPQIITTDNTFVSGNCDVVIGIVNNTVYDPLQPELDSFKEELDKYFKNHTSPDVDLGDISGIN |

| SEQ ID NO: | DESCRIPTION | SEQUENCE |
|---|---|---|
|  |  | ASVVNIQKEIDRLNEVAKNLNESLIDLQELGKYEQYEKWPWYIWLGFIAGLIAIVMVTIMLC CMTSCCSCLKGCCSCGSCCKFDEDDSEPVLKGVKLHYT |
| 6 | SARS-CoV-2 envelope protein | MYSFVSEETGTLIVNSVLLFLAFVVFLLVTLAILTALRLCAYCCNIVNVSLVKPSFYVYSRVK NLNSSRVPDLLV |
| 7 | SARS-CoV-2 membrane protein | MADSNGTITVEELKKLLEQWNLVIGFLFLTWICLLQFAYANRNRFLYIIKLIFLWLLWPVTL ACFVLAAVYRINVVITGGIAIAMACLVGLMWLSYFIASFRLFARTRSIVIWSFNPETNILLNVPL HGTILTRPLLESELVIGAVILRGHLRIAGHHLGRCDIKDLPKEITVATSRTLSYYKLGASQRVA GDSGFAAYSRYRIGNYKLNTDHSSSSDNIALLVQ |
| 8 | SARS-CoV-2 nucleocapsid protein | MSDNGPQNQRNAPRITFGGPSDSTGSNQNGERSGARSKQRRPQGLPNNTASWFTALTQHGK EDLKFPRGQGVPINTNSSPDDQIGYYRRATRRIRGGDGKMKDLSPRWYFYYLGTGPEAGLP YGANKDGIIWVATEGALNTPKDHIGTRNPANNAAIVLQLPQGTTLPKGFYAEGSRGGSQAS SRSSSRSRNSSRNSTPGSSRGTSPARMAGNGGDAALALLLLDRLNQLESKMSGKGQQQQGQ TVTKKSAAEASKKPRQKRTATKAYNVTQAFGRRGPEQTQGNFGDQELIRQGTDYKHWPQI AQFAPSASAFFGMSRIGMEVTPSGTWLTYTGAEKLDDKDPNFKDQVILLNKHIDAYKTFPPT EPKKDKKKKADETQALPQRQKKQQTVTLLPAADLDDFSKQLQQSMSSADSTQA |
| 9 | SARS-CoV spike protein S1 subunit | SDLDRCTTFDDVQAPNYTQHTSSMRGVYYPDEIFRSDTLYLTQDLFLPFYSNVTGFHTINHT FDNPVIPFKDGIYFAATEKSNVVRGWVFGSTMNNKSQSVIIINNSTNVVIRACNFELCDNPFF AVSKPMGTQTHTM1FDNAFNCTFEYISDAFSLDVSEKSGNFKHLREFVFKNKDGFLYVYKG YQPIDVVRDLPSGFNTLKPIFKLPLGINITNFRAILTAFSPAQDTVVGTSAAAYFVGYLKPTTF MLKYDENGTITDAVDCSQNPLAELKCSVKSFEEDKGIYQTSNFRVVPSGDVVRFPNITNLCPF GEVFNATKFPSVYAWERKKISNCVADYSVLYNSTFFSTFKCYGVSATKLNDLCFSNVYADS FVVKGDDVRQIAPGQTGVIADYNYKLPDDFMGCVLAWNTRNEDATSTGNYNYKYRYLRH GKLRPFERDISNVPFSPDGKPCTPPALNCYWPLNDYGFYTTTGIGYQPYRVVVLSFELLNAP ATVCGPKLSTDLEKNQCVNFNFNGLTGTGVLTPSSKRFQPFQQFGRDVSDFTDSVRDPKTSEI LDISPCSFGGVSVITPGTNASSEVAVLYQDVNCTDVSTAIHADQLTPAWRIYSTGNNVFQTQ AGCLIGAEHVDTSYECDIPIGAGICASYHTVSLLR |
| 10 | SARS-CoV spike protein RBD | RVVPSGDVVRFPNITNLCPFGEVFNATKFPSVYAWERKKISNCVADYSVLYNSTFFSTFKCY GVSATKLNDLCFSNVYADSFVVKGDDVRQIAPGQTGVIADYNYKLPDDFMGCVLAWNTR NIDATSTGNYNYKYRYLRHGKLRPFERDISNVPFSPDGKPCTPPALNCYWPLNDYGFYTTTG IGYQPYRVVVLSFELLNAPATVCGPKLSTDLIKNQCVNF |
| 11 | SARS-CoV spike protein RBM | NTRNIDATSTGNYNYKYRYLRHGKLRPFERDISNVPFSPDGKPCTPPALNCYWPLNDYGFY TTTGIGYQPY |
| 12 | SARS-CoV-2 spike protein S1 subunit | SQCVNLTTRTQLPPAYTNSFTRGVYYPDKVFRSSVLHSTQDLFLPFFSNVTVVFHAIHVSGTN GTKRFDNPVLPFNDGVYFASTEKSNIIRGWIFGTTLDSKTQSLLIVNNATNVVIKVCEFQFCN DPFLGVYYHKNNKSWMESEFRVYSSANNCTFEYVSQPFLMDLEGKQGNFKNLREFVFKNI DGYFKIYSKHTPINLVRDLPQGFSALEPLVDLPIGINITRFQTLLALHRSYLTPGDSSSGWTAG AAAYYVGYLQPRTFLLKYNENGTITDAVDCALDPLSETKCTLKSFTVEKGIYQTSNFRVQPT ESIVRFPNITNLCPFGEVFNATRFASVYAWNRKRISNCVADYSVLYNSASFSTFKCYGVSPTK LNDLCFTNVYADSFV1RGDEVRQIAPGQTGKIADYNYKLPDDFTGCVIAWNSNNLDSKVGG NYNYLYRLFRKSNLKPFERDISTEIYQAGSTPCNGVEGFNCYFPLQSYGFQPTNGVGYQPYR VVVLSFELLHAPATVCGPKKSTNLVKNKCVNFNFNGLTGTGVLTESNKKFLPFQQFGRDIA DTTDAVRDPQTLEILDITPCSFGGVSVITPGTNTSNQVAVLYQDVNCTEVPVAIHADQLTPT WRVYSTGSNVFQTRAGCLIGAEHVNNSYECDIPIGAGICASYQTQTNSPRRAR |
| 13 | SARS-CoV-2 spike protein RBD | RVQPTESIVRFPNITNLCPFGEVFNATRFASVYAWNRKRISNCVADYSVLYNSASFSTFKCY GVSPTKLNDLCFTNVYADSFVIRGDEVRQIAPGQTGKIADYNYKLPDDFTGCVIAWNSNNL DSKVGGNYNYLYRLFRKSNLKPFERDISTEIYQAGSTPCNGVEGFNCYFPLQSYGFQPTNGV GYQPYRVVVLSFELLHAPATVCGPKKSTNLVKNKCVNF |
| 14 | SARS-CoV-2 spike protein RBM | NSNNLDSKVGGNYNYLYRLFRKSNLKREERDISTEIYQAGSTPCNGVEGFNCYFPLQSYGFQ PTNGVGYQPY |
| 15 | Human ACE2 isoform 1 | MSSSSWLLLSLVAVTAAQSTIEEQAKTFLDKFNHEAEDLFYQSSLASWNYNTNITEENVQN MNNAGDKWSAFLKEQSTLAQMYPLQEIQNLTVKLQLQALQQNGSSVLSEDKSKRLNTILN TMSTIYSTGKVCNPDNPQECLLLEPGLNEIMANSLDYNERLWAWESWRSEVGKQLRPLYEE YVVLKNEMARANHYEDYGDYWRGDYEVNGVDGYDYSRGQLIEDVEHTFEEEKPLYEHLH AYVRAKLMNAYPSYISPIGCLPAHLLGDMWGRFWTNLYSLTVPFGQKPNEDVTDAMVDQA WDAQRIFKEAEKFFVSVGLPNMTQGFWENSMLTDPGNVQKAVCHPTAWDLGKGDFRILM CTKVTMDDFLTAHHEMGHIQYDMAYAAQPFLLRNGANEGFHEAVGEIMSLSAATPKHLKS IGLLSPDFQEDNETEINFLLKQALTIVGTLPFTYMLEKWRWMVFKGEIPKDQWMKKWWEM KREIVGVVEPVPHDETYCDPASLFHVSNDYSFIRYYTRTLYQFQFQEALCQAAKHEGPLHKC DISNSTEAGQKLFNMLRLGKSEPWTLALENVVGAKNMNVRPLLNYFEPLFTWLKDQNKNS FVGWSTDWSPYADQSEKVRISLKSALGDKAYEWNDNEMYLFRSSVAYAMRQYFLKVKNQ MILFGEEDVRVANLKPRISFNFFVTAPKNVSDIIPRTEVEKAIRMSRSRINDAFRLNDNSLEFL GIQPTLGPPNQPPVSIWLIVFGVVMGVIVVGIVILIFTGIRDRKKKNKARSGENPYASEDISKGE NNPGFQNTDDVQTSF |

| SEQ ID NO: | DESCRIPTION | SEQUENCE |
|---|---|---|
| 16 | Human ACE2 isoform 2 | MSSSSWLLLSLVAVTAAQSTIEEQAKTFLDKFNHEAEDLFYQSSLASWNYNTNITEENVQN MNNAGDKWSAFLKEQSTLAQMYPLQEIQNLTVKLQLQALQQNGSSVLSEDKSKRLNTILN TMSTIYSTGKVCNPDNPQECLLLEPGLNEIMANSLDYNERLWAWESWRSEVGKQLRPLYEE YVVLKNEMARANHYEDYGDYWRGDYEVNGVDGYDYSRGQLIEDVEHTFEEEKPLYEHLH AYVRAKLMNAYPSYISPIGCLPAHLLGDMWGRFWTNLYSLTVPFGQKPNEDVTDAMVDQA WDAQRIFKEAEKFFVSVGLPNMTQGFWENSMLTDPGNVQKAVCHPTAWDLGKGDFRILM CTKVTMDDFLTAHHEMGHIQYDMAYAAQPFLLRNGANEGFHEAVGEIMSLSAATPKHLKS IGLLSPDFQEDNETEINFLLKQALTIVGTLPFTYMLEKWRWMVFKGEIPKDQWMKKWVVEM KREIVGVVEPVPHDETYCDPASLFHVSNDYSFIRYYTRTLYQFQFQEALCQAAKHEGPLHKC DISNSTEAGQKLL |
| 17 | Human ACE2 isoform 1 extracellular domain | QSTIEEQAKTFLDKFNHEAEDLFYQSSLASWNYNTNITEENVQNMNNAGDKWSAFLKEQST LAQMYPLQEIQNLTVKLQLQALQQNGSSVLSEDKSKRLNTILNTMSTIYSTGKVCNPDNPQE CLLLEPGLNEEMANSLDYNERLWAWESWRSEVGKQLRPLYEEYVVLKNEMARANHYEDY GDYWRGDYEVNGVDGYDYSRGQLIEDVEHTFEEEKPLYEHLHAYVRAKLMNAYPSYISPIG CLPAHLLGDIVIWGRFVVTNLYSLTVPFGQKPNIDVTDAMVDQAWDAQRIFKEAEKFFVSVGL PNMTQGFVVENSMLTDPGNVQKAVCHPTAWDLGKGDFRILMCTKVTMDDFLTAHHEMGHI QYDMAYAAQPFLLRNGANEGFHEAVGEEMSLSAATPKHLKSIGLLSPDFQEDNETEINFLLK QALTIVGTLPFTYMLEKWRWMVFKGEIPKDQWMKKWVVE1VIKREIVGVVEPVPHDETYCDP ASLFHVSNDYSFIRYYTRTLYQFQFQEALCQAAKHEGPLHKCDISNSTEAGQKLFNMLRLG KSEPWTLALENVVGAKNMNVRPLLNYFEPLFTVVLKDQNKSNFVGWSTDWSPYADQSEKV RISLKSALGDKAYEWNDNEMYLFRSSVAYAMRQYFLKVKNQMILFGEEDVRVANLKPRIS FNFFVTAPKNVSDIIPRTEVEKAIRMSRSRINDAFRLNDNSLEFLGIQPTLGPPNQPPVS |
| 18 | Bat (Rhinolophus ferrumequinum) ACE2 | MSGSSWFLLSLVAVTAAQSTTEDLAKKFLDDFNSEAENLSHQSSLASWEYNTNISDENVQK MDEAGAKWSDFYEKQSKLAKNFSLEEHENDTVKLQLQILQQSGSPVLSEDKSKRLNSILNA MSTIYSTGKVCKPNNPQECLLLEPGLDNIMGTSKDYNERLWAWEGWRAEVGKQLRPLYEE YVVLKNEMARGYHYEDYGDYWRRDYETEGSPDLEYSRDQLEKDVERIFAEIKPLYEQLHA YVRTKLMDTYPFHISPTGCLPAHLLGDIVIWGRFWTNLYPLTVPPFGQKPNDVTDAMLNQNVV DAKRIFKEAEKFLVSIGLPNMTEGFWNNSMLTDPGDGRKVVCHPTAWDLGKGDFRIKMCT KVTMEDFLTAHHEMGHIQYDMAYASQPYLLRNGANEGFHEAVGEVMSLSVATPEHLKTM GLLSSDFLEDNETEINFLFKQALNIVGTLPLTYMLEKWRWMVFKGEIPKEEWMKKWVVEMK RKIVGVVEPVPHDETYCDPASLFHVANDYSFIRYYTRTIFEFQFHEALCRIAKHDGPLHKCGI SNSTDAGEKLHQMLSVGKSQPWTSVLKDFVGSKNMDVGPLLRYFEPLYTWLTEQNRKSFV GWNTDWSPYADQSIKVWISLKSALGEKAYEWNNNEMYLFRSSVAYAMREYFLKTKNQTIL FGEEDVWVSNLKPRISFNFYVTSPRNLSDIIPRPEVEGAIRMSRSRINDAFRLDDNSLEFLGIQ PTLGPPYQPPVTIWLIVFGVVMAVVVGIVVLIITGIRDRRKKDQARSEENPYSSVDLSKGEN NPGFQNGNDVQTSF |
| 19 | Bat (Rhinolophus ferrumequinum) ACE2 extracellular domain | QSTTEDLAKKFLDDFNSEAENLSHQSSLASWEYNTNISDENVQKMDEAGAKWSDFYEKQS KLAKNFSLEEHENDTVKLQLQILQQSGSPVLSEDKSKRLNSILNAMSTIYSTGKVCKPNNPQE CLLLEPGLDNEVIGTSKDYNERLWAWEGWRAEVGKQLRPLYEEYVVLKNEMARGYHYED YGDYWRRDYETEGSPDLEYSRDQLIKDVERIFAEIKPLYEQLHAYVRTKLMDTYPFHISPTG CLPAHLLGDIVIWGREWTNLYPLTVPFGQKPNEDVTDAMLNQNVVDAKRIFKEAEKFLVSIGL PNMTEGFWNNSMLTDPGDGRKVVCHPTAWDLGKGDFREKMCTKVTMEDFLTAHHEMGHI QYDMAYASQPYLLRNGANEGFHEAVGEVMSLSVATPEHLKTMGLLSSDFLEDNETEINFLF KQALNIVGTLPLTYMLEKWRWMVFKGEIPKEEWMKKWVVE1VIKRKIVGVVEPVPHDETYC DPASLFHVANDYSFIRYYTRTIFEFQFHEALCRIAKHDGPLHKCGISNSTDAGEKLHQMLSV GKSQPWTSVLKDEVGSKNMDVGPLLRYEEPLYTWLTEQNRKSFVGWNTDWSPYADQSIKV WISLKSALGEKAYEWNNNEMYLFRSSVAYAMREYFLKTKNQTILFGEEDVWVSNLKPRISF NFYVTSPRNLSDIIPRPEVEGAIRMSRSRINDAFRLDDNSLEFLGIQPTLGPPYQPPVT |
| 20 | Pangolin (Mains javanica) ACE2 | MSGSSWLLLSLVAVTAAQSTSDEEAKTFLEKFNSEAEELSYQSSLASWNYNTNITDENVQK MNVAGAKWSTFYEEQSKIAKNYQLQNIQNDTIKRQLQALQLSGSSALSADKNQRLNTILNT MSTIYSTGKVCNPGNPQECSLLEPGLDNIMESSKDYNERLWAWEGWRSEVGKQLRPLYEE YVVLKNEMARANHYEDYGDYWRGDYEAEGANGYNYSRDHLIEDVEH1FTQIKPLYEHLH AYVRAKLMDNYPSHISPTGCLPAHLLGDIVIWGREWTNLYPLTVPFRQKPNIDVTDAMVNQT WDANRIFKEAEKFFVSVGLPKMTQTFWENSMLTEPGDGRKVVCHPTAWDLGKHDFREKM CTKVTMDDFLTAHHEMGHIQYDMAYAMQPYLLRNGANEGFHEAVGEIMSLSAATPKHLK NIGLLPPDFYEDNETEINFLLKQALTIVGTLPFTYMLEKWRWMVESGQIPKEQWMKKWVVE MKREIVGVVEPVPHDETYCDPASLFHVANDYSF1RYYTRTIYQFQFQEALCQTAKHEGPLHK CDISNSAEAGQKLLQMLSLGKSKPWTLALERVVGTKNMDVRPLLNYFEPLLTWLKEQNKN SFVGWNTDWSPYAAQSEKVRISLKSALGEKAYEWNDSEMYLFRSSVAYAMREYFSKVKKQ TIPFEDECVRVSDLKPRVSFIFFVTLPKNVSAVIPRAEVEEAIRISRSRINDAFRLDDNSLEFLGI QPTLQPPYQPPVTIWLIVEGVVMGVVVVGIVVLIFTGIRDRKKKDQARSEQNPYASVDLSKG ENNPGFQNVDDVQTSF |
| 21 | Pangolin (Mains javanica) ACE2 extracellular domain | QSTSDEEAKTFLEKFNSEAEELSYQSSLASWNYNTNITDENVQKMNVAGAKWSTFYEEQSK IAKNYQLQNIQNDTEKRQLQALQLSGSSALSADKNQRLNTILNTMSTIYSTGKVCNPGNPQE CSLLEPGLDNEVIESSKDYNERLWAWEGWRSEVGKQLRPLYEEYVVLKNEMARANHYEDY GDYWRGDYEAEGANGYNYSRDHLIEDVEHIFTQIKPLYEHLHAYVRAKLMDNYPSHISPTG CLPAHLLGDIVIWGREVVTNLYPLTVPFRQKPNIDVTDAMVNQTVVDANRIFKEAEKFFVSVGL PKMTQTFWENSMLTEPGDGRKVVCHPTAWDLGKHDFRIKMCTKVTMDDFLTAHHEMGHI QYDMAYAMQPYLLRNGANEGFHEAVGEIMSLSAATPKHLKNIGLLPPDFYEDNETEINFLL |

| SEQ ID NO: | DESCRIPTION | SEQUENCE |
|---|---|---|
| | | KQALTIVGTLPFTYMLEKWRWMVESGQIPKEQWMKKWVVE1VIKREIVGVVEPVPHDETYCD PASLFHVANDYSFIRYYTRTIYQFQFQEALCQTAKHEGPLHKCDISNSAEAGQKLLQMLSLG KSKPWTLALERVVGTKNMDVRPLLNYFEPLLTWLKEQNKNSFVGWNTDWSPYAAQSIKV RISLKSALGEKAYEWNDSEMYLFRSSVAYAMREYFSKVKKQTIPILDECVRVSDLKPRVSFI FFVTLPKNVSAVIPRAEVEEAIRISRSRINDAFRLDDNSLEFLGIQPTLQPPYQPPVT |
| 22 | Civet (*Paguma larvata*) ACE2 | MSGSFWLLLSFAALTAAQSTTEELAKTFLETFNYEAQELSYQSSVASWNYNTNITDENAKN MNEAGAKWSAYYEEQSKLAQTYPLAEIQDAKEKRQLQALQQSGSSVLSADKSQRLNTILNA MSTIYSTGKACNPNNPQECLLLEPGLDNIMENSKDYNERLWAWEGWRAEVGKQLRPLYEE YVALKNEMARANNYEDGYDYWRGDYEEEWTGGYNYSRNQLIQDVEDTFEQEKPLYQHLH AYVRAKLMDTYPSRISRTGCLPAHLLGDMWGRFWTNLYPLTVPFGQKPNIDVTDAMVNQN WDARRIFKEAEKFFVSVGLPNMTQGFWENSMLTEPGDGRKVVCHPTAWDLGKGDFRIKM CTKVTMDDFLTAHHEMGHIQYDMAYAAQPFLLRNGANEGFHEAVGEIMSLSAATPNHLKT IGLLSPAFSEDNETEINFLLKQALTIVGTLPFTYMLEKWRWMVFKGAIPKEQWMQKWVVEM KRNIVGVVEPVPHDETYCDPASLFHVANDYSF1RYYTRTIYQFQFQEALCQIAKHEGPLHKC DISNSTEAGKKLLEMLSLGRSEPWTLALERVVGAKNMNVTPLLNYFEPLFTWLKEQNRNSF VGWDTDWRPYSDQSIKVRISLKSALGEKAYEWNDNEMYLERSSIAYAMREYESKVKNQTIP FVEDNVWVSDLKPRISENFFVTFSNNVSDVIPRSEVEDAIRMSRSRINDAFRLDDNSLEFLGIE PTLSPPYRPPVTIWLIVFGVVMGAIVVGIVLLIVSGIRNRRKNDQAGSEENPYASVDLNKGEN NPGFQHADDVQTSF |
| 23 | Civet (*Paguma larvata*) ACE2 extracellular domain | QSTTEELAKTFLETFNYEAQELSYQSSVASWNYNTNITDENAKNMNEAGAKWSAYYEEQS KLAQTYPLAEIQDAKIKRQLQALQQSGSSVLSADKSQRLNTILNAMSTIYSTGKACNPNNPQ ECLLLEPGLDNEVIENSKDYNERLWAWEGWRAEVGKQLRPLYEEYVALKNEMARANNYED YGDYWRGDYEEEWTGGYNYSRNQLIQDVEDTFEQEKPLYQHLHAYVRAKLMDTYPSRISR TGCLPAHLLGDIVIWGREWTNLYPLTVPFGQKPNIDVTDAMVNQNWDARRIFKEAEKFFVSV GLPNMTQGFVVENSMLTEPGDGRKVVCHPTAWDLGKGDFREKMCTKVTMDDFLTAHHEM GHIQYDMAYAAQPFLLRNGANEGFHEAVGEIMSLSAATPNHLKTIGLLSPAFSEDNETEINF LLKQALTIVGTLPFTYMLEKWRWMVFKGAIPKEQWMQKWVVEMKRNIVGVVEPVPHDET YCDPASLFHVANDYSFIRYYTRTIYQFQFQEALCQIAKHEGPLHKCDISNSTEAGKKLLEML SLGRSEPWTLALERVVGAKNMNVTPLLNYFEPLFTWLKEQNRNSFVGWDTDWRPYSDQSI KVRISLKSALGEKAYEWNDNEMYLFRSSIAYAMREYFSKVKNQTIPFVEDNVWVSDLKPRI SENFFVTFSNNVSDVIPRSEVEDAIRMSRSRINDAFRLDDNSLEFLGIEPTLSPPYRPPVT |
| 24 | Pig (*Sus scrofa*) ACE2 | MSGSFWLLLSLIPVTAAQSTTEELAKTFLEKFNLEAEDLAYQSSLASWNYNTNITDENIQKM NDARAKWSAFYEEQSRIAKTYPLDEIQTLILKRQLQALQQSGTSGLSADKSKRLNTILNTMS TIYSSGKVLDPNNPQECLVLEPGLDEIMENSKDYSRRLWAWESWRAEVGKQLRPLYEEYV VLENEMARANNYEDYGDYWRGDYEVTGTGDYDYSRNQLMEDVERTFAEEKPLYEHLHAY VRAKLMDAYPSRISPTGCLPAHLLGDIVIWGREWTNLYPLTVPFGEKPSIDVTEAMVNQSWD AIRIFEEAEKFFVSIGLPNMTQGFWNNSMLTEPGDGRKVVCHPTAWDLGKGDFREKMCTKV TMDDFLTAHHEMGHIQYDMAYAIQPYLLRNGANEGFHEAVGEIMSLSAATPHYLKALGLL PPDFYEDSETEINFLLKQALTIVGTLPFTYMLEKWRWMVFKGEIPKEQWMQKWVVEMKREI VGVVEPLPHDETYCDPACLFHVAEDYSFIRYYTRTIYQFQFHEALCRTAKHEGPLYKCDISN STEAGQKLLQMLSLGKSEPWTLALENIVGVKTMDVKPLLSYFEPLLTWLKAQNGNSSVGW NTDWTPYADQSEKVRISLKSALGKEAYEWNDNEMYLFRSSIAYAMRNYFSSAKNETIPFGA EDVWVSDLKPRISENFFVTSPANMSDIIPRSDVEKAISMSRSRINDAFRLDDNTLEFLGIQPTL GPPDEPPVTVWLIEFGVVMGLVVVGIVVLIFTGIRDRRKKKQASSEENPYGSMDLSKGESNS GFQNGDDIQTSF |
| 25 | Pig (*Sus scrofa*) ACE2 extracellular domain | QSTTEELAKTFLEKFNLEAEDLAYQSSLASWNYNTNITDENIQKMNDARAKWSAFYEEQSR IAKTYPLDEIQTLILKRQLQALQQSGTSGLSADKSKRLNTILNTMSTIYSSGKVLDPNNPQEC LVLEPGLDEEVIENSKDYSRRLWAWESWRAEVGKQLRPLYEEYVVLENEMARANNYEDYG DYWRGDYEVTGTGDYDYSRNQLMEDVERTFAEIKPLYEHLHAYVRAKLMDAYPSRISPTG CLPAHLLGDMWGRFWTNLYPLTVPFGEKPSIDVTEAMVNQSWDAIRIFEEAEKFFVSIGLPN MTQGFVVNNSMLTEPGDGRKVVCHPTAWDLGKGDFREKMCTKVTMDDFLTAHHEMGHIQ YDMAYAIQPYLLRNGANEGFHEAVGEMSLSAATPHYLKALGLLPPDFYEDSETEINFLLKQ ALTIVGTLPFTYMLEKWRWMVFKGEIPKEQWMQKWVVEIVIKREIVGVVEPLPHDETYCDPA CLFHVAEDYSFIRYYTRTIYQFQFHEALCRTAKHEGPLYKCDISNSTEAGQKLLQMLSLGKS EPWTLALENIVGVKTMDVKPLLSYFEPLLTWLKAQNGNSSVGWNTDWTPYADQSEKVRISL KSALGKEAYEWNDNEMYLFRSSIAYAMRNYFSSAKNETIPFGAEDVWVSDLKPRISENFEV TSPANMSDIIPRSDVEKAISMSRSRINDAFRLDDNTLEFLGIQPTLGPPDEPPVT |
| 26 | SARS-CoV-2 spike protein RBD | PNITNLCPFGEVFNATRFASVYAWNRKRISNCVADYSVLYNSASFSTFKCYGVSPTKLNDLC FTNVYDSFVIRGDEVRQIAPGQTGKIADYNYKLPDDFTGCVIAWNSNNLDSKVGGNYNYLY RLFRKSNLKPFERDISTEIYQAGSTPCNGVEGFNCYFPLQSYGFQPTNGVGYQPYRVVVLSPE LLHAPATVCGPKKS |
| 27 | SARS-CoV-2 spike protein S1 subunit | MLLVNQSHQGFNKEHTSKMVSAIVLYVLLAAAAHSAFAQCVNLTTRTQLPPAYTNSFTRG VYYPDKVFRSSVLHSTQDLFLPFFSNVTWFHAIHVSGTNGTKREDNPVLPFNDGVYFASTEK SNIERGWIEGTTLDSKTQSLLIVNNATNVVEKCEFQFCNDPFLGVYYHKNNKSWMESEFRV YSSANNCTFEYVSQPFLMDLEGKQGNEKNLREFVFKNEDGYFKIYSKHTPINLVRDLPQGFS ALEPLVDLPIGINITRFQTLLALHRSYLTPGDSSSGWTAGAAAYYVGYLQPRTFLLKYNENG TITDAVDCALDPLSETKCTLKSFTVEKGIYQTSNFRVQPTESIVRFPNITNLCPFGEVFNATRF ASVYAWNRKRISNCVADYSVLYNSASFSTFKCYGVSPTKLNDLCFTNVYADSFVIRGDEVR QIAPGQTGKIADYNYKLPDDFTGCVIAWNSNNLDSKVGGNYNYLYRLFRKSNLKPFERDIS |

-continued

| SEQ ID NO: | DESCRIPTION | SEQUENCE |
|---|---|---|
| | | TEIYQAGSTPCNGVEGFNCYFPLQSYGFQPTNGVGYQPYRVVVLSFELLHAPATVCGPKKST NLVKNKCVNENENGLTGTGVLTESNKKFLPFQQFGRDIADTTDAVRDPQTLEILDITPCSFG GVSVITPGTNTSNQVAVLYQDVNCTEVPVAIHADQLTPTWRVYSTGSNVFQTRAGCLIGAE HVNNSYECDIPIGAGICASYQTQTNSPRRAR |
| 28 | SARS-CoV spike protein RBD | MNITNLCPFGEVFNATKFPSVYAWERKKISNCVADYSVLYNSTFFSTFKCYGVSATKLNDL CFSNVYADSFVVKGDDVRQIAPGQTGVIADYNYKLPDDFMGCVLAWNTRNIDATSTGNYN YKYRYLRHGKLRPFERDISNVPFSPDGKPCTPPALNCYWPLNDYGFYTTTGIGYQPYRVVV LSFELLNAPATYLSLNTAAAL |
| 29 | Human ACE2 | MSSSSWLLLSLVAVTAAQSTIEEQAKTFLDKENHEAEDLEYQSSLASWNYNTNITEENVQN MNNAGDKWSAFLKEQSTLAQMYPLQEIQNLTVKLQLQALQQNGSSVLSEDKSKRLNTILN TMSTIYSTGKVCNPDNPQECLLLEPGLNEIMANSLDYNERLWAWESWRSEVGKQLRPLYEE YVVLKNEMARANHYEDYGDYWRGDYEVNGVDGYDYSRGQLIEDVEHTFEEEKPLYEHLH AYVRAKLMNAYPSYISPIGCLPAHLLGDMWGRFWTNLYSLTVPFGQKPNEDVTDAMVDQA WDAQRIFKEAEKFFVSVGLPNMTQGFWENSMLTDPGNVQKAVCHPTAWDLGKGDFRILM CTKVTMDDFLTAHHEMGHIQYDMAYAAQPFLLRNGANEGFHEAVGEIMSLSAATPKHLKS IGLLSPDFQEDNETEINFLLKQALTIVGTLPFTYMLEKWRWMVFKGEIPKDQWMKKWVVEM KREIVGVVEPVPHDETYCDPASLFHVSNDYSFIRYYTRTLYQFQFQEALCQAAKHEGPLHKC DISNSTEAGQKLFNMLRLGKSEPWTLALENVVGAKNMNVRPLLNYFEPLFTWLKDQNKNS FVGWSTDWSPYADQSEKVRISLKSALGDRAYEWNDNEMYLFRSSVAYAMRQYFLKVKNQ MILFGEEDVRVANLKPRISENFFVTAPKNVSDIIPRTEVEKAIRMSRSRINDAFRLNDNSLEFL GIQPTLGPPNQPPVSIWLIVFGVVMGVIVVGIVILIFTGIRDRKKKNKARSGENPYASEDISKGE NNPGFQNTDDVQTSF |
| 30 | Human ACE2 extrallular domain | QSTIEEQAKTFLDKENHEAEDLFYQSSLASWNYNTNITEENVQNMNNAGDKWSAFLKEQST LAQMYPLQEIQNLTVKLQLQALQQNGSSVLSEDKSKRLNTILNTMSTIYSTGKVCNPDNPQE CLLLEPGLNEIMANSLDYNERLWAWESWRSEVGKQLRPLYEEYVVLKNEMARANHYEDY GDYWRGDYEVNGVDGYDYSRGQLIEDVEHTFEEEKPLYEHLHAYVRAKLMNAYPSYISPIG CLPAHLLGDIVIWGREVVTNLYSLTVPFGQKPNIDVTDAMVDQAWDAQRIFKEAEKFFVSVGL PNMTQGFVVENSMLTDPGNVQKAVCHPTAWDLGKGDFRILMCTKVTMDDFLTAHHEMGHI QYDMAYAAQPFLLRNGANEGFHEAVGEIMSLSAATPKHLKSIGLLSPDFQEDNETEINFLLK QALTIVGTLPFTYMLEKWRWMVFKGEIPKDQWMKKWVVE1VIKREIVGVVEPVPHDETYCDP ASLFHVSNDYSFIRYYTRTLYQFQFQEALCQAAKHEGPLHKCDISNSTEAGQKLFNMLRLG KSEPWTLALENVVGAKNMNVRPLLNYFEPLFTVVLKDQNKNSFVGWSTDWSPYADQSEKV RISLKSALGDRAYEWNDNEMYLFRSSVAYAMRQYFLKVKNQMILFGEEDVRVANLKPRISF NFFVTAPKNVSDIIPRTEVEKAIRMSRSRINDAFRLNDNSLEFLGIQPTLGPPNQPPVS |
| 31 | Bat (*Rhinolophus sinicus*) ACE2 | MSSSSWLLLSLVAVTTAQFTTEDLAKIFLDEFNSEAENLSYQSSLASWDYNTNINDENVQK MDEAGAKWSAFYEEQSKLAKNYPLEQIQNVTVKLQLQILQQSGSPVL SEDKSKRLNSILNA MSTIYSTGKVCKPNKPHECLLLEPGLDNIMGTSKDYSERLWAWEGWRAEVGKQLRPLYEE YVVLKNEMARGYHYEDYGDYWRRDYETEESPGPGYSRDQL1VIKDVERIFTEIKPLYEHLHA YVRAKLMDTYPFHISPTGCLPAHLLGDIVIWGREWTNLYPLTVPFGQKPNIDVTDEMLKQGW DADRIFKEAEKFFVSVGLPNMTEGFVVNNSMLTEPGDGRKVVCHPTAWDLGKGDFREKMCT KVTMEDFLTAHHEMGHIQYDMAYASQPYLLRNGANEGFHEAVGEVMSLSVATPKHLKTM GLLSPDFREDNETEINFLLKQALNIVGTLPFTYMLEKWRWMVFKGEIPKEEWMKKWVVEMK RKIVGVVEPVPHDETYCDPASLFHVANDYSFIRYYTRTIFEFQFHEALCRIAQHDGPLHKCDI SNSTDAGKKLHQMLSVGKSQAWTKTLEDIVDSRNMDVGPLLRYFEPLYTWLQEQNRKSYV GWNTDWSPYSDQSEKVRISLKSALGENAYEWNDNEMYLFRSSVAYAMREYFLKEKHQTIL FGAENVWVSNLKPRISENFHVTSPGNLSDIIPRPEVEGAIRMSRSRINDAFRLDDNSLEFLGIQ PTLGPPYQPPVTIWLIVFGVVMAVVVVGIVVLIITGIRDRRKTDQARSEENPYSSVDLSKGEN NPGFQNGDDVQTSF |
| 32 | Bat (*Rhinolophus sinicus*) ACE2 extracellular domain | QFTTEDLAKIFLDEFNSEAENLSYQSSLASWDYNTNINDENVQKMDEAGAKWSAFYEEQSK LAKNYPLEQIQNVTVKLQLQILQQSGSPVLSEDKSKRLNSILNAMSTIYSTGKVCKPNKPHE CLLLEPGLDNIMGTSKDYSERLWAWEGWRAEVGKQLRPLYEEYVVLKNEMARGYHYEDY GDYWRRDYETEESPGPGYSRDQLIVIKDVERIFTEEKPLYEHLHAYVRAKLMDTYPFHISPTG CLPAHLLGDIVIWGREWTNLYPLTVPFGQKPNIDVTDEMLKQGWDADRIFKEAEKFFVSVGL PNMTEGFWNNSMLTEPGDGRKVVCHPTAWDLGKGDFRIKMCTKVTMEDFLTAHHEMGHI QYDMAYASQPYLLRNGANEGFHEAVGEVMSLSVATPKHLKTMGLLSPDFREDNETEINFLL KQALNIVGTLPFTYMLEKWRWMVFKGEIPKEEWMKKWWEIVIKRKIVGVVEPVPHDETYC DPASLFHVANDYSFIRYYTRTIFEFQFHEALCRIAQHDGPLHKCDISNSTDAGKKLHQMLSV GKSQAWTKTLEDIVDSRNMDVGPLLRYFEPLYTWLQEQNRKSYVGWNTDWSPYSDQSEKV RISLKSALGENAYEWNDNEMYLFRSSVAYAMREYFLKEKHQTILFGAENVWVSNLKPRISF NFHVTSPGNLSDIIPRPEVEGAIRMSRSRINDAFRLDDNSLEFLGIQPTLGPPYQPPVT |
| 33 | Pig (*Sus scrofa*) ACE2 | MSGSFWLLLSLIPVTAAQSTTEELAKTFLEKFNLEAEDLAYQSSLASWTINTNITDENIQKMN DARAKWSAFYEEQSRIAKTYPLDEIQTLILKRQLQALQQSGTSGLSADKSKRLNTILNTMSTI YSSGKVLDPNNPQECLVLEPGLDEIMENSKDYSRRLWAWESWRAEVGKQLRPLYEEYVVL ENEMARANNYEDYGDYWRGDYEVTGTGDYDYSRNQLMEDVERTFAEEKPLYEHLHAYVR AKLMDAYPSRISPTGCLPAHLLGDMWGRFWTNLYPLTVPFGEKPSEDVTEAMVNQSWDAIR IFEEAEKFFVSIGLPNMTQGFVVNNSMLTEPGDGRKVVCHPTAWDLGKGDFREKMCTKVTM DDFLTAHHEMGHIQYDMAYAIQPYLLRNGANEGFHEAVGEIMSLSAATPHYLKALGLLPPD EYEDSETEINFLLKQALTIVGTLPFTYMLEKWRWMVFKGEIPKEQWMQKWVVEIVIKREIVGV VEPLPHDETYCDPACLFHVAEDYSFIRYYTRTIYQFQFHEALCRTAKHEGPLYKCDISNSTEA |

-continued

| SEQ ID NO: | DESCRIPTION | SEQUENCE |
|---|---|---|
| | | GQKLLQMLSLGKSEPWTLALENIVGVKTMDVKPLLSYFEPLLTWLKAQNGNSSVGWNTD<br>WTPYADQSIKVRISLKSALGEDAYEWNDNEMYLFRSSIAYAMRNYFSSAKNETIPFGAVDV<br>WVSDLKPRISENFFVTSPANMSDIIPRSDVEKAISMSRSRINDAFRLDDNTLEFLGIQPTLGPP<br>DEPPVTVWLIIFGVVMGLVVVGIVVLIFTGIRDRRKKKQASSEENPYGSMDLSKGESNSGFQ<br>NGDDIQTSF |
| 34 | PIG (*Sus scrofa*) ACE2 extracellular domain | QSTTEELAKTFLEKFNLEAEDLAYQSSLASWTINTNITDENIQKMNDARAKWSAFYEEQSRI<br>AKTYPLDEIQTLILKRQLQALQQSGTSGLSADKSKRLNTILNTMSTIYSSGKVLDPNNPQECL<br>VLEPGLDEEVIENSKDYSRRLWAWESWRAEVGKQLRPLYEEYVVLENEMARANNYEDYGD<br>YWRGDYEVTGTGDYDYSRNQLMEDVERTFAEIKPLYEHLHAYVRAKLMDAYPSRISPTGC<br>LPAHLLGDMWGREWTNLYPLTVPFGEKPSIDVTEAMVNQSWDAIRIFLEAEKFFVSIGLPN<br>MTQGFVVNNSMLTEPGDGRKVVCHPTAWDLGKGDFREKMCTKVTMDDFLTAHHEMGHIQ<br>YDMAYAIQPYLLRNGANEGFHEAVGEIMSLSAATPHYLKALGLLPPDFYEDSETEINFLLKQ<br>ALTIVGTLPFTYMLEKWRWMVFKGEIPKEQWMQKWWElVIKREIVGVVEPLPHDETYCDPA<br>CLFHVAEDYSFIRYYTRTIYQFQFHEALCRTAKHEGPLYKCDISNSTEAGQKLLQMLSLGKS<br>EPWTLALENIVGVKTMDVKPLLSYFEPLLTWLKAQNGNSSVGWNTDWTPYADQSIKVRISL<br>KSALGEDAYEWNDNEMYLFRSSIAYAMRNYFSSAKNETIPFGAVDVWVSDLKPRISFNFFV<br>TSPANMSDIIPRSDVEKAISMSRSRINDAFRLDDNTLEFLGIQPTLGPPDEPPVT |

Having thus described in detail preferred embodiments of the present disclosure, it is to be understood that the disclosure defined by the above paragraphs is not to be limited to particular details set forth in the above description as many apparent variations thereof are possible without departing from the spirit or scope of the present disclosure.

REFERENCES

1. Wang, C., Horby, P. W., Hayden, F. G. & Gao, G. F. A novel coronavirus outbreak of global health concern. *Lancet* 395, 470-473, doi:10.1016/S0140-6736(20)30185-9 (2020).
2. WHO. COVID-19 Status Report. https://www.who.int/emergencies/diseases/novel-coronavirus-2019/situation-reports. Accessed on 18 Apr. 2020 (2020).
3. Zhou, P. et al. A pneumonia outbreak associated with a new coronavirus of probable bat origin. *Nature* 579, 270-273, doi:10.1038/s41586-020-2012-7 (2020).
4. Coronaviridae Study Group of the International Committee on Taxonomy of, V. The species Severe acute respiratory syndrome-related coronavirus: classifying 2019-nCoV and naming it SARS-CoV-2. *Nat Microbiol* 5, 536-544, doi:10.1038/s41564-020-0695-z (2020).
5. Peiris, J. S. et al. Coronavirus as a possible cause of severe acute respiratory syndrome. *Lancet* 361, 1319-1325 (2003).
6. Petherick, A. Developing antibody tests for SARS-CoV-2. *Lancet* 395, 1101-1102, doi:10.1016/50140-6736(20)30788-1 (2020).
7. Hoffmann, M. et al. SARS-CoV-2 Cell Entry Depends on ACE2 and TMPRSS2 and Is Blocked by a Clinically Proven Protease Inhibitor. *Cell* 181, 271-280 e278, doi:10.1016/j.cell.2020.02.052 (2020).
8. Nie, J. et al. Establishment and validation of a pseudovirus neutralization assay for SARS-CoV-2. *Emerging microbes & infections* 9, 680-686, doi:10.1080/22221751.2020.1743767 (2020).
9. Tang, Y. W., Schmitz, J. E., Persing, D. H. & Stratton, C. W. The Laboratory Diagnosis of COVID-19 Infection: Current Issues and Challenges. *J Clin Microbiol*, doi:10.1128/JCM.00512-20 (2020).
10. Okba, N. M. A. et al. Severe Acute Respiratory Syndrome Coronavirus 2-Specific Antibody Responses in Coronavirus Disease 2019 Patients. *Emerg Infect Dis* 26, doi:10.3201/eid2607.200841 (2020).
11. Stadlbauer, D. et al. SARS-CoV-2 Seroconversion in Humans: A Detailed Protocol for a Serological Assay, Antigen Production, and Test Setup. *Curr Protoc Microbiol* 57, e100, doi:10.1002/cpmc.100 (2020).
12. Li, W. et al. Angiotensin-converting enzyme 2 is a functional receptor for the SARS coronavirus. *Nature* 426, 450-454 (2003).
13. Ou, X. et al. Characterization of spike glycoprotein of SARS-CoV-2 on virus entry and its immune cross-reactivity with SARS-CoV. *Nat Commun* 11, 1620, doi:10.1038/s41467-020-15562-9 (2020).
14. BBC. Coronavirus: Double warning over antibody tests. https://www.bbc.com/news/uk-52335210 Accessed on 18-04-2020 (2020).
15. Burton, D. R. Antibodies, viruses and vaccines. *Nat Rev Immunol* 2, 706-713, doi:10.1038/nri891 (2002).
16. Klasse, P. J. Neutralization of Virus Infectivity by Antibodies: Old Problems in New Perspectives. *Adv Biol* 2014, doi:10.1155/2014/157895 (2014).
17. Li, W. et al. Bats are natural reservoirs of SARS-like coronaviruses. *Science* 310, 676-679 (2005).
18. Young, P. L. et al. Serologic evidence for the presence in Pteropus bats of a paramyxovirus related to equine morbillivirus. *Emerg Infect Dis* 2, 239-240 (1996).
19. Yob, J. M. et al. Nipah virus infection in bats (order Chiroptera) in peninsular Malaysia. *Emerg Infect Dis* 7, 439-441. (2001).
20. Smith, I. et al. Identifying Hendra virus diversity in pteropid bats. *PLoS ONE* 6, e25275, doi:10.1371/journal.pone.0025275 PONE-D-11-12458 [pii] (2011).
21. Barr, J. et al. Isolation of multiple novel paramyxoviruses from pteropid bat urine. *J Gen Virol* 96, 24-29, doi:10.1099/vir.0.068106-0 (2015).
22. Leroy, E. M. et al. Fruit bats as reservoirs of Ebola virus. *Nature* 438, 575-576 (2005).
23. Zwick, M. B. et al. Neutralization synergy of human immunodeficiency virus type 1 primary isolates by cocktails of broadly neutralizing antibodies. *J Virol* 75, 12198-12208 (2001).
24. Howell, K. A. et al. Cooperativity Enables Non-neutralizing Antibodies to Neutralize Ebolavirus. *Cell Rep* 19, 413-424, doi:10.1016/j.celrep.2017.03.049 (2017).

25. Besselaar, T. G. & Blackburn, N. K. The synergistic neutralization of Rift Valley fever virus by monoclonal antibodies to the envelope glycoproteins. *Arch Virol* 125, 239-250, doi:10.1007/bf01309641 (1992).
26. Young, B. E. et al. Epidemiologic Features and Clinical Course of Patients Infected With SARS-CoV-2 in Singapore. *JAMA*, doi:10.1001/jama.2020.3204 (2020).
27. Jiang, L. et al. Detection of viral respiratory pathogens in mild and severe acute respiratory infections in Singapore. *Sci Rep* 7, 42963, doi:10.1038/srep42963 (2017).
28. Yu, M. et al. Determination and application of immunodominant regions of SARS coronavirus spike and nucleocapsid proteins recognized by sera from different animal species. *Journal of Immunological Methods* 331, 1-12 (2008).
29. Crameri, G. et al. Experimental Infection and Response to Rechallenge of Alpacas with Middle East Respiratory Syndrome Coronavirus. *Emerg Infect Dis* 22, 1071-1074, doi:10.3201/eid2206.160007 (2016).
30. Normile D. Singapore claims first use of antibody test to track coronavirus infections. *Science* 2020, doi:10.1126/science.abb4942
31. Amanat F, Nguyen T H O, Chromikova V et al. A serological assay to detect SARS-CoV-2 seroconversion in humans. medRxiv 2020 https://doi.org/10.1101/2020.03.17.20037713.
32. Okba N M A, Muller M A, Li W et al. SARS-CoV-2 specific antibody responses in COVID-19 patients. medRxiv 2020 medRxiv https://doi.org/10.1101/2020.03.18.20038059.
33. Schuh A J, Amman B R, Sealy T K et al. Antibody-Mediated Virus Neutralization Is Not a Universal Mechanism of Marburg, Ebola, or Sosuga Virus Clearance in Egyptian Rousette Bats. J Infect Dis 2019 219(11):1716-1721.
34. Li F, Li W, Farzan M, Harrison S C. Structure of SARS coronavirus spike receptor-binding domain complexed with receptor. Science 2005 309(5742):1864-8. S
35. Zhu Z, Chakraborti S, He Y et al. Potent cross-reactive neutralization of SARS coronavirus isolates by human monoclonal antibodies. Proc Natl Acad Sci USA 2007 104(29):12123-8.
36. Bossart K N, McEacherna J A, Hickey A C et al. Neutralization assays for differential henipavirus serology using Bio-Plex Protein Array Systems. J Viol Meth 2007 142: 29-40.
37. Lam T T-Y, Sum M H-H, Zhu H-C et al. Identification of 2019-nCoV related coronaviruses in Malayan pangolins in southern China. bioRxiv 2020 https://doi.org/10.1101/2020.02.13.945485.
38. Wang N, Shi X, Jiang L et al. Structure of MERS-CoV spike receptor-binding domain complexed with human receptor DPP4. Cell Res 2013 23(8):986-93.

What is claimed is:

1. A kit for detecting neutralizing antibodies to a severe acute respiratory syndrome-related coronavirus (SARSr-COV), comprising:
   (i) a SARS-COV-1 or -2 spike protein or an ACE2-binding fragment of a SARS-COV-1 or -2 spike protein,
   (ii) a human ACE2 protein or a SARS-CoV-1 or -2 receptor binding domain (RBD) binding fragment of a human ACE2 protein thereof which binds specifically to the spike protein or the fragment thereof of (i), and
   a detection entity comprising a horseradish peroxidase, for detecting interaction between the spike protein or the ACE2-binding fragment of (i) and the human ACE2 protein or RBD binding fragment of (ii),
   wherein the spike protein or the ACE2-binding fragment of (i) is conjugated to the detection entity; and the human ACE2 protein or the RBD binding fragment of (ii) is immobilised on a solid support.

2. The kit according to claim 1,
   wherein the kit is for detecting neutralizing antibodies to SARSr-COV in a sample and the sample is a blood sample, a lymph sample, a saliva sample, or a synovial fluid sample and the SARSr-CoV is SARS-CoV-2.

3. The kit according to claim 1, wherein the SARSr-CoV is SARS-CoV-2.

4. The kit according to claim 1, wherein the spike protein or the ACE2-binding fragment of (i) comprises an S1 subunit that comprises an amino acid sequence comprising SEQ ID NO: 12 or 27.

5. The kit according to claim 1, wherein the kit is for performing a method of analysing a sample for the presence of neutralizing antibodies to a SARSr-CoV, comprising: contacting the sample with (i) the spike protein or the ACE2-binding fragment, and (ii) the human ACE2 protein or the RBD binding fragment, and determining the level of interaction between the spike protein or ACE2-binding fragment of (i) and the human ACE2 protein or the RBD binding fragment of (ii), and
   wherein
   the spike protein or the ACE2-binding fragment of (i) is at a quantity that is:
   (a) sufficient to produce a detectable signal of interaction between the spike protein or the ACE2-binding fragment of (i) and the human ACE2 protein or the RBD binding fragment of (ii) in the absence of the sample, and/or
   (b) less than or equal to, in molar ratio, the quantity of the antibodies to the SARSr-CoV in the sample, and/or
   (c) a minimal quantity required to produce a detectable signal of interaction between the spike protein or the ACE2-binding fragment of (i) and the ACE2 protein or the RBD binding fragment of (ii) in the absence of the sample.

6. The kit according to claim 1, wherein the RBD comprises an amino acid sequence comprising SEQ ID NO: 13 or 26.

7. The kit according to claim 1, wherein the ACE2 protein or the RBD-binding fragment of (ii) comprises an ACE2 protein extracellular domain having an amino acid sequence comprising SEQ ID NO: 17 or 30.

8. The kit according to claim 5, wherein the spike protein or the ACE2-binding fragment of (i) comprises an S1 subunit that comprises an amino acid sequence comprising SEQ ID NO: 12 or 27.

9. The kit according to claim 1, wherein the kit is for performing a method of analysing a sample for the presence of neutralizing antibodies to a SARSr-CoV, comprising: contacting the sample with (i) the spike protein or the ACE2-binding fragment, and (ii) the human ACE2 protein or the RBD binding fragment, and determining the level of interaction between the spike protein or ACE2-binding fragment of (i) and the human ACE2 protein or the RBD binding fragment of (ii).

10. The kit according to claim 9, wherein the sample is a blood sample, a lymph sample, a saliva sample, or a synovial fluid sample.

11. The kit according to claim 9, wherein the SARSr-CoV is SARS-CoV-2.

12. The kit according to claim 5, wherein the RBD comprises an amino acid sequence comprising SEQ ID NO: 13 or 26.

13. The kit according to claim 5, wherein the ACE2 protein or the RBD-binding fragment of (ii) comprises an ACE2 protein extracellular domain having an amino acid sequence comprising SEQ ID NO: 17 or 30.

14. The kit according to claim 9, wherein the spike protein or the ACE2-binding fragment of (i) comprises an S1 subunit that comprises an amino acid sequence comprising SEQ ID NO: 12 or 27.

15. The kit according to claim 5, wherein the sample is a blood sample, a lymph sample, a saliva sample, or a synovial fluid sample.

16. The kit according to claim 9, wherein the RBD comprises an amino acid sequence comprising SEQ ID NO: 13 or 26.

17. The kit according to claim 9, wherein the ACE2 protein or the RBD binding fragment of (ii) comprises an ACE2 protein extracellular domain having an amino acid sequence comprising SEQ ID NO: 17 or 30.

18. The kit according to claim 9, wherein the spike protein or the ACE2-binding fragment of (i) is at a quantity that is (a) sufficient to produce a detectable signal of interaction between the spike protein or the ACE2-binding fragment (i) and the ACE2 protein or the RBD binding fragment of (ii) in the absence of the sample, and (b) less than or equal to, in molar ratio, the quantity of the antibodies to the SARSr-CoV in the sample.

19. The kit according to claim 9, wherein the spike protein or the ACE2-binding fragment of (i) is at a minimal quantity required to produce a detectable signal of interaction between the spike protein or the ACE2-binding fragment of (i) and the ACE2 protein or the RBD binding fragment of (ii) in the absence of the sample.

20. The kit according to claim 5, wherein the spike protein or the ACE2-binding fragment of (i) is at a quantity that is: (a) sufficient to produce a detectable signal of interaction between the spike protein or the ACE2-binding fragment of (i) and the ACE2 protein or the RBD binding fragment of (ii) in the absence of the sample.

21. The kit according to claim 5, wherein the spike protein or the ACE2-binding fragment of (i) is at a quantity that is: (c) a minimal quantity required to produce a detectable signal of interaction between the spike protein or the ACE2-binding fragment of (i) and the ACE2 protein or the RBD binding fragment of (ii) in the absence of the sample.

22. The kit according to claim 20, wherein the sample is a blood sample, a lymph sample, a saliva sample, or a synovial fluid sample and the SARSr-CoV is SARS-CoV-2.

23. The kit according to claim 21, wherein the sample is a blood sample, a lymph sample, a saliva sample, or a synovial fluid sample and the SARSr-CoV is SARS-CoV-2.

24. The kit according to claim 22, wherein the spike protein or the ACE2-binding fragment of (i) comprises an S1 subunit that comprises the amino acid sequence set forth in SEQ ID NO: 12 or 27, or the RBD comprises an amino acid sequence comprising SEQ ID NO: 13 or 26, or the ACE2 protein or the RBD binding fragment of (ii) comprises an ACE2 protein extracellular domain having an amino acid sequence comprising SEQ ID NO: 17 or 30.

25. The kit according to claim 23, wherein the spike protein or the ACE2-binding fragment of (i) comprises an S1 subunit that comprises the amino acid sequence set forth in SEQ ID NO: 12 or 27, or the RBD comprises an amino acid sequence comprising SEQ ID NO: 13 or 26, or the ACE2 protein or the RBD binding fragment of (ii) comprises an ACE2 protein extracellular domain having an amino acid sequence comprising SEQ ID NO: 17 or 30.

26. The kit according to claim 9, wherein the sample is a blood sample, a lymph sample, a saliva sample, or a synovial fluid sample and the SARSr-CoV is SARS-CoV-2.

27. The kit according to claim 5, wherein the sample is a blood sample, a lymph sample, a saliva sample, or a synovial fluid sample and the SARSr-CoV is SARS-CoV-2.

28. The kit according to claim 1, wherein the kit is for detecting neutralizing antibodies to SARSr-COV in a sample and the sample is a blood sample, a lymph sample, a saliva sample, or a synovial fluid sample.

29. The kit according to claim 5, wherein the SARSr-CoV is SARS-CoV-2.

30. The kit according to claim 2, wherein the spike protein or the ACE2-binding fragment of (i) comprises an S1 subunit that comprises the amino acid sequence set forth in SEQ ID NO: 12 or 27, or the RBD comprises an amino acid sequence comprising SEQ ID NO:
13 or 26, or the ACE2 protein or the RBD binding fragment of (ii) comprises an ACE2 protein extracellular domain having an amino acid sequence comprising SEQ ID NO: 17 or 30.

* * * * *